(12) United States Patent
Chen et al.

(10) Patent No.: US 6,486,213 B1
(45) Date of Patent: Nov. 26, 2002

(54) BLOCK AND GRAFT COPOLYMERS AND METHODS RELATING THERETO

(75) Inventors: Guohua Chen, Seattle, WA (US); Allan S. Hoffman, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 08/483,475

(22) Filed: Jun. 7, 1995

Related U.S. Application Data

(63) Continuation-in-part of application No. 08/205,712, filed on Mar. 4, 1994, now abandoned.

(51) Int. Cl.⁷ .................... A61K 47/30; A61K 47/36; A61L 51/00; A61L 101/08
(52) U.S. Cl. ................ 514/772.1; 514/772.6; 514/781; 525/78; 525/54.21
(58) Field of Search .................. 424/487, 488, 424/486, 78.17, 78.18–78.19; 514/772.1, 772.4–772.6; 525/78, 54.21

(56) References Cited

U.S. PATENT DOCUMENTS 3,575,700 A   4/1971  Taylor ................ 96/3

(List continued on next page.)

FOREIGN PATENT DOCUMENTS

| EP | 091 313 | 10/1983 |
|---|---|---|
| EP | 122 658 | 7/1984 |
| EP | 126 684 | 11/1984 |
| EP | 316 792 A2 | 5/1989 |
| EP | 391 108 A2 | 10/1990 |
| EP | 629 649 | 12/1994 |
| GB | 1141271 | 1/1969 |
| GB | 2007091 | 5/1979 |
| GB | 2013084 | 8/1979 |
| GB | 1571832 | 7/1980 |
| WO | WO 92/05770 | 4/1992 |
| WO | WO 93/17716 | 6/1993 |

OTHER PUBLICATIONS

Katono et al., "Thermo–responsive swelling and drug release switching of interpenetrating polymer networks composed of poly (acrylamide–co–butyl methacrylate) and poly (acrylic acid)," *Journal of Controlled Release* 16: 215–228, 1991.

(List continued on next page.)

*Primary Examiner*—Edward J. Webman
(74) *Attorney, Agent, or Firm*—Seed Intellectual Property Law Group PLLC

(57) ABSTRACT

There is disclosed block and graft copolymers, and hydrogels thereof, which, in one embodiment, contain both a temperature-sensitive polymer component and a pH-sensitive polymer component, and the use of such copolymers for topical drug delivery to a treatment area. The block and graft copolymers may be physically mixed with one or more drugs (or with other polymers) to form a copolymer-drug mixture. These mixtures may be applied as solid particles suspended in a pharmaceutically acceptable carrier, or as a liquid which gels upon contact with the treatment area. Upon contact with the treatment area, the pH-sensitive polymer component hydrates and swells, thereby causing release of the drug from the mixture. In addition, such hydration and swelling causes the pH-sensitive polymer component to adhere to the tissue of the treatment area, thus prolonging contact time. The temperature-sensitive polymer component resists hydration and swelling of the mixture, thereby imparting a sustained and controlled release of the drug to the treatment area. In another embodiment of this invention, block and graft copolymers, and hydrogels thereof, are disclosed having broad industrial applicability.

21 Claims, 19 Drawing Sheets

U.S. PATENT DOCUMENTS

| | | | |
|---|---|---|---|
| 3,575,701 A | | 4/1971 | Taylor .............................. 96/3 |
| 3,746,548 A | * | 7/1973 | Fitzgerald et al. |
| 4,188,373 A | | 2/1980 | Krezanoski .................. 424/78 |
| 4,452,818 A | | 6/1984 | Haidt ......................... 424/352 |
| 4,605,721 A | * | 8/1986 | Jenkins et al. |
| 4,731,092 A | * | 3/1988 | Barendt |
| 4,748,211 A | * | 5/1988 | Das et al. |
| 4,888,168 A | | 12/1989 | Potts et al. ................... 424/78 |
| 5,174,988 A | | 12/1992 | Mautone et al. .............. 424/45 |
| 5,188,826 A | | 2/1993 | Chandrasekaram et al. .... 4242/78.03 |
| 5,192,535 A | | 3/1993 | Davis et al. ............. 424/78.04 |
| 5,252,318 A | | 10/1993 | Joshi et al. .............. 424/78.04 |

OTHER PUBLICATIONS

Kim et al., "pH/Temperature–sensitive polymers for macromolecular drug loading and release," *Journal of Controlled Release* 28: 143–152, 1994.

Takeuchi and Omodaka, "Temperature–responsive graft copolymers for immobilization of enzymes," *Makromol. Chem.* 194: 1991–1999, 1993.

"Thermothickening Polyelectrolytes," *American Chemical Society Meeting*, Abstract #96, Denver, Colorado, Mar. 1993.

Chen and Hoffman, "Thermal and pH–Sensitive Polymers for Use as Water–Soluble–Insoluble Polymer–Enzyme Conjugates," in *The 19th Annual Meeting of the Society for Biomaterials*, Birmingham, Alabama, Apr. 28–May 2, 1993.

Chen and Hoffman, "Preparation and Properties of Thermoreversible, Phase–Separating Enzyme–Oligo (N–isopropylacrylamide) Conjugates," *Bioconjugate Chem.* 4(509): 509–514, 1993.

Chen and Hoffman, "Synthesis of Carboxylated Poly(NIPAAm) Oligomers and Its Application to Form Thermo–Reversible Polymer–Enzyme Conjugates," *ACS Polymer Reprints*, pp. 468–469, 1992.

Dong and Hoffman, "A Novel Approach for Preparation of pH–Sensitive Hydrogels for Enteric Drug Delivery," *Journal of Controlled Release 15:* 141–152, 1991.

Chen et al., "Polymer–Protein Conjugates: I. Effect of Protein Conjugation on the Cloud Point of Poly(N–isopropylacrylamide)," *Biomaterials 11:* 625–636, 1990.

Hazra et al., "Protein Determination with Trinitrobenzene Sulfonate: A Method Relatively Independent of Amino Acid Composition," *Analytical Biochemistry 137:* 437–443, 1984.

Takei et al., "Temperature–Responsive Bioconjugates. 1. Synthesis of Temperature–Responsive Oligomers with Reactive End Groups and Their Coupling to Biomolecules," *Bioconjugate Chem. 4:* 42–46, 1993.

"Polymer Gets Smarter," *Science 259:* 893, 1993.

Takeuchi et al., "Microspheres Prepared with a Temperature–Responsive Macromonomer," *Makromol. Chem. 194:* 551–558, 1993.

Heskins and Guillet, "Solution Properties of Poly(N–isopropylacrylamide)," *J. Macromol. Sci. Chem. A2(8):* 1441–1455, 1968.

* cited by examiner

BLOCK AND GRAFT COPOLYMERS AND METHODS RELATING THERETO

CROSS-REFERENCE TO RELATED APPLICATIONS

This application is a continuation-in-part of U.S. Ser. No. 08/205,712 filed Mar. 4, 1994, now abandoned, and claims priority from PCT Application No. PCT/US95/02638 filed Mar. 3, 1995.

TECHNICAL FIELD

This invention relates generally to block and graft copolymers, and more specifically, to block and graft copolymers which are effective in drug delivery, including copolymer-drug mixtures for the delivery and controlled release of a drug by topical application.

BACKGROUND OF THE INVENTION

The effective and efficient delivery of a therapeutic drug to a patient is a goal of pharmaceutical science. Targeted drug delivery, such as topical application of a therapeutic drug to a site of action, has many advantages over systemic drug delivery. Typically, adverse side effects associated with systemic delivery may be greatly reduced when a therapeutic drug is delivered locally to the site of action by topical administration. Therapeutic drugs which are systemically administrated are dispersed relatively non-selectively throughout the patient's body and metabolized, thus reducing their therapeutic effectiveness with respect to dosage, as well as increasing the likelihood of adverse reaction. In contrast, an effective dosage of a topically administered therapeutic drug is often significantly less than that required through systemic administration. The diminution of dosage accompanying topical administration reduces the possibility of adverse reaction to the drug. In addition, drug metabolism of topically administered therapeutics is also minimized, thereby increasing their effectiveness.

While advantageous to systemic delivery, topical administration of a therapeutic drug is far from ideal. Perhaps the greatest single drawback to topical drug administration is the actual delivery of the therapeutic drug to the tissue to be treated. The absorption of the therapeutic drug by the tissue is often a slow process, and therefore requires a relatively long contact time between the tissue and the topical formulation containing the therapeutic drug. For example, topical administration of solutions of therapeutic drugs can be rather problematic. The use of viscous solutions, gels, ointments, lotions, patches, and inserts containing therapeutic drugs is a routine alternative to the administration of therapeutics in solution. These alternative formulations serve to enhance the contact time between the therapeutic drug and the tissue to be treated, thereby increasing the effectiveness of the topical treatment.

Ophthalmic drug delivery presents unique problems. Traditionally, eyedrops are the preferred mode of topical delivery of therapeutic drugs to the eye. Indeed, solutions of therapeutic drugs are routinely administered by this technique. However, it is well known that a major loss of drugs administered to the eye is via the lacrimal drainage system. This drainage is so effective that only a small fraction of the therapeutic drug remains in contact with the eye for any extended period of time. Consequently, topical delivery of therapeutic drugs to the eye via an eyedrop solution is relatively ineffective and requires repetitive treatments. The usual alternatives to the administration of solutions, such as the use of ointments and lotions to prolong tissue contact, are not particularly suitable for drug administration to the eye. Ointments and lotions are physically difficult to administer to the eye, and drug dosage is therefore difficult to control. The use of solid inserts has also been utilized to deliver therapeutic drugs to the eye. While this technique does assure a slow, effective release of the drug, patients often experience difficulty in placing and removing the insert into the cul-de-sac of the eye.

An alternative approach to ophthalmic drug delivery is the use of therapeutic drug formulations which are liquids at room temperature and which are transformed into gels upon warming through contact with tissue. These formulations, deliverable to the eye as liquid drops, may be readily dispensed and their dosage controlled. More significantly, once the liquid formulation is transformed into a gel on the surface of the eye, drainage of the therapeutic drug is retarded and its residence time on the eye is prolonged. The gelling of these formulations is attributable to polymer components which undergo solution-to-gel transitions in response to relatively small changes in environmental conditions (also called "triggers"), such as temperature or pH. Polymers which undergo solution-to-gel transition upon changes in temperature are often referred to as "thermally gelling polymers" or "temperature-sensitive polymers." Similarly, polymers which undergo solution-to-gel transition as a result of a change in pH are generally referred to as "pH-sensitive polymers."

Temperature-sensitive polymers which form gels upon warming undergo a solution-to-gel transition at their lower critical solution temperature ("LCST"), also referred to as the "cloud point." The formation of the gel is believed to result from the gathering of portions of the temperature-sensitive polymers into hydrophobic micro-domains which are maintained in the aqueous gel phase by the hydrophilic portion of the polymer. Such temperature-sensitive polymers, although water soluble at low temperature, generally possess some hydrophobic character. The polymer's hydrophobic character is imparted by part of the monomer or repeat unit from which the polymer is derived. For example, poly(N-isopropylacrylamide) ("NIPAAm") is well known to change its structure in response to temperature in aqueous solutions (see, e.g., Heskins et al., *J. Macromol. Sci. Chem.* A2, 1441–45, 1968). At temperatures below the LCST of NIPAAm (i.e., 32° C.), polymer chains of NIPAAm hydrate to form an expanded structure, while at temperatures above the LCST the chains form a compact structure which excludes water. Thus, gel formation is due to the association of the relatively hydrophobic isopropyl groups of the NIPAAm polymer.

Temperature-sensitive polymers have been employed as vehicles for ophthalmic drug delivery. For example, block copolymers of ethylene oxide and propylene oxide have been disclosed in U.S. Pat. No. 4,188,373 for this purpose. However, in this system, the concentration of the polymer must be adjusted to provide the desired solution-to-gel transition temperature. The drawback to this system is that in order to achieve a solution-to-gel temperature suitable for gelling at body temperature, the polymer must be present at a relatively low concentration. Thus, the ability to obtain a gel with the desired properties is limited by the desired physiologically useful temperature range. The necessity for a low polymer concentration, in turn, limits the amount of drug that may be administered by such a polymer system.

Polymers which are sensitive to changes in pH, such as polyacrylic acid ("polyAAc"), have also been utilized to form gels in situ, including use as vehicles in ophthalmic compositions. For example, U.S. Pat. No. 4,888,168 discloses a composition containing the homopolymer polyAAc, and gel formation occurs upon the subsequent addition of an acidic component. Gel formation results in this case by an increase in viscosity associated with the protonation of the carboxylic acid groups at low pH. In water at neutral pH, the carboxy groups of polyAAc are ionized and the polymer is a liquid-in-water solution. Lowering the pH to 4.3–4.5 by the addition of an acid, such as citric acid, results in gel formation due to formation of H-bonded crosslinks between —COOH groups. An undesirable limitation of this system for use as an ophthalmic drug delivery vehicle is that gel formation requires sequential addition of two solutions (i.e., a first polyAAc solution and a second acid solution). In addition, the pH of such an acid solution is undesirable to the eye.

Due to the drawbacks of existing temperature-sensitive and pH-sensitive polymers to provide suitable vehicles for topical drug delivery, researchers have studied random copolymers containing these components for use as a vehicle for topical drug delivery. Such random copolymers, however, have not proved suitable for physiological application. In particular, random copolymers of temperature-sensitive and pH-sensitive monomers quickly lose their temperature sensitivity upon increasing the content or ratio of the pH-sensitive monomers relative to the temperature-sensitive monomers. Thus, by employing a ratio of the pH-sensitive component sufficient to impart pH sensitivity to the random copolymer, such a ratio destroys the temperature sensitivity sought by incorporation of the temperature-sensitive components. In addition, cross-linking such random copolymers to form a hydrogel does not alleviate the problem. For example, cross-linked hydrogels of a random copolymer of acrylic acid ("AAc") and NIPAAm, when used as a vehicle for drug delivery, releases the drug at a more rapid rate as the AAc content of the random copolymer is increased (Dong and Hoffman, *J. Controlled Release* 15:141–152, 1991).

Similarly, attempts have been made to employ aqueous solutions containing a mixture of temperature-sensitive and pH-sensitive polymers for ophthalmic drug delivery. Such mixtures, however, have also been met with only limited success. For example, U.S. Pat. No. 5,252,318 is directed to physical mixtures of temperature-sensitive and pH-sensitive reversibly gelling polymers. At physiological temperature and in buffered saline, such physical mixtures, when used for drug delivery, tend to separate as the temperature-sensitive polymer precipitates and the pH-sensitive polymer ionizes. Thus, such polymer mixtures are largely ineffective due to loss of drug through drainage from the eye.

Despite the advantages associated with the use of gel-forming polymers as vehicles for topical ophthalmic drug delivery, limitations to their utility persist. As mentioned above, these formulations are delivered as solutions and are thus susceptible to drainage from the eye before gel formation can be effected. Accordingly, there is a need in the art for a simple, dosage reliable, topically administrable composition which provides for delivery of a therapeutically effective amount of a drug which does not suffer rapid drainage from the treatment area. In addition, there is a need in the art for methods relating to the use of such compositions for topical drug delivery. The present invention fulfills these needs, and provides further related advantages.

SUMMARY OF THE INVENTION

In brief, environmentally-sensitive block and graft copolymers are disclosed. The environmentally-sensitive copolymers of this invention respond to environmental changes in, for example, temperature, pH, pressure, light, solvent or solvent concentration and ions or ionic strength. Accordingly, the environmentally-sensitive polymers of this invention include pH-sensitive, temperature-sensitive, pressure-sensitive, photo-sensitive, solvent-sensitive, solvent concentration-sensitive, ion-sensitive and ionic strength-sensitive polymer components. Such copolymers are particularly useful as vehicles for the controlled release of therapeutic drugs. In one embodiment, this invention is directed to graft copolymers comprising a backbone pH-sensitive polymer component with a pendant temperature-sensitive polymer component grafted thereto, or a backbone temperature-sensitive polymer component with a pendant pH-sensitive polymer component grafted thereto. In either case, the graft copolymers may have a lower solution critical temperature ("LCST"), a melting temperature or glass transition temperature (collectively referred to herein as "a critical temperature") ranging from 20° C. to 40° C. at physiological pH.

In a related embodiment, there is disclosed block copolymers comprising a pH-sensitive polymer component and a temperature-sensitive polymer component joined thereto. As with the graft copolymers, the block copolymers of this invention may also have a critical temperature ranging from 20° C. to 40° C. at physiological pH.

The pH-sensitive polymer component of the block and graft copolymers preferably comprises a polymer which has bioadhesive properties, such as a carboxylic acid-containing polymer component derived from polymerizable carboxylic acids (such as acrylic acid and methacrylic acid), and preferably are either homopolymers or copolymers containing only a limited quantity of comonomer. The temperature-sensitive polymer component preferably has critical temperature ranging from 20° C. to 40° C. at physiological pH, and may be a homopolymer or a random or block copolymer. The pH-sensitive or temperature-sensitive polymer components may also be lightly cross-linked, resulting in cross-linked block and graft copolymer hydrogels.

In another embodiment, the present invention is directed to a physical mixture of a block or graft copolymer or hydrogel with a pharmaceutically acceptable drug to form a copolymer-drug mixture. For topical application to a treatment area, the copolymer-drug mixture is applied as a solid particle suspended in a pharmaceutically acceptable carrier. Alternatively, the copolymer may be dissolved in a pharmaceutically acceptable carrier in combination with the pharmaceutically acceptable drug and applied as a liquid copolymer-drug mixture. Upon contact with the treatment area, the copolymer of the copolymer-drug mixture forms a gel. Thus, this invention also discloses compositions containing particles of the copolymer-drug mixture suspended in a pharmaceutically acceptable carrier, as well as compositions containing the copolymer and drug in combination with a pharmaceutically acceptable carrier. In yet a further embodiment, there are disclosed methods for topically delivering a drug to a treatment area by administering such a composition thereto.

In yet a further embodiment, a block or graft copolymer may be lightly cross-linked to form a hydrogel. Suitable graft copolymer hydrogels comprise a backbone bioadhesive or pH-sensitive polymer component with a pendent temperature-sensitive component grafted thereto, or a backbone temperature-sensitive component with a pendent bioadhesive or pH-sensitive component grafted thereto. In addition, block copolymer hydrogels are also disclosed comprising a bioadhesive or pH-sensitive polymer component joined to a temperature-sensitive polymer component. Such hydrogels may contain one or more pharmaceutically acceptable drugs in, for example, a dissolved or dispersed form.

In yet another embodiment, there is disclosed a graft copolymer in which both the backbone and pendant polymer components are temperature-sensitive polymer components. Such graft copolymers may also have a critical temperature ranging from 20° to 40° C. and are useful for the controlled release of therapeutic drugs.

In still another embodiment, a graft copolymer hydrogel in which both the backbone and pendant polymer components are pH-sensitive polymer components is disclosed. These hydrogels are also useful for the delivery of therapeutic drugs.

In a further embodiment, graft and block copolymers having photosensitive polymer components are disclosed. In these copolymers, photosensitive moieties are incorporated into the copolymer such that the copolymer undergoes light induced phase transition. Such copolymers are useful in therapeutic drug delivery.

In yet a further embodiment, there are disclosed pressure-sensitive copolymers useful in adhesive applications. The pressure-copolymers undergo amorphous (adhesive) to crystalline (non-adhesive) phase transitions as a function of temperature and as such as temperature-sensitive copolymers. These copolymers are graft copolymers having long carbon chain pendant polymer components.

Still a further aspect of this invention involves block or graft copolymers (including hydrogels of the same) for general industrial use, including, for example, use as lubricants, moisturizers, bulk-formers and/or absorbents. In this context of the present invention, the block and graft copolymers may used over a wide pH and temperature range.

Other aspects of the present invention will become evident upon reference to the attached figures and following detailed description. To this end, various references are noted herein which are hereby incorporated by reference in their entirety.

DETAILED DESCRIPTION OF THE INVENTION

Figure 1:
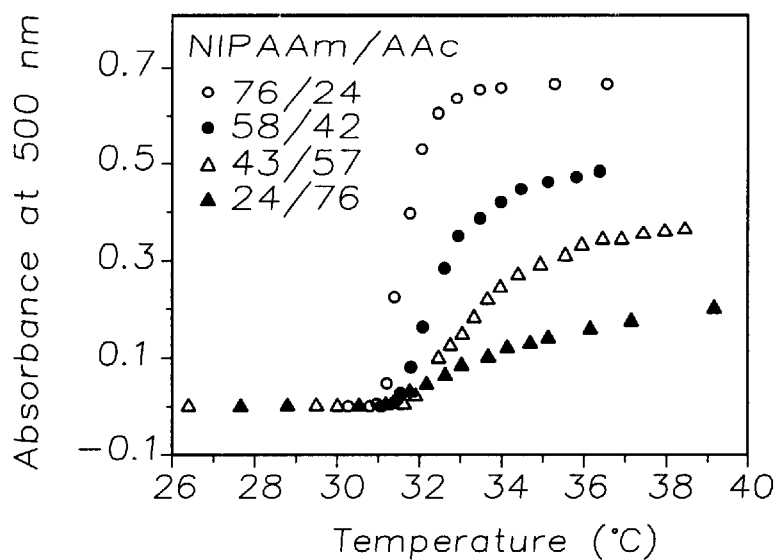
FIG. 1 illustrates the temperature-sensitive behavior of 0.2 weight percent solutions of four block copolymers of poly(N-isopropylacrylamide) and polyacrylic acid ("NIPAAm-b-AAc"), with varying ratios of poly(N-isopropylacrylamide) ("NIPAAm") and polyacrylic acid ("AAc"), in aqueous phosphate buffered saline solution (pH 7.4).

The present invention is generally directed to environmentally-sensitive block and graft copolymers, including hydrogels thereof. The environmentally-sensitive copolymers of this invention include pH-sensitive, temperature-sensitive, pressure-sensitive, photo-sensitive, solvent-sensitive, solvent concentration-sensitive, ion-sensitive and ionic strength-sensitive copolymers. Such copolymers are particularly effective in therapeutic drug delivery and, even more specifically, in the sustained and controlled release of a therapeutic drug, especially when the pH-sensitive component is bioadhesive (i.e., exhibits a prolonged residence time in contact with, for example, mucosal tissues). In this embodiment, the environmentally-sensitive block and graft copolymers and hydrogels of this invention may be physically mixed with one or more therapeutic drugs to form a copolymer-drug mixture. This mixture may then be administered as a solid particle (hereinafter referred to as a "copolymer-drug particle") to a treatment area by topical application. Alternatively, the environmentally-sensitive block and graft copolymers and hydrogels may be administered in the form of a liquid or suspension which, upon contact with the treatment area, forms a gel. As used herein, the term "treatment area" means any surface on or in an animal body suitable for topical application, including (but not limited to) the eye, an open wound or burn, and mucosal tissue (such as the respiratory and alimentary tracts and vagina), and which contains a sufficient water/ion content to hydrate the particle or gel upon contact.

More specifically, the copolymer-drug mixtures of the present invention may be administered to the treatment area in a composition wherein the copolymer-drug mixture is suspended as solid particles within a pharmaceutically acceptable carrier. The pharmaceutically acceptable carriers of this invention must not cause significant dissolution of, or drug release from, the copolymer-drug particles suspended therein. In one embodiment, the copolymer-drug particles may be suspended in a volatile carrier, such as a fluorocarbon propellant. Upon contact with the treatment area, such as the eye, the volatile propellant evaporates, leaving the particles on the surface of the eye. The particles then hydrate, swell, adhere to the mucosal tissue surface and slowly release the drug from the copolymer-drug particle as it undergoes swelling and dissolution. In another embodiment, the copolymer-drug particles may be suspended in a non-volatile carrier, such as distilled or sterile water. As described above, upon contact with the treatment area, the particles hydrate, swell, and release drug during particle swelling and dissolution. Alternatively, the copolymer may be dissolved in a pharmaceutically acceptable carrier in combination with the drug and administered in the form of a liquid copolymer-drug mixture, the copolymer component of which forms a gel upon contact with the treatment area. The physical changes which occur upon contact with the treatment area are discussed in greater detail below.

As used in the context of this invention, the term "drug" includes the definition set forth in 21 C.F.R. § 201(g)(1), "Federal Food, Drug and Cosmetic Act Requirements relating to Drugs for Human and Animal Use" (hereby incorporated by reference). Under this definition, a drug means (a) articles recognized in the official United States Pharmacopeia, official Homeopathic Pharmacopeia of the United States, or official National Formulary, or any supplement thereof; and (b) articles intended for use in the diagnosis, cure, mitigation, treatment, or prevention of disease in man or other animals; and (c) articles (other than food) intended to affect the structure or any function of the body of man or other animals; and (d) articles intended for use as a component of any articles specified in clause (a), (b) or (c) above; but does not include devices or their components, parts or accessories. Water is specifically intended to be included in the definition of the term drug as used herein. The term "cosmetic composition" includes compositions for skin care, hair care, care of nails, and toiletries, perfumes and fragrances. The term "superabsorbent" means a hydrogel which, starting from a dry material, will imbibe about 20 times its own weight of aqueous fluid (J. Gross, Absorbent Polymer Technology, L. Brannon-Peppas and R. Harland, ed., Elsevier, New York, N.Y. 1990, page 9).

As mentioned above, in the practice of one embodiment of this invention, block and graft copolymers are used as a vehicle for the delivery of one or more drugs. The graft and block copolymers and hydrogels accomplish controlled and sustained drug release from the copolymer-drug mixtures through the physical properties of the component parts of the copolymer. Specifically, the block and graft copolymers of the present invention are comprised of polymer components individually selected from, for example, a temperature-sensitive polymer component, a pH-sensitive polymer component, a pressure-sensitive polymer component, a photo-sensitive polymer component, a solvent-sensitive polymer component, a solvent concentration-sensitive polymer component, an ion-sensitive polymer component and an ionic strength-sensitive polymer component. For copolymers containing a temperature-sensitive polymer component, upon contact with the treatment area, the pH-sensitive polymer component of the graft and block copolymers or hydrogels either hydrate and swell, or collapse, thereby causing release of the drug from the copolymer-drug mixtures. Hydration and swelling of the pH-sensitive polymer component is due to the uptake of both water and ions from the treatment area. For example, when the pH-sensitive polymer component is a carboxylic acid-containing polymer (such as polyAAc), the carboxylic acid groups ("COOH") are ionized by the uptake of cations (such as $Na^+$ or $K^+$) from the treatment area to yield neutralized carboxylic acid moieties (i.e., $COO^-Na^+$). Ionization of the carboxylic acid groups is accompanied by the uptake of water which, in turn, results in the swelling and gelling of the copolymer-drug mixtures. In addition, such hydration and swelling causes the pH-sensitive polymer component to adhere to the tissue of the treatment area (i.e., to become bioadhesive). In contrast to the pH-sensitive polymer component, the temperature-sensitive polymer component resists the hydration and swelling of the copolymer-drug mixture, thereby resulting in the sustained and controlled release of the drug from the copolymer-drug mixture. Photo-sensitive polymer components undergo phase transitions induced by light, while pressure-sensitive polymer components undergo phase transitions induce by pressure. Similarly, polymer components of this invention also include polymer components which undergo a phase transition in response to ions or ionic strength, as well as those which undergo a phase transition in response to solvent or solvent concentration.

As used herein, a "block copolymer" of the present invention has at least one of the above-described polymer components terminally linked to another polymer component. For example, a block copolymer may comprise a temperature-sensitive polymer component terminally linked to at least one pH-sensitive polymer component (i.e., an end-to-end link). Similarly, a "graft copolymer" of the present invention has one of the above-described polymer components as a backbone polymer and at least another polymer component as a pendant polymer. A graft copolymer may have, for example, a pH-sensitive polymer component as a backbone polymer and at least one temperature-sensitive polymer component as a pendant polymer, or a temperature-sensitive polymer component as a backbone polymer and at least one pH-sensitive polymer component as a pendant polymer.

For purpose of clarity, a short review of polymer nomenclature would be helpful in understanding this invention. In general, a polymer is a macromolecule (i.e., a molecular chain) derived from the polymerization of monomer units. The links of the molecular chain are the monomer units. For example, polyacrylic acid (polyAAc) is a polymer derived from the monomer acrylic acid (AAc). More specifically, polyAAc is a "homopolymer," a polymer consisting of a single repeating unit, namely, AAc. In contrast, the polymers of the present invention are "copolymers." A copolymer is a polymer containing two (or more) different monomer units. A copolymer may generally be synthesized in several ways. For example, a copolymer may be prepared by the copolymerization of two different monomers. Such a process yields a copolymer where the two different monomers, commonly referred to as "comonomers," may be randomly distributed throughout the polymer chain. These copolymers are known as "random copolymers." Alternatively, copolymers may be prepared by the covalent coupling or joining of two homopolymers. For example, the covalent coupling of one homopolymer o the terminus of a second, different homopolymer provides a "block copolymer". A lock copolymer containing homopolymer A and homopolymer B may be schematically represented by the following formula:

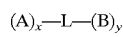

where $(A)_x$ is a homopolymer of x monomers of A, $(B)_y$ is a homopolymer consisting of y monomers of B, and L is a suitable covalent bond.

Depending upon the chemical nature of the homopolymer components, an additional type of copolymer may also be prepared. For example, as mentioned above, polyAAc is a homopolymer of AAc moieties. Consequently, the polyAAc polymer chain is substituted with pendant carboxylic acid groups. The covalent coupling of a second, different homopolymer to one or more of these pendant carboxylic acid groups provides a "graft copolymer." Essentially, the second polymer is grafted onto the first. Thus, graft copolymers have a "backbone" polymer onto which one or more "pendant" polymers have been covalently attached. The nature of the graft copolymer may vary considerably depending upon the degree of substitution of the pendant polymers onto the backbone polymer. A graft copolymer having backbone homopolymer A onto which pendant homopolymer B is attached may be schematically represented by the following formula:

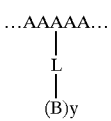

where " . . . AAAAA . . . " is a homopolymer of monomer A, $(B)_y$ is a homopolymer of y monomers of B, and L is a suitable covalent bond.

The block and graft copolymers discussed above contain homopolymers A and B, which represent the temperature-sensitive polymer components, pH-sensitive polymer components, photo-sensitive polymer components, pressure-sensitive polymer components, ion-sensitive polymer components, ionic strength-sensitive polymer components, solvent-sensitive polymer components and/or solvent concentration-sensitive polymer components of this invention. In addition, the block and graft copolymers of this invention may also be derived from polymers other than homopolymers. For example, rather than grafting pendant homopolymer B to backbone homopolymer A, copolymer CD may be grafted to homopolymer backbone A to yield a graft copolymer where the pendant polymer is itself a copolymer. In such a case, homopolymer A may correspond to a pH-sensitive polymer component and copolymer CD is either a random copolymer or a block copolymer of comonomers C and D, and may correspond to a temperature-sensitive copolymer component. Alternatively, the backbone polymer may be the copolymer CD (which represents, for example, a temperature-sensitive polymer component), with the pendant polymer being the homopolymer A (which represents, for example, a pH-sensitive polymer component). The same is true for block copolymers—that is, copolymer CD (which represents, for example, a temperature-sensitive polymer component) may be used in combination with homopolymer A (which represents, for example, a pH-sensitive polymer component). While the pH-sensitive polymer component has generally been referred to as a homopolymer in the above discussion, the pH-sensitive polymer component may itself be a copolymer subject to certain limitations which are discussed in greater detail below. The same is true for the other polymer components of this invention.

Figure 3:
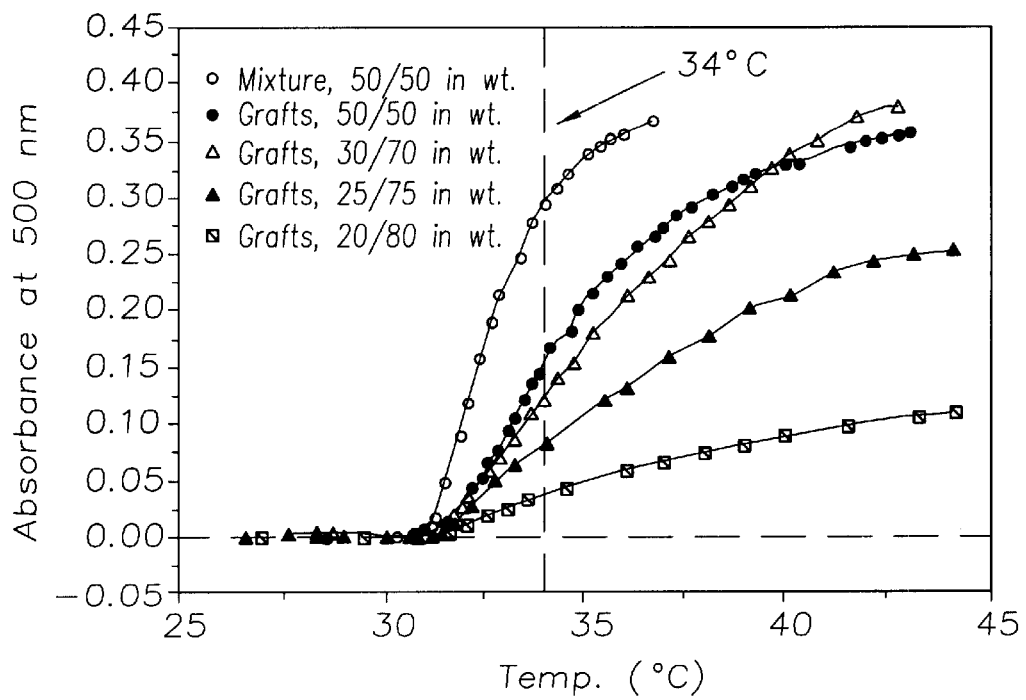
FIG. 3 illustrates the temperature-sensitive behavior of 0.2 weight percent solutions of four graft copolymers of NIPAAm-g-AAc with varying ratios of NIPAAm/AAc in aqueous phosphate buffered saline solution (pH 7.4), as well as a 50/50 physical mixture of the same.

In the practice of this invention in the context of drug delivery, it is advantageous that the graft and block copolymers, and hydrogels thereof, have a critical temperature ranging from room temperature to near physiological temperature. In one embodiment, the copolmers and hydrogels of this invention undergo solution-to-gel phase transition at a temperature ranging from room temperature to just above physiological temperature. The solution-to-gel or precipitation phase transition (referred to herein as the "lower critical solution temperature" or "LCST") may be determined by absorbance spectroscopy by measuring the optical density of the block and graft copolymers in solution at a specific wavelength (such as 500 nm) as a function of temperature (Chen et al., *Biomaterials* 11:625–36, 1990). On warming to its LCST, the block and graft copolymers begin to aggregate, and the transmission of light decreases. The cloud point of a copolymer solution is defined as the temperature at which the solution has reached a certain value of its maximum opacity (such as 50%). (The determination of the LCST of several representative block and graft copolymer solutions of the present invention are provided in FIG. 1, Example 1B, and in FIG. 3, Example 2B, respectively.) Alternatively, the phase transition temperature may be determined by measuring the change in viscosity as a function of temperature. Upon warming to the LCST, the viscosity of a block or graft copolymer solution-significantly increases as it undergoes the liquid-to-gel phase transition. This phase transition may be defined as the temperature at which the solution reaches a certain percent (such as 25%) of its maximum viscosity. Such viscosity measurements are preferred when the opacity of a copolymer solution does not significantly change when reaching the liquid-to-gel phase transition temperature. Other indicators of the phase transition include measuring the swell or collapse of the block or graft copolymer.

In one embodiment, the block and graft copolymers of the present have LCSTs (at a pH between 4.0 to 8.0) in the range from 20° C. to 40° C. Depending upon the desired end use, the LCST may range from 26° C. to 34° C., or from 28° C. to 32° C. With regard to vaginal use, the LCST is preferably about 36° C. Preferably, the block and graft copolymers have the above LCSTs at a pH within the range from 6.0 to 8.0, more preferably from 7.0 to 7.8, and most preferably at a physiological pH of 7.4. In the context of this invention, the LCSTs of the block and graft copolymers are measured at an aqueous solution concentration generally below 10% by weight. It should also be understood that determination of the LCST within the above pH range does not exclude use of the block and graft copolymers at physiological conditions which may present higher or lower pHs. For example, very low pHs (pH 1) are encountered in the stomach, and the block and graft copolymers of this invention are suitable for oral administration thereto. Moreover, for industrial uses, a pH in excess of 8 may be encountered.

In the context of drug delivery, block and graft copolymers with LCSTs outside of the 20° C. to 40° C. range are generally not suitable for use in the practice of this invention. Copolymers with LCSTs below 20° C., in addition to being difficult to administer, are extremely resistant to dissolution at room temperature and therefore are ineffective in drug delivery. Copolymers with LCSTs above 40° C. will rapidly and completely dissolve at physiological temperature and pH, and therefore are ineffective in retarding drug delivery as a consequence of short residence period at the treatment area. (This aspect of the invention. is discussed in greater detail below with regard to the bioadhesive properties of the block and graft copolymers of this invention.)

As mentioned above, the temperature-sensitive polymer component of the block and graft copolymers of this invention may be derived from homopolymers or copolymers. In either case, the temperature-sensitive polymer component has a LCST in the same range as that of the block and graft copolymers of this invention (i.e., for use as a drug delivery vehicle, in the range from 20° C. to 40° C., preferably in the range from 26° C. to 34° C., and more preferably from 28° C. to 32° C. within the above-identified pH ranges). Thus, for drug delivery use, suitable temperature-sensitive polymers of this invention have LCSTs ranging from 20° C. to 40° C., and confer an LCST of the same range upon their respective block and graft copolymers. In the context of this invention, the LCSTs of the temperature-sensitive polymers are measured at an aqueous solution concentration below 1% by weight, preferably from 0.01% to 0.5% by weight, and more preferably from 0.1% to 0.3% by weight.

Temperature-sensitive polymers of this invention may contain ester, urethane, ether, amide, alcohol, amine and acid groups. These polymers may be synthesized by the polymerization of vinyl monomers such as acrylamide or N-isopropylacrylamide which yield polyacrylamide and poly(N-isopropylacrylamide), respectively. Similarly, polymerization of cyclic ether monomers such as ethylene oxide provide polyethers and polymerization of vinyl acetate followed by hydrolysis provides polyalcohols. Suitable esters include esters of acrylic acid and its various derivatives such as methacrylic acid. Suitable ethers include ethylene oxide, propylene oxide, and vinyl methyl ether. Suitable alcohols include hydroxypropyl acrylate. Suitable amides include N-substituted acrylamides, N-vinylacetamide, N-vinyl proprionamide, and N-vinylbutyramide. Thus, block and graft copolymers of the present invention include temperature-sensitive polymer components containing polyesters, polyethers, polyalcohols, and polyamides. Preferably, the temperature-sensitive polymer components are selected from block copolymers of polyethylene oxide and polypropylene oxide; random copolymers of ethylene oxide and propylene oxide; polyvinyl methyl ether, polyhydroxypropyl acrylate, polyvinyl alcohol derivatives, poly(N-substituted)acrylamides, poly(N-vinylpyrrolidine), and poly(N-vinylpiperidine). Preferred temperature-sensitive polymers include poly(N-substituted acrylamides) and poly(N-substituted methacrylamides) 'such as poly(methacrylic acid). These polyacrylamides may be derived from either unsubstituted or mono- or di-N-substituted acrylamides. The N-substituents of these acrylamides may be alkyl, C2–C10; cycloalkyl, C3–C6; or alkoxyalkyl, C2–C10. The disubstituted acrylamides may be cycloamides such as cyclopentyl and cyclohexyl amide derivatives or lactams such as caprolactam. In a preferred embodiment, the temperature-sensitive polymer component is poly(N-alkyl substituted)

acrylamide. (The synthesis and properties of a representative temperature-sensitive homopolymer, poly-N-isopropylacrylamide (NIPAAm), is described in detail in Example 1A1.)

The temperature-sensitive polymers include polymers containing ether groups such as poly(ethylene oxide) (PEO), poly(ethyleneoxide)/poly(propylene oxide) random copolymers (polyPEO/PPO), PEO-PPO-PEO triblock surfactants, alkyl-PEO block surfactants, and poly(vinyl methyl ether); alcohol groups such as hydroxypropyl acrylate, hydroxypropyl methylcellulose, hydroxypropyl cellulose, hydroxyethyl cellulose, methylcellulose, and poly(vinyl alcohol) derivatives; and substituted amide groups such as poly(N-substituted acrylamides), poly(N-acryloyl pyrrolidine), poly (N-acryloyl piperidine), and poly(acryl-L-amino acid amides).

Alternatively, the temperature-sensitive polymers may be naturally occurring polymers (e.g, cellulose and its derivatives) which may be chemically modified to provide derivatives which possess the temperature-sensitive behavior required for the practice of the present invention. Suitable naturally occurring polymers include cellulose and its derivatives such as hydroxyethylcellulose, methylcellulose, hydroxypropyl cellulose, and hydroxypropyl methylcellulose. Such cellulosic polymers may also be derivativzed (e.g., with alkyl acids or alcohols) to lower the LCST into the desired range (see, e.g., Nightingale, Grishin and Hoffman, 13th *Annual Meetiniz of the Society for Biomaterials*, New York, N.Y. Jun. 2–6, 1987).

In one embodiment, the temperature-sensitive polymer component is a homopolymer made by the polymerization of one of the above monomers. Alternatively, the temperature-sensitive polymer component is a random or block copolymer. Suitable temperature-sensitive copolymers include (but are not limited to) copolymers derived from the polymerization of hydroxypropyl acrylate and acrylamide or hydroxyethyl acrylate; hydroxyethyl acrylate and diacetone acrylamide or N-isopropyl acrylamide; N-isopropyl acrylamide and methacrylamide or methylacrylate or butyl methacrylate; vinyl acetate and vinyl butyrate; and vinyl acetate and vinyl pyrrolidine. For both homopolymer and copolymer temperature-sensitive polymer components, their LCST may be between 20° C. and 40° C., and may confer an LCST to the resulting block and graft copolymers within the same range. (The synthesis of a representative temperature-sensitive copolymer, copoly(N-isopropylacrylamide-butylmethacrylate (NIPAAm-BMA), is described in detail in Example 3A1.) In a preferred embodiment, the temperature-sensitive polymer component is a two block copolymer of polyethylene oxide and polypropylene oxide. Such two-block copolymers are also known as poloxamers, and are commercially available from BASF-Wyandotte Corp. (Wyandotte, Mich.) under the tradename Pluronics®, and have the general formula $HO(CH_2CH_2O)_a(CH_2CH(CH_3)O)_b(CH_2CH_2O)_aH$ where b is at least 15 and $(CH_2CH_2O)_{2a}$ is varied from 20–90% by weight. (The synthesis and properties of representative copolymers having various Pluronics® grafted to polyAAc are described in detail in Example 6).

In another embodiment, the temperature-sensitive polymer component is a crystallizable polymer component. Suitable crystallizable polymer components are polymers (or copolymers) that, when incorporated into either the block or graft copolymer or hydrogels of this invention, cause the copolymer or hydrogel to undergo a crystalline to amorphous phase transition (i.e., melting or Tm) at either above or below physiological temperature. These copolymers are adhesive in the amorphous state and non-adhesive in the crystalline state and are useful as adhesives in a variety of medical and industrial applications. Such adhesive copolymers are commonly referred to as "pressure-sensitive" copolymers. In this embodiment, suitable copolymers and hydrogels of this invention include, but are not limited to, those having a Tm ranging from 20° C. to 40° C.

Suitable crystallizable polymers include polymers having aliphatic or aromatic groups, or a combination of aliphatic and aromatic groups. Preferred aliphatic groups include linear carbon chains having at least 10 carbon atoms, fluorinated aliphatic groups having at least 6 carbon atoms, and aralkyl groups where the alkyl group has between 10 and 24 carbon atoms. These polymers may be derived from their corresponding monomers. Crystallizable polymers containing aliphatic groups may be prepared from monomers including C14 to C22 acrylates or methacylates, acrylamides or methacrylamides, vinyl ethers or esters, siloxanes or alpha olefins. Crystallizable polymers containing aromatic groups may be prepared from p-alkyl stryrene where the alkyl group is preferably a C10 to C24 group.

In addition to the aliphatic and aromatic group containing crystallizable polymers mentioned above, other suitable crystallizable polymers include relatively polar polymer components. Examples of polar and crystallizable polymers include polyoxyalkylene polymer components such as polyoxyethylene, polyoxypropylene, and polyoxybutylene polymer components. These relatively polar crystallizable polymer components improve the adhesive properties of the crystallizable polymer component containing copolymer.

In another embodiment, the temperature-sensitive polymer component is a polymer component having a glass transition temperature (Tg) near physiological temperature, such as just below physiological temperature. In this case, when the polymer component is warmed and passes through its Tg, its properties change from a rigid, glass-like matrix to a soft, rubbery matrix. This transition usually occurs over a narrow temperature range of 1–2° C. When a drug is loaded into such rubbery regions at temperature above Tg (T>Tg), and then cooled to a temperature below Tg (T<Tg), the drug is trapped in the glassy region and will not leak out. Then, when the resulting copolymer is then applied by, for example, topical application, the temperature of the copolymer will rise above Tg and the drug will be able to diffuse out of the copolyme. The Tg of polymer component may be readily controlled by appropriate choices of comonomers by those skilled in this field. In this embodiment, suitable copolymers and hyrogels of this invention include, but are not limited to, those having a Tg ranging from 20° C. to 40° C.

In still a further embodiment, the temperature-sensitive polymer component may undergo a phase transition due to a conformational change which leads to gelling, such as thermally-induced gelling associated with a helix- coil or helix-helix transition.

As mentioned above, the pH-sensitive polymer component of the graft and block copolymers of the present invention drives dissolution, as well as imparting bioadhesive properties and, in some instances, drug binding characteristics to the block and graft copolymer. As used herein, the term "bioadhesive" refers to the ability of the copolymer-drug mixture to adhere to the tissue of the treatment area upon hydration and swelling of the mixture. For example, when the treatment area is the eye, adhesion between the copolymer-drug mixture and the surface of the eye is due to the attractive interaction between chemical functional groups of the copolymer and the eye surface. The ionic nature and high molecular weight of the pH-sensitive polymer component provides an adhesive interaction with the surface of the eye, thereby prolonging the residence time of the copolymer-drug mixture on the eye's surface.

In one embodiment, the pH-sensitive polymer component is a synthetic carboxylic acid-containing polymer, and may be derived from polymerizable carboxylic acids, including acrylic acid, methacrylic acid, ethacrylic acid, β-methylacrylic acid, cis-α-methylcrotonic acid, trans-α-methylcrotonic acid, α-butylcrotonic acid, α-phenylacrylic acid, α-benzylacrylic acid, α-cyclohexylacrylic acid, β-phenylacrylic acid, coumaric acid, and umbellic acid, or any combination thereof. Carboxymethylcellulose may also be a suitable carboxylic acid-containing polymer. In a preferred embodiment, the carboxylic acid-containing polymer is polyAAc.

In another embodiment, the pH-sensitive polymer component is a naturally occurring polymer such as a polysaccharide, peptide and/or protein, or any combination thereof. Examples of suitable polysaccharide pH-sensitive polymer components include polysaccharides with carboxylic acid groups such as carboxymethyl cellulose, hyaluronic acid, and alginic acid. Other suitable polysaccharides include polysaccharides with sulfate and/or sulfonamide groups such as heparin, chondroitin sulfate, carrageenan, and dextran sulfate; and polysaccharides with amino groups such as chitosan. Examples of suitable proteins include collagen, albumin, and casein. Suitable polypeptides include polylysine, polyglutamic acid, and polyaspartic acid.

In another embodiment, the pH-sensitive polymer component is an amine-containing, a phosphate-containing, a sulfate-containing, or a sulfonate-containing polymer component, or mixtures thereof. In a preferred embodiment, the pH-sensitive polymer component is an amine-containing or a phosphate-containing polymer component.

As described above, the pH-sensitive polymer component imparts bioadhesion to the block and graft copolymers of the present invention. In the case of carboxylic acid-containing polymer components, on contact with a treatment area, such as the eye or other mucosal tissue, the carboxylic acid moieties ionize and become carboxylate salts, for example, sodium carboxylate or potassium carboxylate. The transformation from carboxylic acid to carboxylate salt upon contact with the treatment areas results in hydration of the copolymer-drug mixtures. The bioadhesive properties of the mixtures are imparted upon hydration. Prior to hydration, the carboxylic acid form may also be bioadhesive. Ionization to the carboxylate salt causes the gel to swell and act "sticky", but it may lose its stickiness as it further hydrates. Similarly, the amine-phosphate-, sulfate-, and sulfonate-containing polymer components are also capable of ionizing and swelling upon contact with the treatment area. Specifically, ions present in the treatment area are taken up by these pH-sensitive polymer components to neutralize the ionizable moieties thereof Ionization in turn is accompanied by water uptake, which causes the pH-sensitive polymer component, and thus the copolymer-drug mixture, to swell and become gel-like, viscous, tacky and bioadhesive.

In a preferred embodiment, the pH-sensitive polymer component is a homopolymer (e.g., polyAAc). In a further embodiment, the pH-sensitive polymer component may be a copolymer derived from the copolymerization of two pH-sensitive monomers (e.g., acrylic acid and methacrylic acid), or a pH-sensitive monomer and a non-pH-sensitive monomer. In either case, the content of the comonomer (i.e., the non-pH-sensitive monomer or the different pH-sensitive monomer) must not be so great as to eliminate the bioadhesiveness of the pH-sensitive polymer component. In other words, the pH-sensitive polymer component should consist essentially of a single repeating monomer unit, with other monomer units present to an extent which does not significantly diminish the bioadhesive properties of the pH-sensitive polymer component. Typically, a single pH-sensitive polymer component will comprise in excess of 90% of the same pH-sensitive monomer, preferably in excess of 95%, and more preferably in excess of 99%, and typically have a molecular weight in excess of 50,000.

In addition to imparting bioadhesiveness to the block and graft copolymer, hydration of the pH-sensitive polymer component also causes the block and graft copolymer to swell, which leads to the ultimate dissolution of the copolymer-drug mixtures. Swelling and dissolution in turn lead to drug release. For the block and graft copolymers of the present invention, their rate of swelling and dissolution or erosion rate is controlled by the resistance of temperature-sensitive polymer component to the swelling, which is being driven by the ionization of the pH-sensitive polymer component.

The pH-sensitive polymer component of the block and graft copolymers of the present invention may also optionally bind the therapeutic drug via ionic interactions. For example, for therapeutic drugs which are cationic (i.e., positively charged), the anionic nature of the pH-sensitive polymer component (such as a carboxylic acid-containing polymer component) may ionically bind a cationic drug. (Such an interaction is described in Example IC for timolol-hydrogen maleate, a cationic therapeutic drug, and anionic polymer component, polyAAc, of block copolymer NIPAAc-b-AAc.) Furthermore, as the drug is released by ion exchange, the part of the pH-sensitive polymer component which had bound the drug becomes available to enhance the bioadhesion to the mucosal tissue.

In another embodiment, the environmentally-sensitive copolymers of the present invention contain a photosensitive polymer component. Photo-sensitive polymer components cause light induced phase transitions of the copolymer. These photo-sensitive polymer components typically contain photosensitive moieties (ie., light sensitive chromophores) covalently attached to the polymer and which absorb light and induce phase transitions. Depending upon the absorbance properties of the photosensitive moiety, these phase transitions may be induced by either ultraviolet or visible light.

Suitable photosensitive moieties include chlorophyllin, azo dyes such as azobenzene and azonaphthalene and their derivatives, and pararosaniline, and are generally known in the art (see. e.g., Irie, *Adv. Polym. Sci.* 94:28, 1990; Lohmann and Petrak, *CRC Crit. Rev. in Therapeutic Drug Carrier Systems* 5:263, 1989; Kungwatchakun et al. *Makromol. Chem. Rapid Commun.* 9:243–246, 1988; Ishihara et al., *J. Polym. Sci. Polym. Chem. Ed.*, 22:121–128, 1984; Tirrell, *J. Controlled Release* 6:15–21, 1987; and Okahata et al. *J. Chem. Soc. Perkin Trans.* II:1003, 1987).

In a further embodiment, the environmentally-sensitive copolymers of this invention contain a pressure-sensitive polymer component. Pressure-sensitive polymer components are known in the art (see, e.g., Miyata et al., *J. Appl. Polymer Sci.* 56:1615–1623, 1995; Satas, *Handbook of Pressure Sensitive Adhesives Technology*, Van Nostrand Reinhold Co., Inc., 1982; Flanagan, *Handbook of Adhesive Bonding*, McGraw-Hill, 1973; Landrock, *Adhesive Technology Handbook*, Noyes Publications, 1985; Miyauchi, *J. Polymer Sci.: Polymer Chem. Edition* 19:1871–1873, 1981; Clarke et al, *Adhesive Age*, Sep. 39–41, 1993).

Similarly, ion-sensitive, ionic strength-sensitive, solvent-sensitive and solvent concentration-sensitive polymer components of this invention are also known in the art. For example, representative examples of solvent-sensitive polymer components include, for example, those disclose by Hirokawa and Tanaka. *J. Chem. Phys.* 81(12):Part II, 1984. Similarly, representative examples of ion-sensitive polymer components include those disclosed by Ricka and Tanaka, *Macromolecules* 181:83, 1985, and phase transitions caused by polymer complexation are disclosed by Yu et al., J. Chem. Phys. 97(10), 1992.

The copolymer-drug mixtures of this invention may be prepared by incorporation of the drug into the block or graft copolymer or hydrogel by physical entrapment, and/or by ionic interaction with the pH-sensitive polymer component of the block or graft copolymer or hydrogel. This may be accomplished by dissolving the block or graft copolymer or hydrogel in a solution containing the drug, and then precipitating the copolymer-drug solution into a non-solvent for the copolymer and drug, thus obtaining the copolymer-drug particles. (For example, the formation of particles of the drug timolol-hydrogen maleate and the copolymer NIPAAm-b-AAc is described in Example IC.) Alternatively, the block or graft copolymer or hydrogel may be dissolved in a solution containing the drug, or dissolved in a solution to which the drug is then added, to yield a liquid copolymer-drug mixture. Such a solution may be further concentrated, or may be dried (and cooled for a Tg-sensitive copolymer) to yield, for example, a solid film. Suitable solutions, include both aqueous and non-aqueous solvents. In one embodiment, the solution may contain at least 10% by weight of a non-aqueous solvent, and in a further embodiment may contain at least 99% by weight of a non-aqueous solvent.

As for the synthesis of the block and graft copolymers, such polymers may generally be synthesized by, for example, covalent coupling of a suitably reactive temperature-sensitive polymer component to a suitably reactive pH-sensitive polymer component. The covalent link between the two polymer components should be resistant to cleavage under conditions encountered following topical administration. Accordingly, suitable covalent linkages include amide, ester, ether, thioester, thioether, urea, urethane and amine linkages. Such linkages result from the coupling of a suitably reactive temperature-sensitive polymer component with a complementary pH-sensitive polymer component. For example, an amide linkage may be prepared either by coupling an amino-terminated temperature-sensitive polymer component with a carboxylic acid-modified pH-sensitive polymer component, or by the coupling of an amino-terminated pH-sensitive polymer component with a carboxylic acid-terminated temperature-sensitive polymer component. Other linkages may be similarly prepared by standard techniques. For example, representative syntheses of an amino-terminated pH-sensitive polymer (polyAAc) and a carboxylic acid-modified temperature-sensitive polymer (NIPAAm) are described in detail in Example 1A1 and 1A2, respectively. The coupling of these species to provide an amide-linked block copolymer is described in Example 1A3. A representative synthesis of an amino-terminated temperature-sensitive polymer component and its covalent coupling to a carboxylic acid-modified pH-sensitive polymer component to yield an amide4inked graft copolymer is described in Example 2A2.

Alternatively, graft copolymers of the present invention may be synthesized by, for example, the copolymerization of a suitable pH-sensitive monomer with a temperature-sensitive macromonomer. A representative synthesis of such a graft copolymer is described in detail in Example 2A1.

In one embodiment, the copolymers of the present invention are block copolymers. As mentioned above, in one embodiment, the block copolymers of this invention comprise a first environmentally-sensitive polymer component joined to a second environmentally-sensitive polymer component. In one embodiment, the first and second polymer components are each responsive to a different environmental trigger. In another embodiment, environmentally-sensitive polymer components are responsive to the same environmental trigger, but to different degrss or threshold conditions. For example, both of the polymer components may be responsive to a thermal trigger or a pH trigger, but with the two components each responsive to a different temperature or pH, respectively.

Block copolymers may be synthesized by, for example, the covalent coupling of the terminus of a pH-sensitive polymer component to the terminus of a temperature-sensitive polymer component. The covalent linkage may be any one of the above-mentioned linkages, and in a preferred embodiment, the linkage is an amide linkage. The block copolymer may be prepared by the coupling of two homopolymers (e.g., a pH-sensitive homopolymer and a temperature-sensitive homopolymer), a homopolymer and a copolymer (e.g., a pH-sensitive homopolymer and a temperature-sensitive copolymer or a pH-sensitive copolymer and a temperature-sensitive homopolymer), or two copolymers (e.g., a pH-sensitive copolymer and a temperature-sensitive copolymer). A representative example of a block copolymer derived from the coupling of two homopolymers is described in Example 1.

In the context of drug delivery, suitable block copolymers of the present invention exhibit an LCST between 20° C. and 40° C. (at a pH with the range from 4 to 8), and are derived from temperature-sensitive polymer components having an LCST between 20° C. and 40° C. The block copolymers of the present invention preferably have an average molecular weight in the range from 5,000 to 100,000 (and may go as high as 500,000), and the temperature-sensitive polymer component preferably constitutes at least 10%–20% by weight of the block copolymer. In a preferred embodiment, the pH-sensitive polymer component has a relatively high molecular weight (e.g., in excess of 50,000).

In another embodiment, the copolymers of the present invention are graft copolymers. As mentioned above, in one embodiment, the graft copolymers of this invention comprise a first environmentally-sensitive polymer component grafted to a second environmentally-sensitive polymer component. In one embodiment, the first and second polymer components are each responsive to different triggers. In another embodiment, environmentally-sensitive polymer components are responsive to different values of the same trigger. For example, the polymer components may be responsive to a thermal trigger or a pH trigger. A representative preparation of a graft copolymer having a temperature-sensitive backbone polymer component and a temperature-sensitive pendant polymer component is described in Example 7.

Graft copolymers are synthesized by, for example, the covalent coupling of a suitably reactive polymer, such as a pH-sensitive polymer component or a temperature-sensitive polymer component, to the pendant group of a backbone polymer, such as a temperature-sensitive polymer component or a pH-sensitive polymer component. The covalent linkage may be any one of the above-mentioned linkages, and in a preferred embodiment the linkage is an amide linkage. The graft copolymer may be prepared by the coupling of two homopolymers (e.g., a pH-sensitive homopolymer and a temperature-sensitive homopolymer), a homopolymer and a copolymer (e.g., a pH-sensitive homopolymer and a temperature-sensitive copolymer or a pH-sensitive copolymer and a temperature-sensitive homopolymer), or two copolymers (e.g., a pH-sensitive copolymer and a temperature-sensitive copolymer). As discussed above, the temperature-sensitive polymer component of the graft copolymers of the present invention may be a block or random copolymer, provided that, in the context of drug delivery, the copolymer has an appropriate LCST. Similarly, the pH-sensitive polymer component is preferably a homopolymer, although block or random copolymers may be used to provide the bioadhesiveness of the pH-sensitive polymer-component is not significantly diminished. In a preferred embodiment, the graft copolymer has a pH-sensitive homopolymer backbone with pendant temperature-sensitive polymer components. A representative synthesis of a graft copolymer derived from the coupling of two homopolymers is described in Example 2, and a representative synthesis of a graft copolymer derived from the coupling of a pendant temperature-sensitive copolymer to a pH-sensitive homopolymer backbone is presented in Example 3. In a preferred embodiment, the graft copolymer has a pH-sensitive homopolymer backbone of polyAAc with pendant temperature-sensitive Pluronics® (i.e., two-block copolymers of ethylene oxide and propylene oxide) grafted thereto, as disclosed in Example 6.

In one embodiment, the graft copolymers of the present invention have either a pH-sensitive polymer backbone with one or more pendant temperature-sensitive polymer components, or a temperature-sensitive polymer backbone with one or more pendant pH-sensitive polymer components. In another embodiment, the graft copolymers may contain a temperature-sensitive backbone and pendant polymer components, or a pH-sensitive backbone and pendant polymer components. The degree of substitution of the pendant polymer components on the backbone polymer may be controlled by the chemical coupling reaction. For example, by adjusting the ratio of pendant groups to be reacted with the backbone polymer, the properties of the graft copolymer product may be controlled and optimized. This is particularly useful with natural, pH-sensitive polymer components such as proteins and polysaccharides. Graft copolymers with higher ratios of temperature-sensitive polymer components will possess relatively slower dissolution rates. Accordingly, a balance in the pH-sensitive and temperature-sensitive polymer components may provide an optimum copolymer which exhibits both preferred temperature-sensitive behavior with respect to dissolution and drug release, as well as preferred bioadhesion so as to provide extended residence time upon administration.

The graft copolymers of the present invention preferably have average molecular weights in the range from 100,000 to 600,000, and more preferably in the range from 250,000 to 500,000. In an alternative embodiment, the graft copolymers of this invention may have average molecular weights in the range from 50,000 to 1,000,000. In addition, the temperature-sensitive polymer component preferably constitutes at least 5%–10% by weight of the graft copolymer.

In a further embodiment of the present invention, the block and graft copolymers may be lightly cross-linked. These block and graft copolymers are referred to as "hydrogels." As mentioned above, in one embodiment, the block and graft copolymer hydrogels of this invention comprise a first and a second environmentally-sensitive polymer component. In one embodiment, the first and second polymer components are each responsive to the different triggers. In another embodiment, the environmentally-sensitive polymer components are responsive to the same trigger. For example, the polymer components may be responsive to a thermal trigger or a pH trigger. The preparation of a representative graft copolymer hydrogel having a pH-sensitive backbone polymer component and a pH-sensitive pendant polymer component is described in Example 8.

In one embodiment, the backbone polymer component is a cross-linked pH-sensitive polymer component with one or more pendant temperature-sensitive polymer components. In a preferred embodiment, the hydrogel is derived from a cross-linked pH-sensitive polymer backbone. Alternatively, the pH-sensitive polymer components of a block copolymer may be lightly cross-linked. Suitable cross-linking agents are well known and include (but not limited to) relatively "short" cross-linkers, such as methylene-bis-acrylamide and ethylene glycol dimethacrylate (EGDMA), as well as relative "long" cross-linkers, such as polyethylene glycol dimethacrylate (PEGDMA).

The cross-linked hydrogels of the block and graft copolymers effectively prevent rapid dissolution of the copolymer, while at the same time do not preclude copolymer gelling. In some embodiments, it may be preferred that the crosslink density is sufficiently light that the hydrogels are soluble or erodible. In other embodiments, it may be preferred that the crosslink density is sufficiently great that the gel is a permanent "chemical gel" with a permanent three dimensional polymeric network, which maintains its structure and is not soluble or erodible. The level of crosslinking in a hydrogel is typically estimated by reporting the ratio of the molarity of crosslinker in solution to the molarity of monomer. However, since an actual crosslink is only formed when the crosslinker molecule links to two different polymer chains, the number of actual crosslinks may be a fraction of the number of crosslinker monomers present in the gel network. The hydrogels of the present invention are lightly cross-linked, and contain preferably from 0.001%–10% by weight of the crosslinkers. The level of actual crosslinking resulting from these crosslinker molecules is believed to be from 0.0001% to 2% actual crosslinks. Suitable concentrations of cross-linker in the polymerization reaction range from 0.05%–1% by weight based on total cross-linking monomer with a preferred range of 0.10%–0.50% by weight. The synthesis of a graft copolymer hydrogel is described in Example 4.

As with the block and graft copolymers described above, the hydrogels of this invention are effective vehicles for the delivery of therapeutic drugs. Hydrogel copolymer-drug mixtures may be prepared by swelling the hydrogel in a solution containing the drug, followed by removal of the solution by evaporation. Hydrogels include gels where the solvent is water, as well as gels where the solvent is significantly non-aqueous. In one embodiment, the solution may contain at least 10% by weight of a non-aqueous solvent, and in a further embodiment may contain at least 99% by weight of a non-aqueous solvent. Hydrogels of this invention include any graft or block copolymers containing pH-sensitive and temperature-sensitive components, independent of the LCST of the resulting hydrogel. In one embodiment of this invention, the hydrogels have an LCST ranging from 20° C. to 40° C. at physiological pH.

The copolymer-drug particles of the present invention may be formulated for topical administration as suspensions of solid particles in a pharmaceutically acceptable carrier, and one skilled in the art could readily prepare suitable formulations using known techniques and methods. Such formulations include, but are not limited to, solutions, creams and gels. The copolymer-drug particles may generally be present in these formulations in a range from 0.1% to 20% by weight of the total suspension, and preferably from 1% to 10% by weight of the total suspension. In the practice of this invention the copolymer-drug particles have a particle size on average, less than about 50 μm in diameter, and preferably less than about 30 μm in diameter. Particles larger than 50 μm in diameter may be reduced to suitable particle size by mechanical milling or grinding.

As described above, the copolymer-drug particles may be suspended in a pharmaceutically acceptable carrier. In one embodiment, the pharmaceutically acceptable carrier may be a volatile carrier. Volatile carriers serve to transport the solid particles of the copolymer-drug particles to the treatment area and, upon contact with the treatment area, rapidly evaporate, to effectively deposit the particles on the treatment area. Suitable volatile carriers include fluorocarbon propellants (such as trichlorodifluoromethane and dichlorodifluoromethane) and such propellants may generally be present over a range from 5 to 20 times by weight the amount of copolymer-drug particles. The suspension of the copolymer-drug particles in the volatile carrier may be administered to the treatment area by any device suitable for effective delivery of the suspension. Effective delivery of the suspension preferably includes accurate and reproducible dosing of the copolymer-drug particles, and include metered dose nebulizers and devices which deliver the suspension as droplets (such as eye droppers).

In another embodiment, the copolymer-drug particles of the present invention may be administered as a suspension of particles in an aqueous carrier including distilled or sterile water. For ophthalmic administration, the osmolality of these aqueous compositions are preferably adjusted to physiological osmolality for physical comfort. Such aqueous compositions may have an osmolality of from about 50 to about 400 mOsM, preferably from about 100 to 300 mOsM, and more preferably about 150 mOsM. A suitable osmolality may be achieved by addition of a physiologically acceptable material such as a sugar or other nonionic compound.

In still a further embodiment, the copolymers of the present invention may be formulated for administration in liquid form by dissolving one or more of the copolymers in a pharmaceutically acceptable carrier. In one embodiment, the copolymer is present in these formulations at a sufficiently high concentration such that the formulation will gel upon contact with the treatment area. Typically, suitable concentrations of the copolymer in these formulations range from 0.1% to 20% by weight of the formulation, and preferably from 0.5% to 10% by weight of the formulation. In these formulations, the pharmaceutically acceptable drug may be present in a soluble or suspended form, or bound to a carrier. When the formulation gels upon contact with the treatment area, at least a portion of the drug present within the formulation is trapped within the gel.

In yet further embodiments, the copolymer-drug mixtures of this invention may be formulated as a solution, cream, gel, ointment, tablet, capsule or suppository. To this end, suppository formulations may be particularly suited for rectal administration of the copolymer-drug mixtures, while tablet and capsule forms are suitable for administration to the alimentary tract, including the stomach. Solutions, creams, gels and ointments are, for example, preferred for topical skin applications. The copolymer-drug mixtures may also be formulated for nasal or buccal administration by known techniques. Formulations for general systemic delivery are also within the scope of this invention, and are readily prepared using known techniques.

Physical mixtures of the block and graft copolymers of this invention with one or more polymers, including homopolymers (such as a homopolymer of AAc) and copolymers (such as random or block copolymers of EO/PO/EO) are included within the scope of this invention.

As mentioned above, in the context of drug administration the block and graft copolymers of this invention preferably have LCSTs in the range from 20° C. to 40° C. However, the graft and block copolymers (and hydrogels of the same) are not limited to only block and graft copolymers which satisfy this requirement. For example, cosmetic compositions, wound dressings, iontophoretic devices, monitoring electrodes, adhesives, suntan lotions, creams, foams, suppositories, tablets, and delivery gels may incorporate the block and graft copolymers of this invention having LCSTs well outside the above range (e.g., industrial, chemical or enzymatic processes). Furthermore, nasal, vaginal, oral ocular, rectal, dermal or otic delivery may similarly benefit by use thereof, as well as laxatives containing the same. With regard to vaginal delivery, the block or graft copolymer (or hydrogel) may be combined with a spermicide, ovacide, antimicrobial, antifungal, prostaglandin, steriodal or nonsteroidal fertility agent.

The block and graft copolymers (and hydrogels thereof) may also be used to control enzymatic or chemical reactions, or for separation of solution components, or for separation of ionic species, or for control of chemomechanical work, as well as for controlling viscosity or flowm (such as in oil or gas well drilling or production). Such copolymers (and hydrogels) may further be used to form a water or gas impermeable barrier between a well casing and surrounding rock formation. In such industrial settings, the block and graft copolymers (and hydrogels) of this invention may be used over a wide temperature range (−20° C. to 250° C.). Similarly, in industrial applications, they may also be used over a wide pH range (pH 0 to 16).

The block and graft copolymers of this invention, particularly the hydrogels thereof, may also be used as an absorbant agent, and preferably as superabsorbant agents, by exposing the hydrogel to a solvent or solution, or even for oil recovery from oil spills. Suitable solvents or solutions in this context include (but are not limited to) urine, feces, water, blood, brine, and ionic water solutions. Thus, the hydrogels may be used as an absorbing component of a diaper, and preferably with a swelling ratio of not less than 15. The block and graft copolymers, and hydrogels thereof, may also be used to provide moisture to, retain moisture at, or provide hydration to, the treatment area.

While the above disclosure is generally directed to block and graft copolymers comprising pH-sensitive and temperature-sensitive components, it should be recognized that polymer components which are sensitive to other environmental triggers may be employed. Thus, as used in the context of this invention, an environmentally sensitive polymer is a polymer that reversibly undergoes a change from primarily hydrophilic to primarily hydrophobic in response to a change in an environmental condition, such as temperature, pH, solvent or solvent concentration, ions or ionic concentration, light, or pressure. Materials and gels which exhibit these changes are known in the art. Hoffman, *J. Controlled Release* 6:297–305, 1987; Tanaka, *Physical Review Letters* 40(12):820–823, 1978; Tanaka et al., *Physical Review Letters* 38(14):771–774, 1978; Tanaka et al, *Physical Review Letters* 5 45:1636, 1980; Ilavsky, *Macromolecules* 15:782, 1982; Hrouz et al, *Europ. Polymer J.*, 17:361, 1981; Ohmine et al, *J. Chem Phys.* 8:6379, 1984; Tanaka et al, *Science* 218:462, 1982; Ilavsky et al, *Polymer Bull.* 7:107, 1982; Gehrke, *Responsive Gels: Volume Transitions II*; ed K. Dusek, Springer-Verlag, New York, pp. 81–114, 1993; Li et al, *Ann. Rev. Mat. Sci.* 22:243–277, 1992; Galaev et al, *Enzyme Microb. Technol.* 15:354–366, 1993 and Taylor et al, *J. Polymer Sci.* 13:2551–2570, 1975 (all of which are incorporated herein by reference). This change in hydrophilic to hydrophobic character may be evidenced by a decrease in transmission of light (LCST or cloud point), change in viscosity or swelling or collapse. As mentioned above, if an environmentally sensitive polymer undergoes the change in response to a change in temperature, it is a temperature-sensitive polymer, and if it undergoes the change in response to a change in pH, it is a pH-sensitive polymer.

Accordingly, in another embodiment of this invention, block and graft copolymers are disclosed which contain environmentally-sensitive polymer components which are responsive to different triggers. For example, block and graft copolymers containing two different pH-sensitive polymer components, or two different temperature-sensitive polymer components, may be used. Alternatively, the block and graft copolymers of this invention may contain, for example, a light-sensitive polymer component in combination with either a temperature-sensitive or pH-sensitive polymer component, or in combination with a different light-sensitive polymer, or in combination with a polymer component sensitive to other triggers The following examples are provided for purposes of illustration, not limitation.

EXAMPLES

Example 1

Environmentally-Sensitive Block Copolymers Comprising Temperature-Sensitive and pH-Sensitive Homopolymer Components In this example, the synthesis and characterization, temperature-sensitive behavior, and drug loading and release properties of block copolymers comprising a temperature-sensitive polymer component and a pH-sensitive polymer component is described.

A. Synthesis and Characterization of Block Copolymers NIPAAm-b-AAc

Block copolymers (NIPAAm-b-AAc) comprising a temperature-sensitive polymer component (NIPAAm) and a pH-sensitive polymer component (AAc) were synthesized from oligomers of NIPAAm and AAc. The block copolymers were prepared by covalently coupling an amino-terminated AAc oligomer to the active ester carbonyl-terminated NIPAAm oligomer to yield an amide linked block copolymer (see 3. below). In the present method, an amino group was introduced into one end of the AAc oligomer (see 1. below) and an active ester group (an N-hydroxy succinimide group) was introduced into one end of the NIPAAm oligomer (see 2. below).

1. Synthesis of Amino-Terminated OligoAAc

The amino-terminated oligoAAc was synthesized by radical polymerization of acrylic acid (AAc) using azobisisobutyronitrile (AIBN) as an initiator and 2-aminoethanethiol hydrochloride (AET-HCL) as a chain transfer reagent. The polymerization was carried out at 60° C. using methanol as solvent. After polymerization, the polymer was collected by precipitating into diethyl ether, redissolving in dimethylformamide (DMF) mixed with triethylamine to remove the salt, and reprecipitating into diethyl ether. By changing the ratio of monomer to chain transfer reagent, the amino-terminated oligoAAc could be obtained with different molecular weights. The synthesis of the amino-terminated oligomers of AAc is represented schematically below.

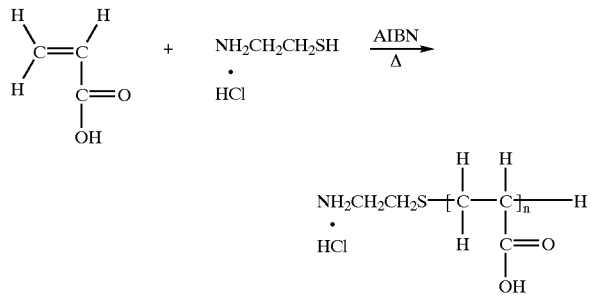

The molecular weights of the oligomers were determined by end-group analysis as disclosed in Hazra et al., *Analytical Biochemistry* 137: 437–43 (1984). In this method, 2,4,6-trinitrobenzenesulfonic acid (TNBS) was reacted with the amino end group, and the absorbance of the product at 420 nm was measured. A calibration curve was established using three different amines with different numbers of carbons as follows: $H_2N(CH_2)_2COOH$, $H_2N(CH_2)_3COOH$, and $H_2N(CH_2)_5COOH$. Table 1 summarizes the synthetic conditions and results for the polymerizations of AAc.

TABLE 1

| Polymerization of AAc | | | |
|---|---|---|---|
| AAc:AIBN:AET:HCl (mole) | Polymn. Time (h) | Yield (% w/w) | MW[a] |
| 100:1:1 | 3.0 | 90 | 15200 |
| 100:1:2 | 3.5 | 73 | 6600 |
| 100:1:4 | 4.0 | 77 | 3500 |
| 100:1:6 | 4.0 | 55 | 2200 |
| 100:1:8 | 4.0 | 56 | 1500 |
| 100:1:10 | 4.0 | 42 | 1200 |

*Concentration of monomer in methanol: 3.5 mole/L, polymerization temperature: 60° C.;
[a]The molecular weight (MW) of the oligomer was determined by TNBS.

The molecular weight of the oligomers was controlled by changing the ratio of monomer to chain transfer reagent, molecular weights ranging from 1200 to 15,200 were obtained. From the data in the table shown above, the chain transfer constant for this system was calculated to be $C_s=0.62$. These oligomers were used for the further synthesis of the block copolymer of NIPAAm-b-AAc.

2. Synthesis of NHS-Activated OligoNIPAAm

The NHS-activated oligoNIPAAm was prepared in two steps. First, the carboxy-terminated oligoNIPAAm was prepared by radical polymerization using AIBN as an initiator and 2-mercaptopropionic acid as a chain transfer reagent. The polymerization was carried out at 60° C. using tert-butanol as solvent and the polymer was collected by precipitating into diethyl ether. Secondly, the carboxyl group at the end of oligoNIPAAm was activated by N-hydroxy succinimide (NHS) in the presence of an activating reagent, dicyclohexylcarbodiimide (DCC), in methylene chloride at 0° C.–20° C. for 24 hours. After activation, the polymer was recovered by precipitating into diethyl ether (see, Chen and Hoffman, *Bioconjugate Chem.* 4: 509–14, 1993). The syn thesis of the NHS-activated oligomers of NIPAAm is represented schematically below.

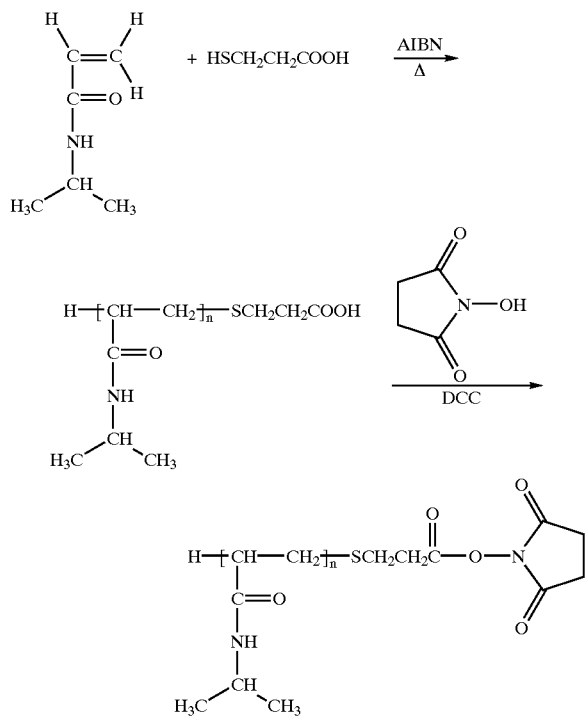

3. Synthesis of Block Copolymer NIPAAm-b-AAc

The block copolymer of NIPAAm-b-AAc was synthesized by coupling the amino-terminal group of the oligoAAc with the NHS-activated carboxyl group of the oligoNIPAAm by reaction in DMF at 60° C. overnight. The synthesis of the block copolymers of NIPAAm-b-AAc is represented schematically below.

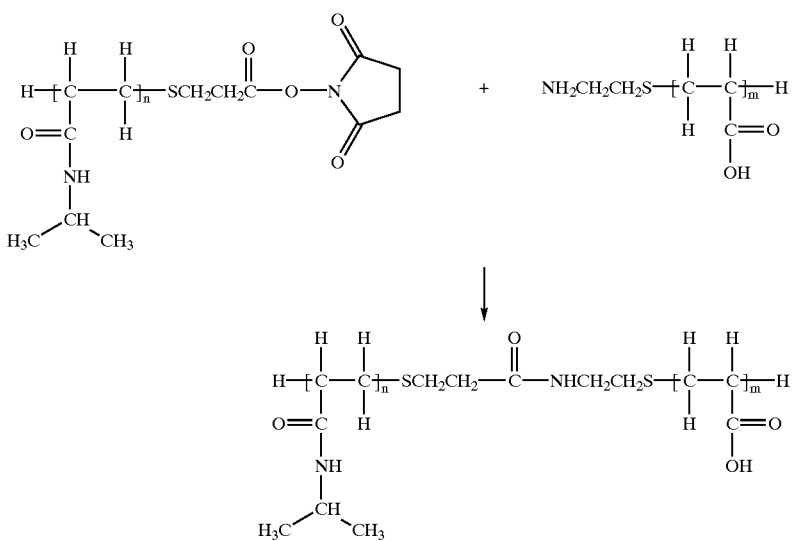

The reaction mixture was poured into ethyl acetate to precipitate the block copolymer product and unreacted oligoAAc. The unreacted oligoNIPAAm is soluble and remained in solution. The precipitate containing the product block copolymer and unreacted oligoAAc was then collected by filtration and dissolved in pH 7.4 phosphate buffer. The addition of saturated aqueous ammonium sulfate solution precipitated the block copolymer which was collected by filtration and washed with dilute hydrochloric acid to remove residual ammonium sulfate. The block copolymer was dried in a vacuum oven overnight. Table 2 presents the results of the block copolymer synthesis.

TABLE 2

| Compositions of Block Copolymers NIPAAm-b-AAc | | | | |
|---|---|---|---|---|
| | 1 | 2 | 3 | 4 |
| Percent of NIPAAm | 76% | 58% | 43% | 24% |
| oligoNIPAAm MW | 4800 | 4800 | 4800 | 4800 |
| oligoAAc MW | 1500 | 3500 | 6600 | 15200 |
| Total MW | 6300 | 8300 | 11400 | 20000 |

Block copolymers of NIPAAm-b-AAc with four different compositions were synthesized. The temperature-sensitivity properties of these block copolymers are described below.

B. Temperature-Sensitive Behavior of Block Copolymers of NIPAAm-b-AAc

The phase transition behavior of the block copolymer is a critical property for topical drug delivery. To investigate the phase transition behavior of the copolymers, a spectroscopic method was used to determine the light transmission (or absorbance) of the copolymer solution at 500 nm as a function of time during a constant rate of temperature rise. Below the phase transition temperature (also known as LCST or cloud point), light transmission is 100%. However, when the phase transition temperature is reached, the polymer begins to aggregate and light transmission of the solution decreases, absorbance increases.

As illustrated in FIG. 1, all of the block copolymers prepared as described above exhibit a cloud point (LCST) near 32° C. (2° C. below eye temperature). However, only the highest NIPAAm content block copolymer, 76% by weight, showed a relatively sharp phase transition. The common cloud point for the different block copolymers indicates that the temperature-sensitivity of the oligoNIPAAm component changes very little after being end-linked to other hydrophilic polymers.

C. Drug Loading and Release from Block Copolymers of NIPAAm-b-AAc

1. Drug Loading

Generally, in this method, the block copolymer NIPAAm-b-AAc and the drug timolol-hydrogen maleate salt (timolol) were dissolved in a solvent (methanol) to yield a solution of the block copolymer and drug. The block copolymer-drug particle was recovered by precipitation into a non-solvent (diethyl ether). For example, the block copolymer with 20 wt % of NIPAAm and a total molecular weight of 19,000 (4,000 for oligoNIPAAm and 15,000 for oligoAAc) was used to prepare exemplary lock copolymer-drug particles. A solution of 0.6 g of the copolymer and 6.0 mg of the drug in 8 mL of methanol was prepared. This solution was precipitated into 800 ml of ether. The precipitated block copolymer-drug particles were recovered by filtration, washed three times with ether and dried under vacuum at room temperature. The recovery was 65% with a drug content of 1.1 wt %. In a control experiment, homopolymer (polyAAc)-drug particles were prepared in the same procedure as described above, except homopolyAAc having a molecular weight of 250,000 was used instead of the block copolymer NIPAAm-b-AAc. In this experiment, the percent recovery was 93% with a drug content of 1%. These materials were ground into small particles (ca. 20–40μ) for the drug release study described below.

2. Drug Release

Solutions of 10 mg of the block copolymer with 1.1 wt % drug prepared as described above and polyAAc with 1% drug in 15 mL of PBS buffer (pH 7.4) were prepared. The solutions were well-stirred during the drug release process. The amount of drug release from the polymers was determined by circulating the buffer to an absorbance spectrophotometer where the absorbance of the drug solution at 294 nm was measured as a function of time. The drug release results are presented in FIG. 2.

Figure 2:
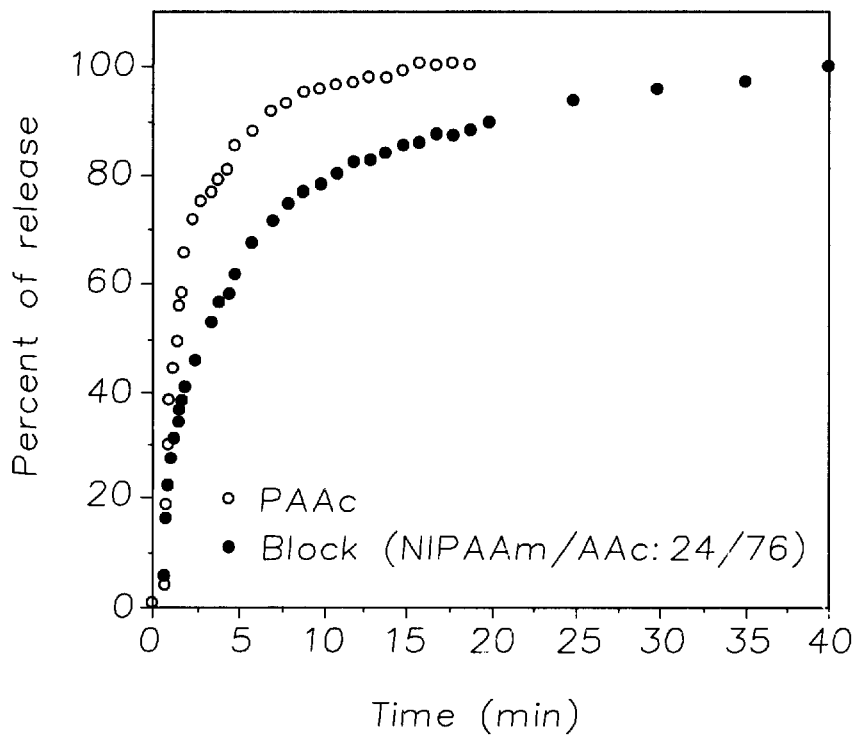
FIG. 2 illustrates the release of a drug (i.e., timolol) from NIPAAm-b-AAc copolymer-drug particles as compared to homopolyAAc-drug particles in phosphate buffered saline (pH 7.4) at 34° C.

Despite the higher molecular weight of homopolyAAc (molecular weight 15,000), the drug release from the block copolymer NIPAAm-b-AAc (molecular weight 4,000) was significantly slower. Referring to FIG. 2 above, 80% drug release from the block copolymer requires 12 minutes, while the same extent of drug release occurs in 5 minutes with homopolyAAc. For comparative purposes, release data for graft copolymer NIPAAm-g-AAc and random copolymer NIPAAm-AAc is presented in FIG. 5. Note that 80% drug release is achieved in 8 minutes for the graft copolymer NIPAAm-g-AAc (20% by weight NIPAAm) and in 3 minutes for the random copolymer NIPAAm-AAc (30% by weight NIPAAm).

The slower release rate from the block copolymer may be attributed to its temperature-sensitive component, NIPAAm. At 34° C., the NIPAAm component aggregates and becomes hydrophobic, resulting in a kind of gelation of the block copolymer-drug mixture, leading to a retardation in both dissolution rate and drug release rate. In fact, it was found that the block copolymer was not quite soluble but only swollen in PBS buffer (pH 7.4) at 34° C.

FIG. 2 shows that a reduction in drug release rate is obtained compared to homopolyAAc by using the block copolymer as a matrix, even for a block copolymer with a total molecular weight of only 19,000 and only 20 wt % of NIPAAm component.

Example 2

Environmentally-Sensitive Graft Copolymers Comprising Temperature-Sensitive and pH-Sensitive Homopolymer Components In this example, the synthesis and characterization, temperature-sensitive behavior, and drug loading and drug release properties of graft copolymers comprising a temperature-sensitive homopolymer component and a pH-sensitive homopolymer component is described. Because of the nature of graft copolymers, two general embodiments are possible. The graft copolymer may possess a pH-sensitive polymer backbone with one or more pendant temperature-sensitive polymer components. Alternatively, the graft copolymer may have a temperature-sensitive polymer backbone with one or more pendant pH-sensitive polymer components. This example is directed to a graft copolymer with a pH-sensitive homopolymer backbone with pendant temperature-sensitive homopolymer components.

A. Synthesis and Characterization of Graft Copolymers NIPAAm-g-AAc

Graft copolymers (NIPAAm-g-AAc) comprising a temperature-sensitive homopolymer component (NIPAAm) and a pH-sensitive homopolymer component (AAc) were synthesized by two methods. The graft copolymers were synthesized by copolymerization of AAc with a macromonomer of NIPAAm and by the conjugation of oligomeric NIPAAm to polyAAc.

1. Macromonomer Copolymerization Method

Copolymerization of acrylic acid and an appropriate macromonomer of NIPAAm results in the formation of a comb-like graft copolymer having a polyAAc backbone with pendant oligoNIPAAm side chains. The macromonomer of NIPAAm appropriate for copolymerization with acrylic acid is prepared from an amino-terminated oligoNIPAAm as described below.

a. Synthesis of Amino-Terminated OligoNIPAAm and its Corresponding Macromonomer

OligoNIPAAm was synthesized by free radical polymerization of NIPAAm in methanol solution (2.5 M NIPAAm) using AIBN and AET-CL as initiator and chain transfer reagent, respectively. The polymerization was carried out at 60° C. for 22 hours. The results for two representative syntheses are presented below in Table 3.

TABLE 3

| Polymerization of NPAAm | | |
|---|---|---|
| NIPAAm:AIBN:AET-HCl | Yield | MW[a] |
| 100:1:12 | 59.7 | 3300 |
| 100:1:8[b] | 68.5 | 2200 |

[a]Molecular weight was estimated by conductometric titration with sodium hydroxide;
[b]pH of the monomer solution was adjusted to 1.0 prior to polymerization.

The macromonomer of NIPAAm may be prepared by reaction of an amino-terminated oligoNIPAAm with vinyl azlactone. In a representative synthesis, a solution of 5.0 g (2.27 mmol) amino-terminated oligoNIPAAm (MW 2200) and 0.94 g (6.79 mmol) vinylazlactone in 120 mL tetrahy drofuran was stirred at 40° C. for 16 hours. The reaction mixture was precipitated into 1000 mL diethyl ether and the resulting precipitate was collected by filtration. The product was isolated in 82% yield. The synthesis of the macromonomer of NIPAAm is presented schematically below.

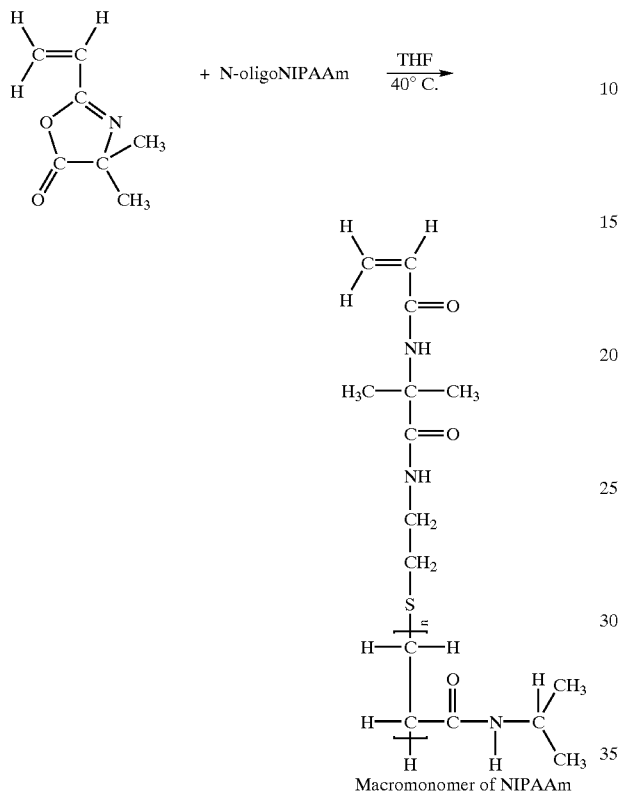

b. Copolymerization Reaction

The graft copolymer NIPAAm-g-AAc was prepared by copolymerization of AAc with the macromonomer of NIPAAm prepared as described above. In a representative polymerization, the monomer concentration was 12% weight/volume in methanol with AIBN as initiator. The polymerization was carried out at 60° C. for 1.5 hours. The copolymer product was collected by precipitation into methyl ethyl ketone, and was further purified by reprecipitation into tetrahydrofuran. The results for two representative syntheses are presented below in Table 4.

TABLE 4

Copolymerization of AAc and Macromonomer NIPAAm

| Feed | | Copolymer | |
|---|---|---|---|
| $W_{AAc}/W_{NIPAAm}$ | Yield | $W_{AAc}/W_{NIPAAm}$ | $M_{AAc}/M_{NIPAAm}$ |
| 60/40 | 68 | 55/45 | 97/3 |
| 80/20 | 66 | 72/28 | 99/1 |

The synthesis of the graft copolymer NIPAAm-g-AAc by the copolymerization method is represented schematically below.

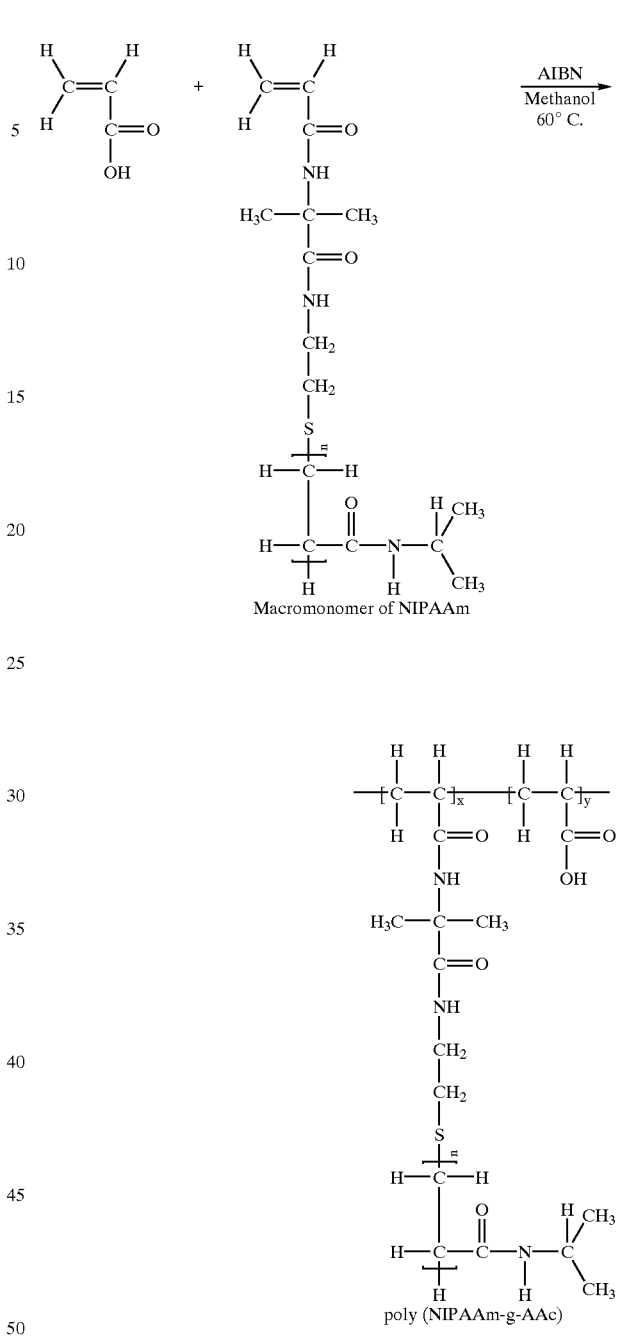

2. Conjugation Method

The graft copolymer of NIPAAm-g-AAc was synthesized by reaction of the amino group of the amino-terminated oligoNIPAAm with the carboxyl groups on the polyAAc backbone. In a representative reaction, amide bond formation was achieved by treatment of polyAAc (MW 250,000) and amino-terminated oligoNIPAAm (MW 3300) with dicyclohexylcarbodiimide in methanol at room temperature for 24 hours. The product graft copolymer was isolated by precipitation into methyl ethyl ketone, and further purified by reprecipitation into tetrahydrofuran. The results of the conjugation are presented below in Table 5.

TABLE 5

Conjugation of NIPAAm to PolyAAc

| NIPAAm in Feed | | | NIPAAm in Copolymer[a] | |
|---|---|---|---|---|
| mole % | wt % | Yield | mole % | wt % |
| 0.5 | 20 | 83 | 0.5 | 19 |
| 0.7 | 25 | 78 | 0.7 | 24 |
| 0.9 | 30 | 93 | 0.9 | 29 |
| 2.1 | 50 | 91 | 2.0 | 49 |

[a]Composition of NIPAAm was determined by back titration of the polyAAc component.

The synthesis of the graft copolymer NIPAAm-g-AAc by the conjugation method is represented schematically below.

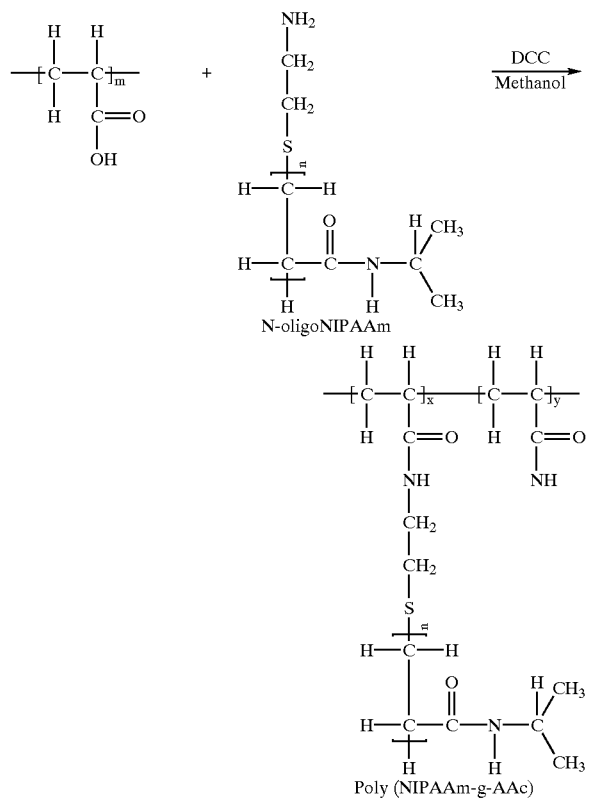

B. Temperature-Sensitive Behavior of the Graft Copolymers

The thermal-sensitivity of the graft copolymers prepared by copolymerization and conjugation exhibit similar temperature sensitivity. The graft copolymers prepared by direct conjugation with 20% to 50% NIPAAm demonstrate phase separation between 30° C. and 35° C. and are most appropriate as vehicles for drug delivery. The temperature-sensitive behavior of the graft copolymers NIPAAm-g-AAc is presented in FIG. 3. The graft copolymer compositions begin to phase separate around 32° C. and their response to temperature is rather broad due to the influence of the backbone COO$^-$Na$^+$ moieties.

C. Drug Loading and Release from the Graft Copolymers

1. Drug Loading

Graft copolymer drug loading was performed as described generally in Example 1C1. Solution of 0.5 g of the graft copolymer and 5.0 mg of timolol maleate in 8 ml methanol was precipitated into 800 mL of diethyl ether. White, sphere-like particles of the graft copolymer with an average 2–3 mm diameter were obtained. The percent recovery was 92% with 1 wt % of drug loaded The material was ground into ca. 20–40$\mu$ particles for the drug release experiment.

2. Drug Release

A suspension of 40 mg graft copolymer NIPAAm-g-AAc/ timolol mixture in 40 mL of PBS buffer was prepared. As described above in Example 1C2, the amount of drug released from the complex was determined as a function of time by determining the absorbance of the solution. The results of the drug release at 34° C. and 37° C. are presented in FIGS. 4 and 5, respectively.

Figure 4:
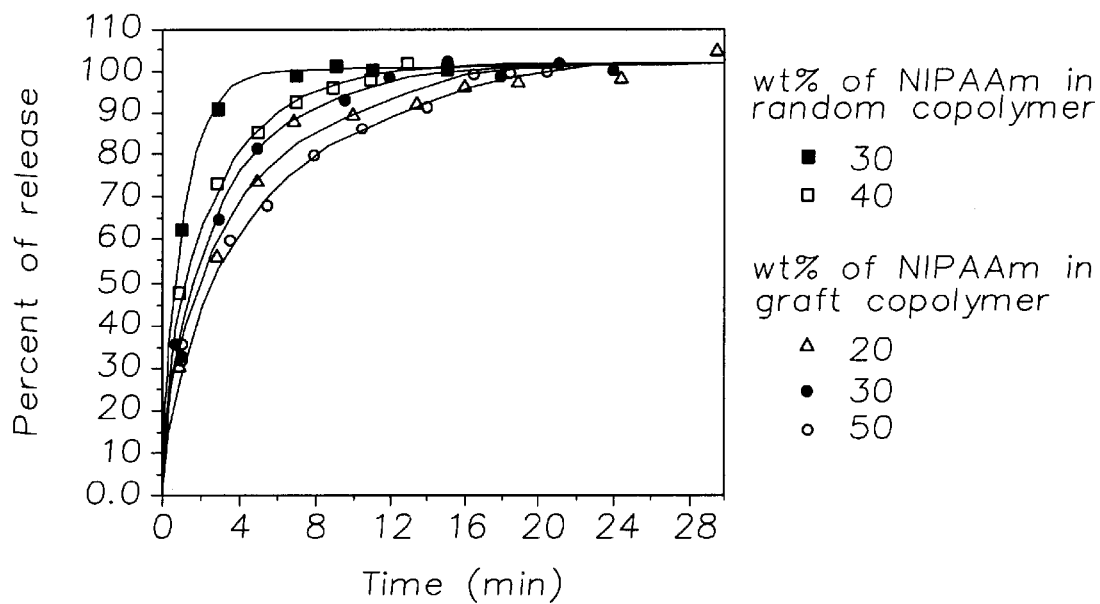
FIG. 4 illustrates the release of timolol from copolymer-drug particles of these graft copolymers of NIPAAm-g-AAc as compared to random copolymers of NIPAAm and AAc in phosphate buffered saline (pH 7.4) at 34° C.

As shown in FIG. 4, drug release from graft copolymers is slower than from particles of random copolymers with similar compositions at 34° C. Increasing the temperature of the release medium to 37° C. (FIG. 5) slows down the release rate from the graft copolymers but not the release rate from the random copolymers. The results indicate that the increased hydrophobicity of the graft chains contributes to the slower release of drug.

Alternatively, copolymer dissolution and drug release may be determined simultaneously by casting the copolymer-drug mixture on a glass disc. In this method, a copolymer-drug mixture is cast onto a glass disc forming a film. The coated glass disc is then suspended in an appropriate medium such as phosphate buffered saline, pH 7.4, or distilled water. The temperature of the drug released into the medium may also be controlled to investigate temperature effects on dissolution and drug release. The method facilitates the determination of drug released by measurement of the absorbance of the medium over time as described above, and simultaneously permits the determination of the amount of copolymer-drug mixture dissolved by measuring the weight of the film cast onto the hanging glass disc.

Figure 6:
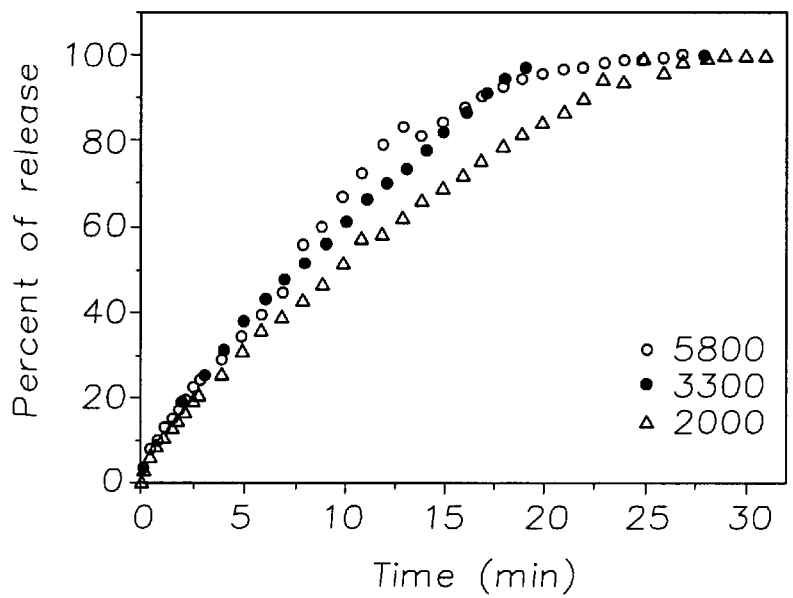
FIG. 6 illustrates the release of timolol from cast films of copolymer-drug mixtures of various graft copolymers of NIPAAm-g-AAc (oligomer molecular weight 2000 with 51 pendant chains/backbone; molecular weight 3300 with 31 pendant chains/backbone, molecular weight 5800 with 18 graft chains/backbone; polyAAc backbone molecular weight 250,000) in phosphate buffered saline (pH 7.4) at 34° C.
Figure 7:
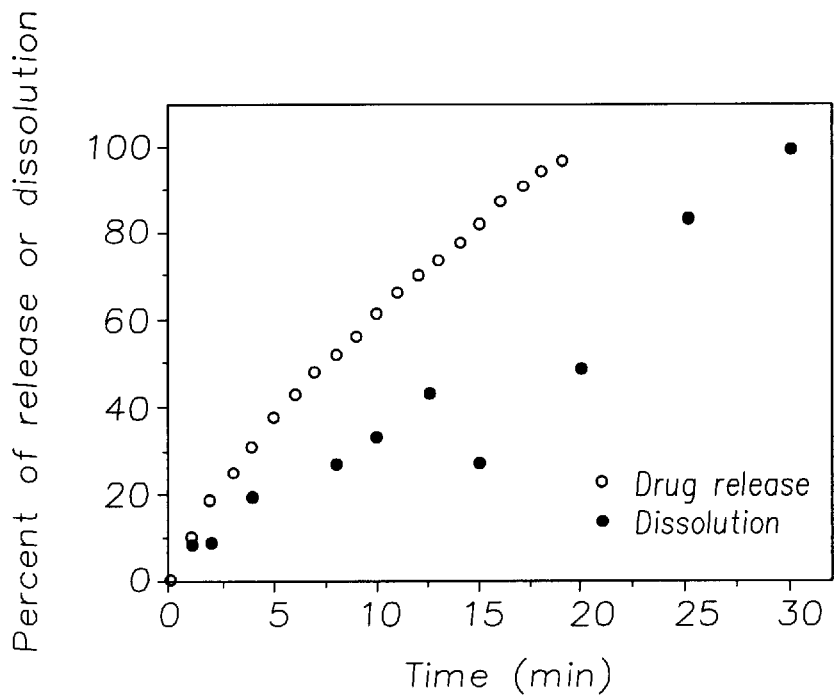
FIG. 7 illustrates the rate of both timolol release and graft copolymer-timolol mixture dissolution from a cast film (oligomer molecular weight 3300 with 31 pendant chains/backbone; polyAAc backbone molecular weight 250,000) in phosphate buffered saline (pH 7.4) at 34° C.

The results for drug release and dissolution for graft copolymer-timolol mixtures determined by the film cast on glass disc method are presented in FIGS. 6 and 7. FIG. 6 illustrates the effect on drug release of MW of oligoNIPAAm used in the graft copolymers prepared as described above. FIG. 7 illustrates the difference in the rates of release and dissolution for a graft copolymer NIPAAm-g-AAc (30% weight NIPAAm).

Figure 8:
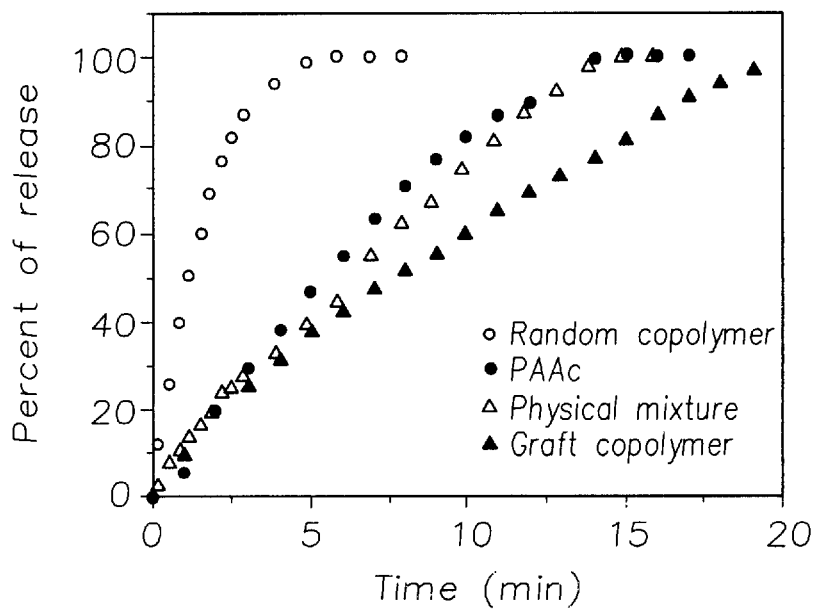
FIG. 8 illustrates the release of timolol from cast films of polymer-drug mixtures: random copolymer with 30% NIPAAm; graft copolymer with 30% NIPAAm where NIPAAm has molecular weight of 3,300; a physical mixture of NIPAAm (molecular weight 3,300) and homopolyAAc (molecular weight 250,000) (30:70); and homopolyAAc with molecular weight 250,000 in phosphate buffered saline (pH 7.4) at 34° C.

FIG. 8 compares the effect of polymer structure on the rate of release of timolol from various polymer-drug cast films. The rate of release of timolol from homopolyAAc (molecular weight 250,000) is compared to different polymer-drug mixtures each containing 30 weight percent NIPAAm (i.e., random copolymer, graft copolymer, and a physical mixture of homopolyNIPAAm and homopolyAAc). The results demonstrate that release from the random copolymer is essentially complete within about 5 minutes while release from the graft copolymer is the most prolonged, nearly complete release taking about 20 minutes. Drug release from the physical mixture of homopolyNIAPPa and homopolyAAc was comparable to the rate of release from homopolyAAc, indicating that the physical mixture of temperature-sensitive and pH-sensitive homopolymers is no more effective than the use of the pH-sensitive homopolymer alone and significantly less effective that the corresponding graft copolymer.

Example 3

Environmentally-Sensitive Graft Copolymers Comprising Temperature-Sensitive Copolymer and pH-Sensitive Homopolymer Components In this example, the synthesis and characterization, temperature-sensitive behavior, and drug loading and drug release properties of graft copolymers comprising a temperature-sensitive copolymer component and a pH-sensitive homopolymer component is described. Two general embodiments are possible. The graft copolymer may possess a pH-sensitive polymer backbone with one or more pendant temperature-sensitive polymer components. Alternatively, the graft copolymer may have a temperature-sensitive polymer backbone with one or more pendant pH-sensitive polymer components. This example is directed to a graft copolymer with a pH-sensitive homopolymer backbone with pendant temperature-sensitive copolymer components.

and the polymerization was performed at 60° C. for 1 hour. The co-oligomer thus formed was recovered by precipitating into ether. The yield was 45% and the number average molecular weight of the co-oligomer determined by vapor pressure osmometry (VPO) was 3100. The BMA composition in the co-oligomer was determined to be 4 mole % by $^{1}$H-NMR. The synthesis of co-oligomer NIPAAm-BMA is represented schematically below.

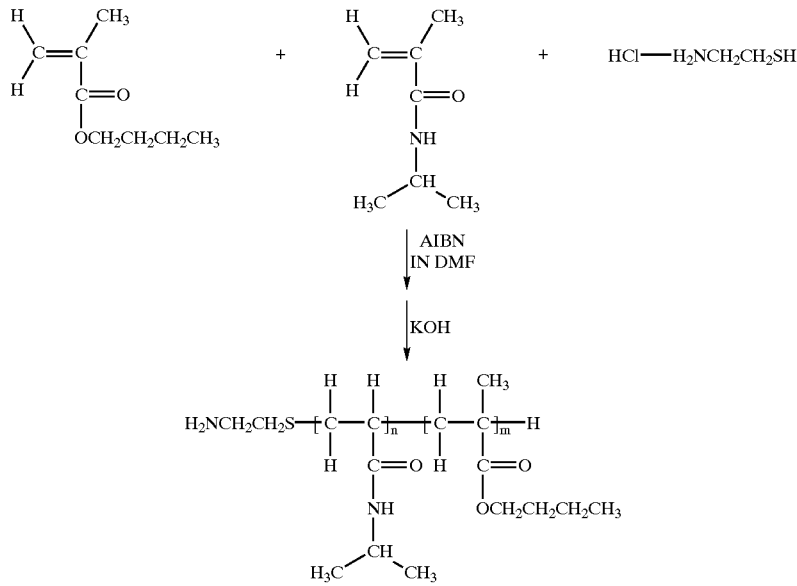

A. Synthesis and Characterization of Graft Copolymers NIPAAm-BMA-g-AAc

Graft copolymers (NIPAAm-BMA-g-AAc) comprising a temperature-sensitive copolymer component (NIPAAm-BMA) and a pH-sensitive homopolymer component (AAc) were synthesized from oligomers of NIPAAm-BMA and AAc. The graft copolymers were synthesized by covalently coupling an amino-terminated NIPAAM-BMA oligomer (see 1. below) to one or more carboxyl groups on the polyAAc backbone (see 3. below).

1. Synthesis of Amino-Terminated Co-oligo(NIPAAm-BMA)

Copolymerization of NIPAAm with a more hydrophobic monomer produces a copolymer with a lower LCST (cloud point) than the homopolymer polyNIPAAm. A co-oligomer with a lower LCST was synthesized by copolymerization of NIPAAm with a more hydrophobic comonomer, butyl-methacrylate (BMA) in the presence of chain transfer reagent, 2-aminoethanethiol hydrochloride (AET-CL) to obtain an amino-terminated co-oligomer NIPAAm-BMA. The co-oligomer was then grafted onto polyAAc.

In a representative synthesis, 3 mole % of BMA and 97 mole % of NIPAAm were charged with the molar ratio of monomer to initiator (AIBN) to chain transfer reagent (AET-CL) of 100:1:5. 40 mL of DMF was used as solvent 2. Determination of LCST of the Co-Oligomer NIPAAm-BMA The LCST of the co-oligomer was spectroscopically measured at 500 nm using a 0.2% polymer solution in either pure water or PBS buffer, pH 7.4, as described above in Example 1B. The results are presented in FIGS. 9 and 10, respectively.

Figure 9:
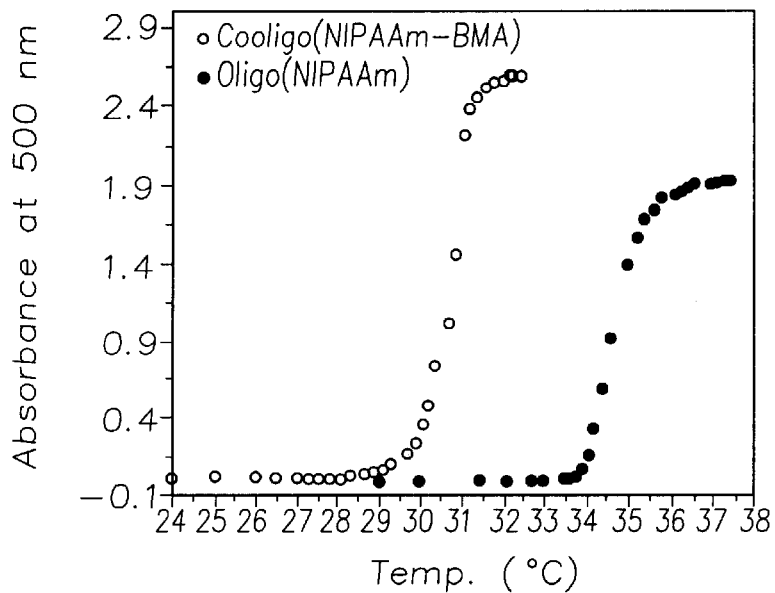
FIG. 9 illustrates the temperature-sensitive behavior of 0.2 weight percent solutions of cooligoNIPAAm-BMA and oligoNIPAAm in distilled water.
Figure 10:
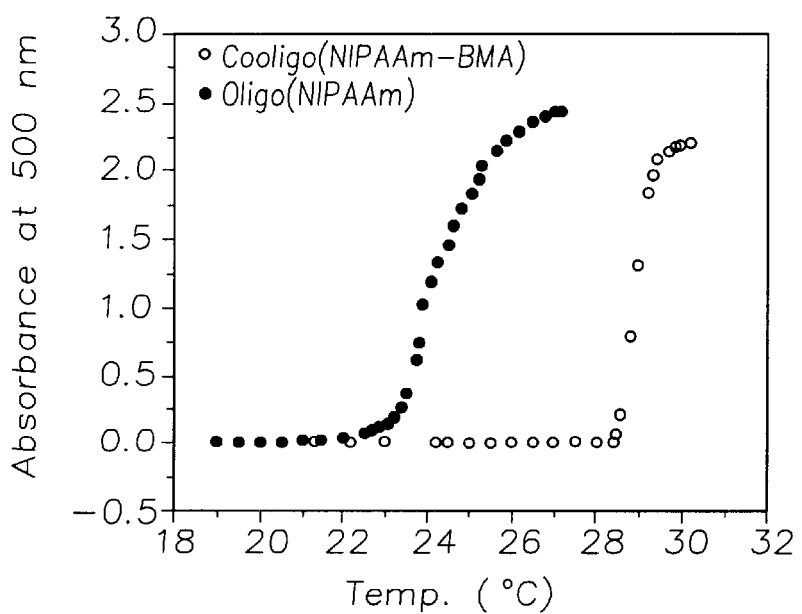
FIG. 10 illustrates the temperature-sensitive behavior of 0.2 weight percent solutions of cooligoNIPAAm-BMA and oligoNIPAAm in phosphate buffered saline (pH 7.4).

Referring to FIGS. 9 and 10, the co-oligomer shows a phase transition in pure water at 30° C., ca. 4° C. lower than the oligoNIPAAm, and yet retains the same sharp response. In PBS buffer, the co-oligomer shows an even lower phase transition at 24° C., ca. 5° C. lower than oligoNIPAAm. The lower phase transition for the co-oligomer in PBS as compared to water is believed to be due to a salt effect. The introduction of BMA comonomer units into the oligoNIPAAm provides a co-oligomer NIPAAm-BMA with a lower LCST (cloud point) than oligoNIPAAm. The 4° C.–5° C. difference in the LCST of the co-oligomer NIPAAm-BMA compared oligomer NIPAAm provides for increased versatility in the temperature-sensitive polymer component of the graft copolymer of the present invention.

3. Synthesis of Graft Copolymer of Co-oligo NIPAAm-BMA-g-AAc

The graft copolymer of co-oligo[NIPAAm-BMA]-g-AAc was synthesized by reaction of the amino group of the amino-terminated co-oligomer NIPAAm-BMA with the carboxyl group(s) on the polyAAc backbone. Amide bond formation was achieved in the presence of dicyclohexylcarbodiimide (DCC) at room temperature for 24 hours. The weight ratio of polyAAc to co-oligomer used for the reaction was 1, i.e., 50/50 (wt/wt) varied from 50/50 to 95/5 (wt/wt). The graft copolymer was recovered in 75%–90% yield by precipitation into tetrahydrofuran (THF).

TABLE 6

Graft Copolymer Synthesis Results

| Sample No. | Co-oligomer in feed in wt % | Yield | Co-oligomer in copolymer[a] wt % |
|---|---|---|---|
| 1 | 50 | 91 | 45.5 |
| 2 | 20 | 80 | 19.0 |
| 3 | 30 | 77 | 28.0 |
| 4 | 10 | 74 | 8.9 |
| 5 | 5 | 82 | 4.5 |

[a]Compositions of co-oligomer in the graft copolymer was determined by back titration of the polyAAc component.

The synthesis of graft copolymers (NIPAAm-BMA)-g-AAc is represented schematically below.

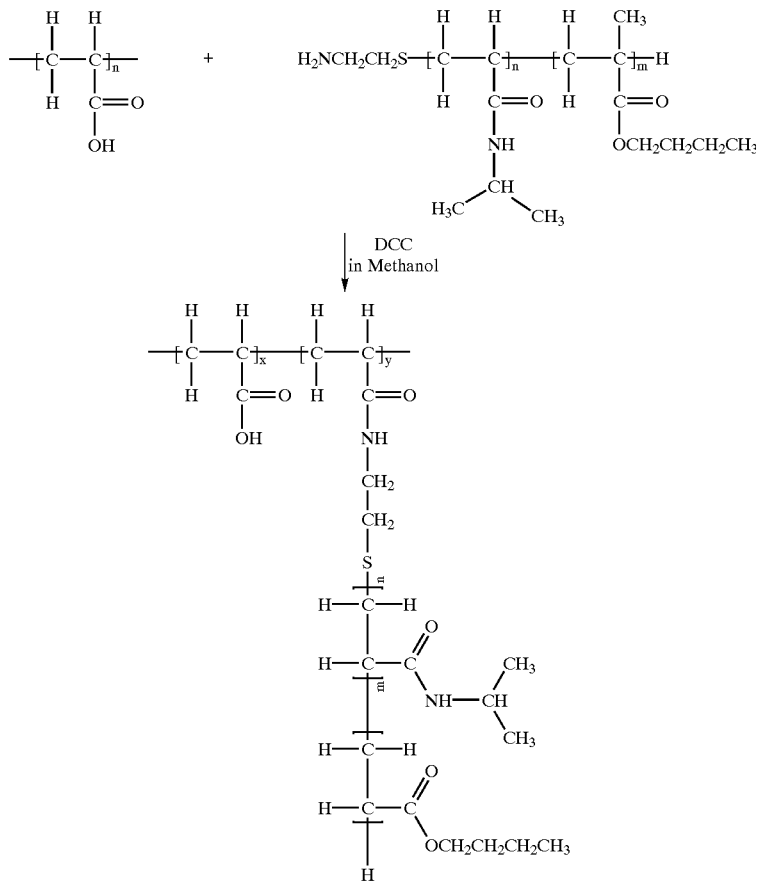

B. Temperature-Sensitive Behavior of the Graft Copolymers

Figure 11:
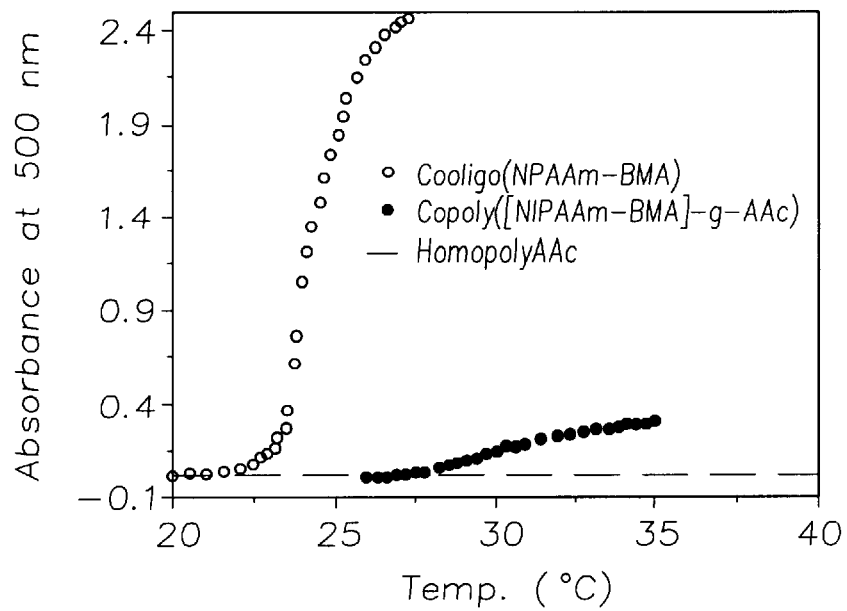
FIG. 11 illustrates the temperature-sensitive behavior of 0.2 weight percent solutions of graft copolymer (NIPAAm-BMA)-g-AAc, cooligoNIPAAm-BMA and homopolyAAc in phosphate buffered saline (pH 7.4).

The phase transition behavior of the graft copolymer NIPAAm-BMA-g-AAc was determined as described above in Example 1B. The phase transition data for the graft copolymer (NIPAAm-BMA)-g-AAc, the co-oligomer NIPAAm-BMA, and homopolyAAc are presented in FIG. 11. Referring to FIG. 11, the graft copolymer starts its phase transition in PBS at 28° C. and at 34° C. the phase transition is almost complete. The thermally-induced phase transition temperature for the above-described graft copolymer is significantly lowered by the introduction of hydrophobic comonomer units (BMA) into the oligoNIPAAm. At eye temperature (34° C.), the graft co-oligomer chain becomes sufficiently hydrophobic to significantly reduce the drug release rate.

C. Drug Loading and Release from Graft Copolymers

1. Drug Loading

Graft copolymer drug loading was performed as described generally in Example 1C1. A solution of 0.5 g of the graft copolymer and 5.0 mg of timolol-maleate in 8 ml methanol was precipitated into 800 mL of diethyl ether. White, sphere-like particles of the graft copolymer with an average 2–3 mm diameter were obtained. The percent recovery was 92% with 1 wt % of drug loaded. The material was ground into ca. 10–20$\mu$ particles for the drug release experiment.

2. Drug Release

A suspension of 40 mg graft copolymer (NIPAAm-BMA)-g-AAc/drug mixture in 40 mL of PBS buffer was prepared. As described above in Example 1C2, the amount of drug released from the mixture was determined as a function of time by determining the absorbance of the solution. The results of the drug release are presented in FIG. 12. For comparison, the drug release data for graft copolymer NIPAAm-g-AAc and random copolymer NIPAAm-AAC is presented in FIG. 5.

Figure 5:
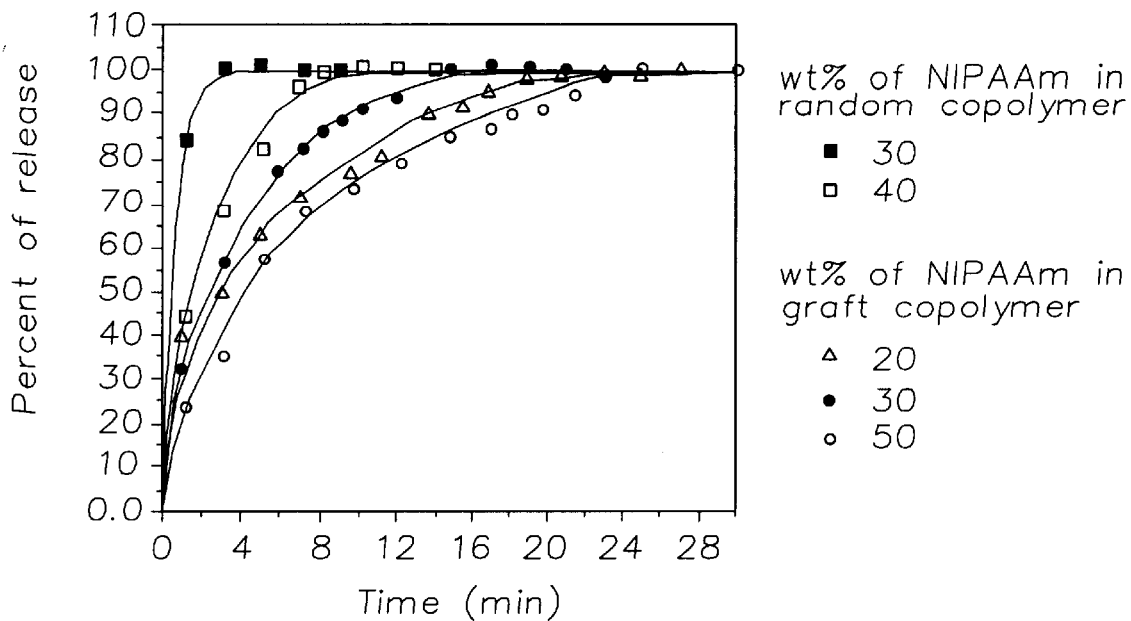
FIG. 5 illustrates the release of timolol from copolymer-drug particles of graft copolymers NIPAAm-g-AAc as compared to random copolymers of NIPAAm and AAc in phosphate buffered saline (pH 7.4) at 37° C.
Figure 12:
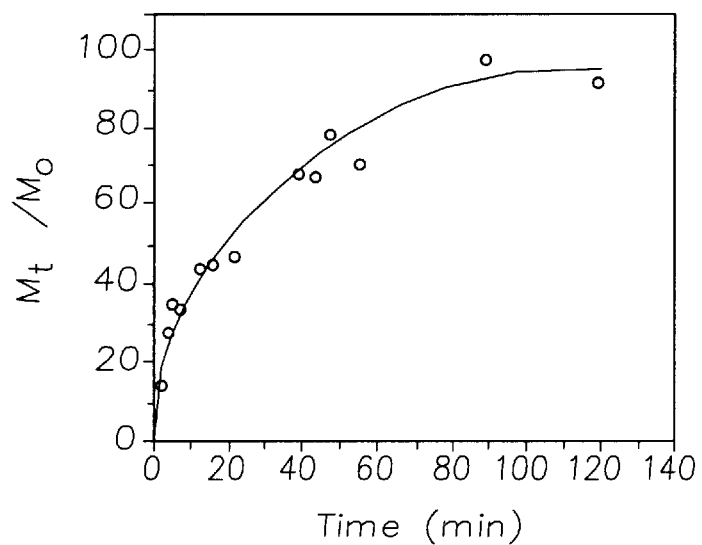
FIG. 12 illustrates the release of timolol from copolymer-drug particles of graft copolymer (NIPAAm-BMA)-g-AAc in phosphate buffered saline (pH 7.4) at 34° C.

Referring to FIGS. 5 and 12, complete release of the drug from graft copolymer poly([NIPAAm-BMA]-g-AAc) requires 80 to 90 minutes, while complete release from the graft copolymers which have pure oligoNIPAAm as the graft component requires only about 20 minutes. The conclusion is that a more hydrophobic grafted oligomer provides for slower release rates. By increasing the hydrophobicity of the graft copolymer, the drug release rate is reduced significantly compared to polyAAc. Graft copolymers with less than 20% by weight co-oligomer are erodible and show a reduced rate of drug release. Graft copolymers with greater than 20% by weight co-oligomer also significantly reduce the drug release rate, but these copolymers are not erodible.

Figure 13:
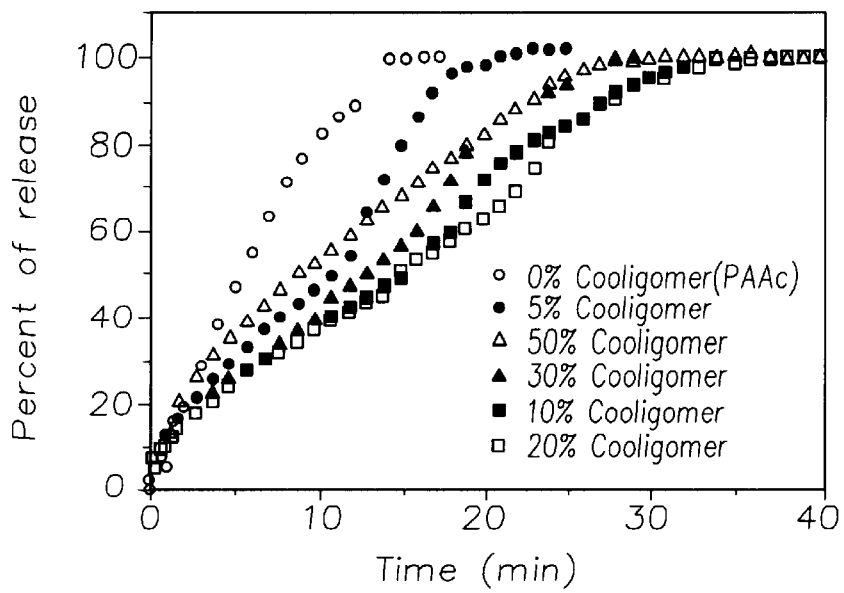
FIG. 13 illustrates the release of timolol from cast films of copolymer-drug mixtures for various graft copolymers of (NIPAAm-BMA)-g-AAc for various compositions of NIPAA-BMA co-oligomer in phosphate buffered saline (pH 7.4) at 34° C.

The drug release from copolymer-drug mixture films cast on glass disc is presented in FIG. 13. FIG. 13 compares the rates of release of timolol from cast films of drug complexes of graft copolymers [NIPAAm-BMA]-g-AAc of varying cooligomer NIPAAm-BMA content with homopoly AAc. The data presented compares drug release into phosphate buffered saline (pH 7.4) at 34° C. for copolymers derived from homopolyAAc with molecular weight 250,000 and cooligomer NIPAAm-BMA with molecular weight 3,100. The homopolyAAc reference had a molecular weight of 250,000.

The introduction of hydrophobic component units, BMA, into oligo NIPAAm lowers the thermally-induced phase transition temperature. As shown in FIG. 13, at physiologic temperature and pH, the cooligomer chain, NIPAAM-BMA, imparts hydrophobicity to the graft copolymer sufficient to significantly reduce the rate of drug release compared to homopolyAAc. However, the graft copolymers containing 20% or more cooligomer NIPAAm-BMA are too hydrophobic and therefore not erodible under the above conditions of drug release. The graft copolymers containing less than 20% cooligomer NIPAAm-BMA (i.e., 5% and 10% cooligomer) do erode and provide drug release over a prolonged period compared to homopolyAAc. Moreover, these grafted copolymers with lower content of pendant temperature-sensitive polymer components maintain bioadhesive properties sufficient to render these graft copolymer effective not only with respect to drug release, but also in relation to prolonged residence time in the treatment area. Accordingly, graft copolymers [NIPAAm-BMA]-g-AAc with cooligomer NIPAAm-BMA content between 5% and 20% are suitable for sustained release drug delivery and graft copolymers with coologimer content between 10% and 15% are preferred.

Example 4

Environmentally-Sensitive Hydrogels Comprising Temperature Sensitive and pH-Sensitive Homopolymer Components In this example, the synthesis and characterization, swelling, and drug loading and release properties of lightly cross-linked graft copolymers comprising a carboxylic acid-containing polymers backbone and with pendant temperature-sensitive polymer components. The cross-linked carboxylic acid-containing polymer was prepared followed by grafting of the temperature-sensitive polymer.

A. Synthesis and Characterization of Cross-linked Hydrogel NIPAAm-g-AAc

A series of hydrogels was prepared from AAc monomer solutions (40 weight % of AAc monomer) with a fixed amount of initiator, ammonium persulfate, and various amounts of cross-linker, ethylene glycol dimethylacrylate (EGDMA), in distilled water. The concentration of EGDMA was varied from 0.3%, 0.5%, 1.0%, to 2.0% by weight based on total AAc monomer. In a representative synthesis, the solution was degassed with nitrogen and injected into the 1.5 mm space between two glass plates. Polymerization was continued for 17 hours at 60° C. The resulting hydrogel sheet was washed by suspending the sheet in an ethanol bath for 48 hours. Disc-shaped hydrogels were obtained by cutting the gel sheet with a cork borer (15 mm diameter), followed by drying for 48 hours in air and for 24 hours under vacuum.

Figure 14:
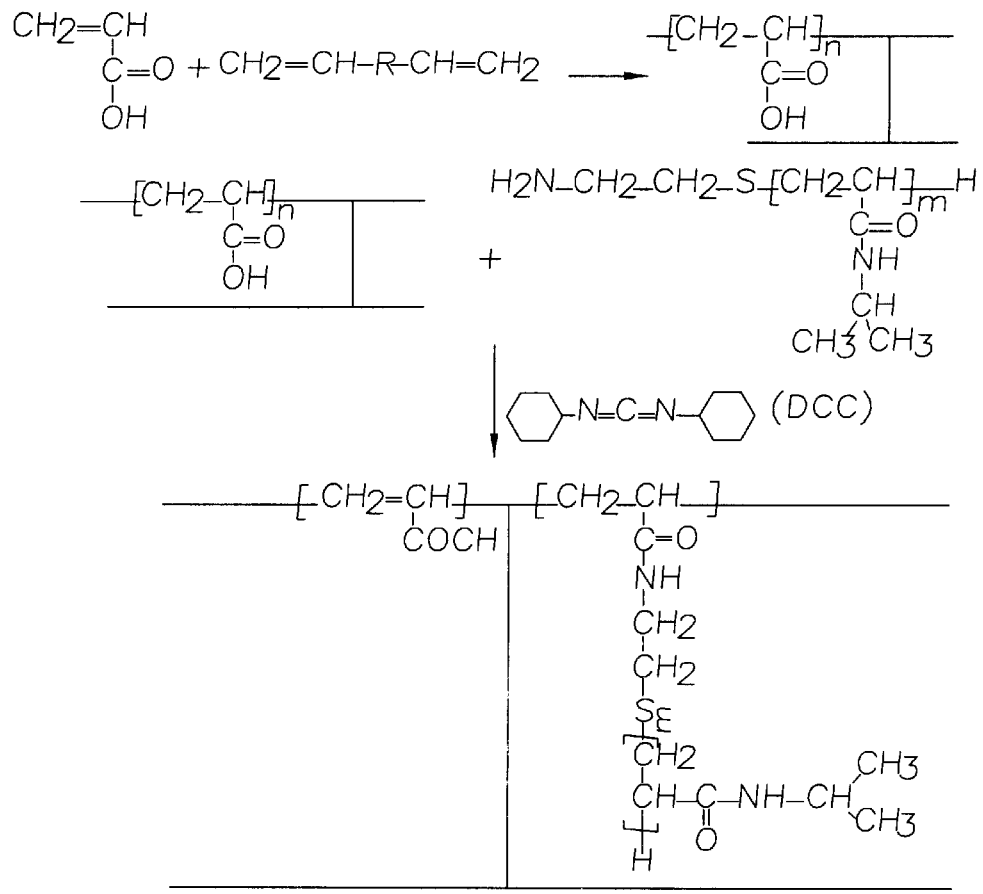
FIG. 14 illustrates the synthesis of a representative graft copolymer hydrogel of this invention.
Figure 15:
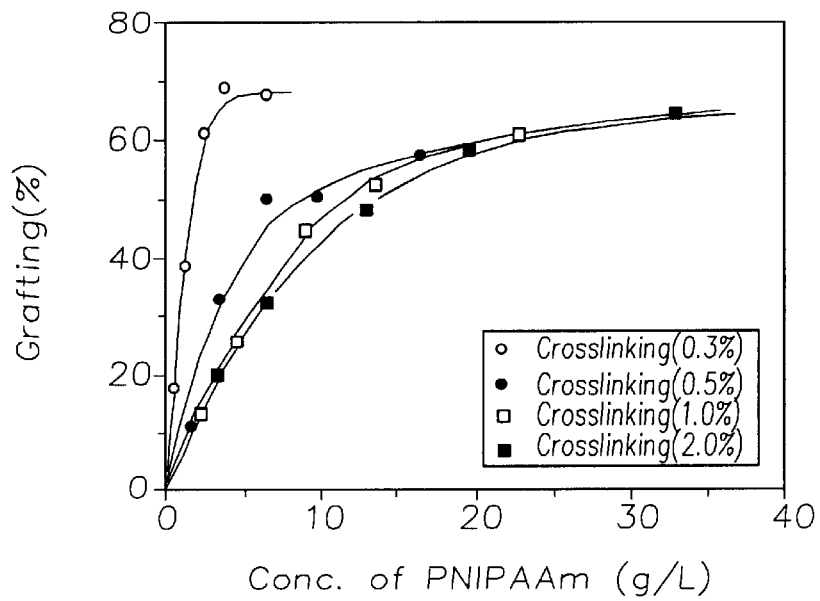
FIG. 15 illustrates the degree of grafting for representative graft copolymer hydrogels.

To graft the temperature-sensitive polymer component to the pH-sensitive cross-linked hydrogel, the dried gels prepared as described above, were swollen in methanol solutions containing varying amounts of amino-terminated NIPAAm, molecular weight 3,300 g/mol (solution concentrations from 0.65 g/L to 32.89 g/L). The swelling was carried out at room temperature for 48 hours. The uptake of amino-terminated NIPAAm by the gels was calculated from the equilibrium swollen volume of the gel. The hydrogel absorbed amino-terminated NIPAAM was then grafted (covalently coupled) to the polyAAc backbone by immersion of the hydrogel into a methanol solution containing a three-fold excess (relative to the amino-terminated NIPAAm) of coupling agent, dicyclohexylcarbodiimide (DCC). The coupling was carried out for 48 hours at room temperature. The resulting grafted hydrogel was washed with methanol and dried for 48 hours in air and for 24 hours under vacuum. The synthesis of the graft copolymer hydrogels is represented schematically in FIG. 14. The degree of grafting was determined by comparing the dry weight of the pure polyAAc hydrogel with the product grafted hydrogel. The degree of grafting is represented graphically in FIG. 15.

Generally, the percent grafting increased linearly with concentration of amino-terminated NIPAAm in solution with the initial reaction rate of the grafting being higher as the density of the cross-linking was decreased. A plateau of grafting level was reached for all samples.

B. Swelling of the Grafted Hydrogels

Figure 16:
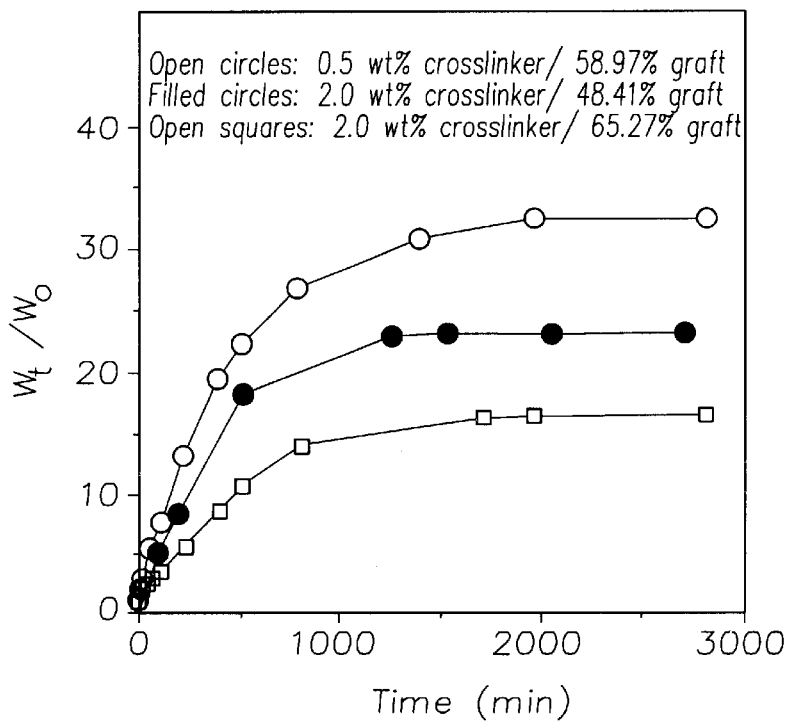
FIG. 16 illustrates the swelling ratios for representative graft copolymer hydrogels (open circle: 0.5 weight percent cross-linker, 58.97% grafting; filled square: 2.0 weight percent cross-linker, 48.41% grafting; open square: 2.0 weight percent cross-linker, 65.27% grafting).

To determine the swelling characteristics of the grafted hydrogels prepared as described above, grafted hydrogel discs were incubated in 0.05 M phosphate buffer solution containing 0.15 M sodium chloride at pH 7.4 at 34° C. A Lab-Line water shaker-bath was used for temperature control. In a representative determination, a solution of the grafted hydrogel was shaken at 150 rpm and the swelling weights of the hydrogels measured by weighing the sample at various times. The weights were measured after removing the gel from the buffer, and blotting adhered water with weighing paper. The swelling ratios were determined as the swollen weight/dried weight (Wt/Wo) and are presented in FIG. 16.

At high cross-link density, the greater the amount of grafted NIPAAm to the polyAAc, the slower the initial swelling rate. The slower rate is probably due to the increased hydrophobicity imparted to the graft hydrogel by the NIPAAm pendant chains. At low cross-link density, the uptake rates are more rapid, and the effect of grafting on these rates was less important.

C. Drug Loading and Release from Grafted Hydrogels

1. Drug Loading

Timolol hydrogen maleate was loaded into the graft copolymer hydrogel by swelling the hydrogel in the drug-methanol solution at room temperature for 24 hours. The drug-loaded hydrogels were dried for 24 hours in air and for 24 hours under vacuum. The drug loading was determined to be 2% by weight of the dried copolymer hydrogel.

2. Drug Release

Figure 17:
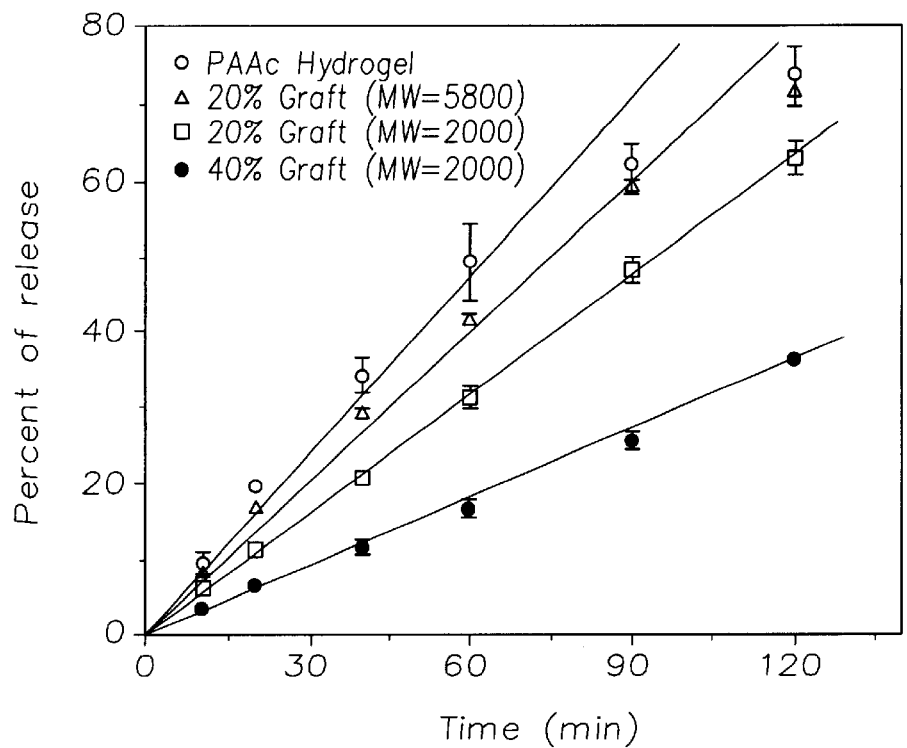
FIG. 17 illustrates the rate of release of timolol from cast films of copolymer-drug mixtures for several graft copolymer hydrogels of (NIPAAm-BMA)-g-AAc in phosphate buffered saline (pH 7.4) at 34° C.

Graft copolymer hydrogel drug release was determined as generally described in Example 1C2. The initial drug release rates are dependent upon the graft level and the length of the graft chains. The higher the graft level and/or the shorter the length of the graft chains, the slower the drug releases from the hydrogel. The release of drug from the graft copolymer hydrogel is presented in FIG. 17. As shown in FIG. 17, the greater degree of grafting or the lower the molecular weight of the pendant oligoNIPAAm, the slower the rate of drug release from the hydrogel.

Example 5

Random Copolymers Derived From Copolymerization of NIPAAm and AAc

For purposes of comparison to the environmentally-sensitive block and graft copolymers of the present invention, this example describes the synthesis, characterization, temperature-sensitive behavior, and drug loading and release properties of random copolymers derived from the polymerization of N-isopropylacrylamide (NIPAAm) and acrylic acid (AAc).

A. Synthesis and Characterization of Random Copolymers of NIPAAm and AAc

Random copolymers were synthesized by copolymerization of N-isopropylacrylamide and acrylic acid by standard radical polymerization procedures. Various random copolymers were prepared by varying the mole percent of NIPAAm monomer in the polymerization reaction. The synthesis of the random copolymer is represented schematically below.

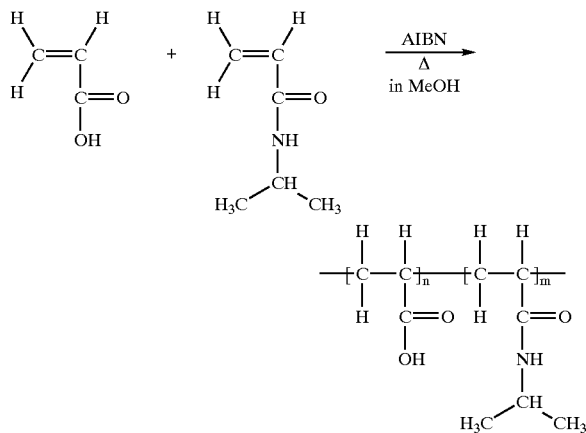

The synthetic results and the temperature-sensitive behavior of the ransom copolymers is summarized in Table 7.

TABLE 7

Synthesis and Temperature-Sensitive Properties of Random Copolymers

| $^f$NIPAAm (in monomer) | Polym. Time | Conversion | $^F$NIPAAm$^a$ (in copolymers) | | Mw$^b$ (× | LCST (° C.) | |
|---|---|---|---|---|---|---|---|
| mol % | (h) | (wt. %) | wt % | mol % | 10$^{-5}$) | pH 4.0 | pH 7.4 |
| 100 | 20.0 | 76.3 | 100 | 100 | — | 30.7 | 32.6 |
| 92 | 2.3 | 55.0 | 93 | 89 | — | 32.2 | 64.1 |
| 85 | 2.3 | 45.0 | 88 | 82 | — | 34.6 | >95 |
| 72 | 4.0 | 41.0 | 79 | 71 | 2.01 | 38.1 | >95 |
| 49 | 3.0 | 35.7 | 67 | 56 | 2.01 | 61.0 | >95 |
| 30 | 3.0 | 26.7 | 57 | 46 | 2.01 | >95 | >95 |
| 10 | 4.0 | 18.3 | 46 | 35 | 1.75 | >95 | >95 |

TABLE 7-continued

Synthesis and Temperature-Sensitive Properties of Random Copolymers

| $^f$NIPAAm (in monomer) | Polym. Time | Conversion | $^F$NIPAAm$^a$ (in copolymers) | | Mw$^b$ (× | LCST (° C.) | |
|---|---|---|---|---|---|---|---|
| mol % | (h) | (wt. %) | wt % | mol % | 10$^{-5}$) | pH 4.0 | pH 7.4 |
| 7 | 6.0 | 41.2 | 38 | 28 | 1.75 | >95 | >95 |
| 3 | 6.5 | 59.5 | 33 | 24 | 1.70 | >95 | >95 |

*Monomer concentration [NIPAAm + AAc] = 8.0% (w/v); concentration of initiator [AIBN] = 0.02% (w/v); solvent, methanol; polymerization temperature, 60° C.;
$^a$The composition of NIPAAm in copolymers was determined by conductometric titration with 0.1 N NaOH, which detects the caroxyl group from AAc monomer unit;
$^b$The molecular weight of the copolymers was determined by GPC using polyacrylamide as standard, water as an eluent.

Temperature-Sensitive Behavior of Random Copolymers

Figure 18:
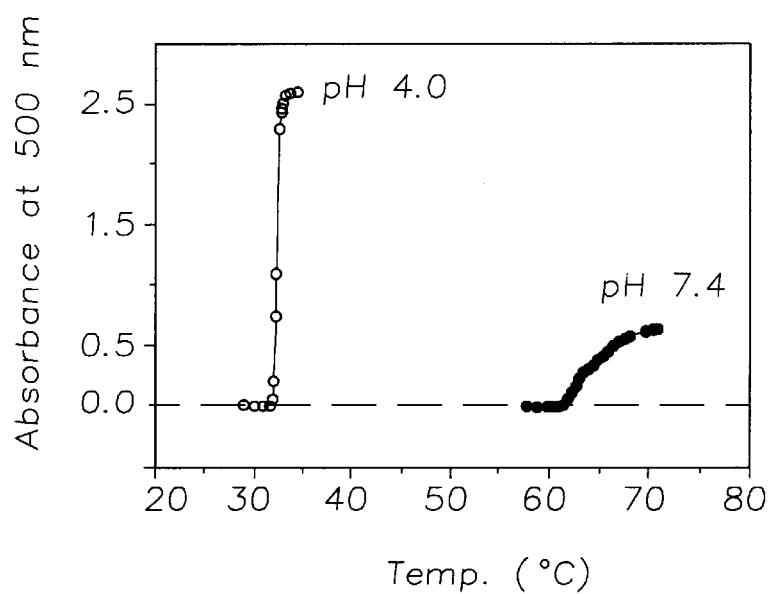
FIG. 18 illustrates the temperature-sensitive behavior of 0.2 weight percent solution of a random copolymer of NIPAAm and AAc (89 mole % NIPAAm) at pH 4.0 and pH 7.4.

The temperature-sensitive behavior of the random copolymers prepared as described above was investigated as generally described in Example 1B. The LCSTs for the random copolymers are summarized in Table 7 and the temperature-sensitive behavior for a random copolymer comprising 89 mole percent NIPAAM is illustrated in FIG. 18. The results show that random copolymers of NIPAAm and AAc with mole percents of AAc greater than about 10% do not undergo thermal phase separations at physiological pH (pH 7.4) or physiological temperature (34° C.). As illustrated in FIG. 18, the random copolymer does undergo a sharp phase transition at 31° C. at pH 4.0 and at 64° C. at pH 7.4.

Random copolymers as described above are ineffective in the practice of the present invention because the mole percent of AAc present in the random copolymer to achieve the requisite temperature-sensitivity reduces the bioadhesiveness of the copolymer below that effective for sustained drug release. Furthermore, for those random copolymers which do undergo phase transitions, either the temperature required for the phase transition or the pH is well outside physiological conditions.

C. Drug Loading and Release from Random Copolymers

1. Drug Loading

Generally, random copolymer-drug complexes were prepared as described in Example 1C1.

The random copolymer-drug particles were prepared by dissolving 0.5 g of polymer and 5 mg of timolol (feed ratio is 1 wt %) in 10 mL of methanol and then precipitating into 500 mL of diethyl ether. The precipitate was then dried under vacuum overnight. The drug content in the particles were determined by dissolving the particles to form a solution, and spectroscopically measuring the absorbance of the drug in the solution at 294 nm. The results of drug loading for the random copolymer prepared as described above and the graft copolymers prepared as described in Example 3 are presented in Table 8.

TABLE 8

Comparison of Random and Graft Copolymer Drug Loading

| | Polymer | | | | | |
|---|---|---|---|---|---|---|
| | Random copolymer | | | Graft copolymer | | |
| wt % NIPAAm in copolymer | 26 | 32 | 39 | 20 | 30 | 50 |
| Polymer added (g) | 0.5 | 0.5 | 0.5 | 0.5 | 0.5 | 0.5 |
| Drug added (mg) | 5.0 | 5.0 | 5.0 | 5.0 | 5.0 | 5.0 |
| Polymer recovery (% w/w) | 94 | 94 | 94 | 74 | 90 | 90 |
| Drug loaded (mg/g Polymer) | 9.4 | 9.2 | 9.1 | 9.9 | 10.0 | 10.8 |

2. Drug Release

Generally, the measurement of drug released from the random copolymer-drug particles was determined as described in Example 1C2. The drug release results for the various random copolymers are compared to graft copolymers of similar composition at 34° C. and 37° C. in FIGS. 4 and 5, respectively. The results show that drug release from the random copolymers at 34° C. is about twice as fast as release from the graft copolymers. For the random copolymers, the drug is completely released within 10 minutes. The results at 37° C. are qualitatively similar to those at 34° C., although complete release of drug takes about 24 minutes.

Example 6

Environmentally-Sensitive Graft Copolymers Comprising Temperature-Sensitive Copolymer and pH-Sensitive Homopolymer Components In this example, the synthesis and characterization, temperature-sensitive behavior, and drug loading and drug release properties of graft copolymers comprising temperature-sensitive copolymer and pH-sensitive homopolymer components are described. Specifically, the temperature-sensitive copolymer component is a block copolymer of ethylene oxide and propylene oxide ("EO/PO/EO"), and the pH-sensitive homopolymer component is a homopolymer of acrylic acid (AAc). The AAc homopolymer was utilized as the backbone of the graft copolymer.

A. Synthesis and Characterization of Graft Copolymers of EO/PO/EO-g-AAc

1. Synthesis of Amino-Terminal Block Copolymer of EO/PO/EO

Block copolymers of EO/PO/EO are commercially available as surfactants from BASF-Wyandotte Corp. (Wyandotte, Michigan) and sold under the tradename Pluronic.® Such block copolymers of EO/PO/EO have the following general structure:

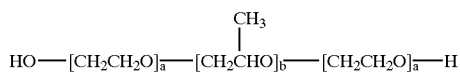

where the ratio of a:b:a varies as illustrated in the following Table 9:

TABLE 9

Block Copolymers of EO/PO/EO

| Pluronic ® | EO/PO/EO Ratio | Total M.W. (avg.) |
|---|---|---|
| L-61 | 4/30/4 | 2,000 |
| L-81 | 7/38/7 | 2,750 |
| L-92 | 10/50/10 | 3650 |
| L-122 | 13/69/13 | 5,000 |

Figure 19:
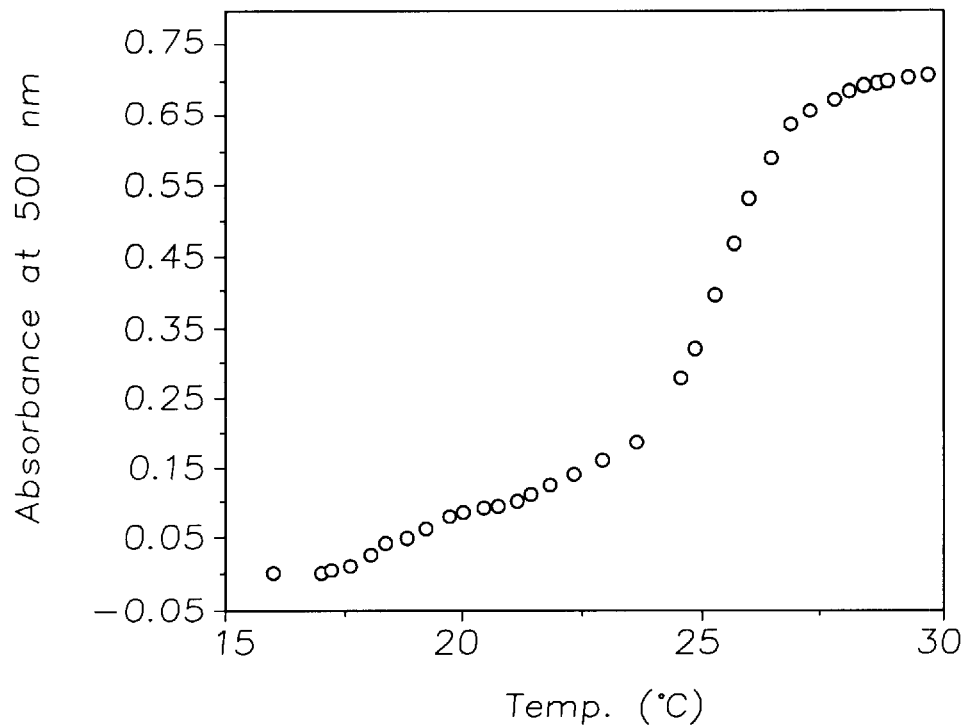
FIG. 19 illustrates the temperature-sensitive behavior of a 0.5 weight percent solution of a commercially available block copolymer of ethylene oxide and propylene oxide ("EO/PO/EO").

The LCST of Pluronic® L-122 was evaluated by measuring absorbance as a function of temperature. Specifically, a 0.5% by weight solution of L-122 (PBS buffer, pH 7.4) was prepared, and light absorbance (at 500 nm) was measured at temperatures ranging from 15° C. to 30° C. The LCST of the L-122 solution was found to be 26° C., and the results of this experiment are presented in FIG. 19.

The above block copolymers of EO/PO/EO were then derivatized to yield a reactive amino-terminal by a two step reaction First, 20 g of L-122 (4 mmole) was reacted with 1.0 g (5 mmole) of 4-nitrophenyl chloroformate in methyl chloride in the presence of triethylamine at room temperature for 4 hours to yield a 4-nitrophenyl formated-derivatized intermediate. This intermediate was recovered by extraction using petrolium ether for three times, resulting in 14 g of product with a yield of 72% by weight. In the second step, 10 g (2 mmole) of the intermediate was reacted with 0.36 g (6 mmole) of diaminoethlylene in methylene chloride at room temperature overnight. The amino-terminated L-122 derivative was recovered by extraction with petrolium ether for three times, dialysis against distilled water using a membrane with MW cut-off of 3500 for three days, and evaporated of water to obtain the product (8.8 g, yield of 88% by weight). Functionality of the amino-terminated derivative was determined by titration as 0.91±0.1.

The other block copolymers of EO/PO/EO were similarly derivatized to yield a reactive amino-terminal by the reaction scheme illustrated below.

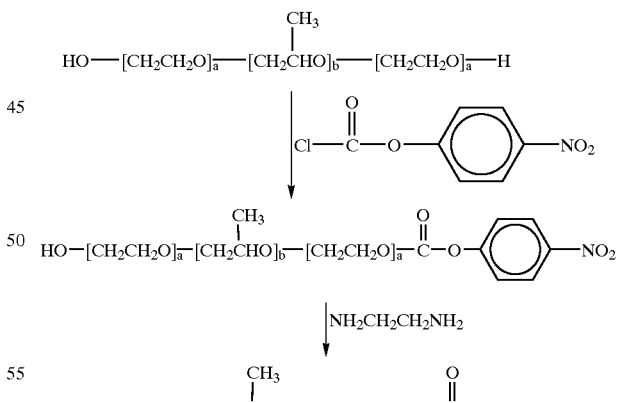

2. Synthesis of Graft Copolymers of EO/PO/EO-g-AAc

Graft copolymers of EO/PO/EO-g-AAc were prepared by coupling the reactive amino-terminals of the derivatized block copolymers of EO/PO/EO onto the homopolymer backbone of AAc. Specifically, reaction between the amino group of the amino-terminated EO/PO/EO derivative and a carboxyl group of AAc, in the presence of dicyclohexyl carbodiimide (DCC), resulted in amide bond formation. The reaction was carried out in methanol (100 mL) at room temperature for 24 hours, with a mole ratio of the block copolymer of EO/PO/EO to DCC of 2:1. Synthesis of the graft copolymers of EO/PO/EO-g-AAc is represented schematically below:

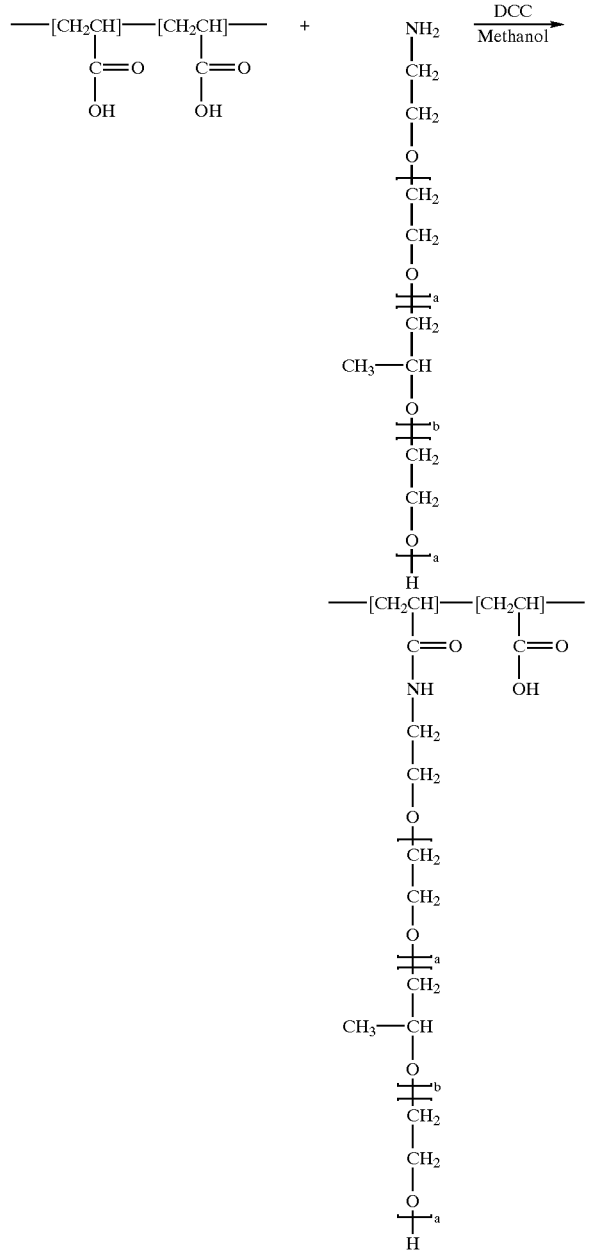

The resulting graft copolymers were recovered from the reaction solution by precipitation into THF or diethylether. Characterization of the graft copolymers was performed using GPC with Waters 500 Å, $10_3$ Å and $10_4$ Å Ultrastyrene® columns, DMF as mobile phase, at 40° C. and an elution rate of 0.7 mL/min., and the copolymer was analyzed by back titration with 0.1 N NaOH to determine the COOH groups in the PAAc backbone.

Graft copolymers were prepared at varying ratios of components, and using various block copolymers of EO/PO/EO as identified in Table 10.

TABLE 10

Graft Copolymers of Block EO/PO/EO and PolyAAc

| Pluronic ® | Pluronic ®/ PolyAAc | Yield (%) | Pluronic ® in Copolymer Component (wt %) |
|---|---|---|---|
| L-61 | 10/90 (wt %) | 79 | 15 |
| L-61 | 20/80 (wt %) | 55 | 24 |
| L-61 | 30/70 (wt %) | 86 | 34 |
| L-92 | 30/70 (wt %) | 94 | 32 |
| L-122 | 10/90 (wt %) | 80 | 15 |
| L-122 | 20/80 (wt %) | 80 | 18 |
| L-122 | 30/70 (wt %) | 68 | 21 |
| L-122 | 40/60 (wt %) | 78 | 27 |
| L-122 | 50/50 (wt %) | 65 | 41 |

B. Temperature-Sensitive Behavior of Graft Copolymers of EO/PO/EO-g-AAc

The graft copolymers of EO/PO/EO of this example form a translucent gel at approximately 32° C. Accordingly, rather than using an absorbance measurement for LCST, the solution-to-gel phase transition temperature was determined by measuring viscosity as a function of temperature by the following procedure. The copolymer component was analyzed by titration with 0.1 N NaOH to determine the COOH groups in the PAAc backbone.

A scintillation vial containing a stir bar was weighed, and 2.8 g of an aqueous solution containing 0.76% NaCl and 1.25% NaOH was added thereto. Next, 0.125 g of the L-122-30/70(wt %) graft copolymer was added, followed by 1.2 g of a 0.76% NaCl solution. The L-122-30/70(wt %) graft copolymer was dissolved by stirring the solution in an ice bath for about 2 hours, and then by keeping the scintillation vial in the refrigerator overnight. A sufficient amount of 1 N NaOH was added to the solution to yield a pH of 7.2. To this was added 0.05 g of 8.5% NaCl, and sufficient water was added to bring the solution to 5.0 g. The resulting solution contained 2.5% by weight of the L-122-30/70(wt %) graft copolymer, and had a pH of 7.2.

Figure 20:
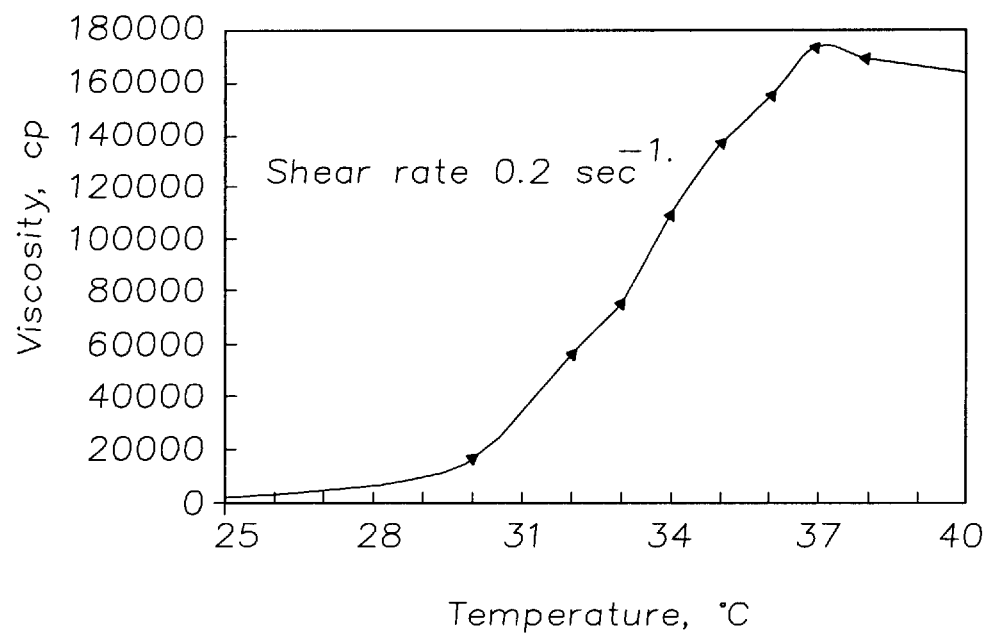
FIG. 20 illustrates the temperature-sensitive behavior of a 2.5 weight percent solution of a graft copolymer of the EO/PO/EO block copolymer of FIG. 19 grafted to a homopolymer backbone of AAc (i.e., EO/PO/EO-g-AAc).

The viscosity of the solution was then measured at various temperatures ranging from 25° C. to 40° C. using a Brookfield DV III RV viscometer fitted with a CP-52 spindle. The temperature was controlled by circulating water from a constant temperature water bath through the jacket of the viscometer cup. About 0.6 ml of the solution was placed in the viscometer cup. The viscosity measurements were carried out at 0.1 rpm (shear rate 0.2/second) for 3 minutes at a fixed temperature. The viscosity value at the end of 3 minutes was recorded, and the results of these measurements are presented in FIG. 20. As determined by this technique, the LCST of the L-122-30/70(wt %) graft copolymer was found to be 32° C. at 25% of maximum viscosity.

C. Drug Loading and Release from Graft Copolymers of EO/PO/EO-g-AAc

Drug loading and release from the copolymer-drug mixture was determined by casting a film of a copolymer-drug mixture (containing 5% by weight timolol maleate) on a glass disk as disclosed in Example 1C2. In these experiments, the thickness of the films was ca. 150μ, the diameter was ca. 0.54–0.58 mm, and the weight of each film was ca. 5 mg. The coated glass discs were suspended in PBS buffer (pH 7.4) at 34° C., and the amount of drug release was measured as a function of time. The results of this experiment are presented in FIGS. 21, 22 and 23.

Figure 21:
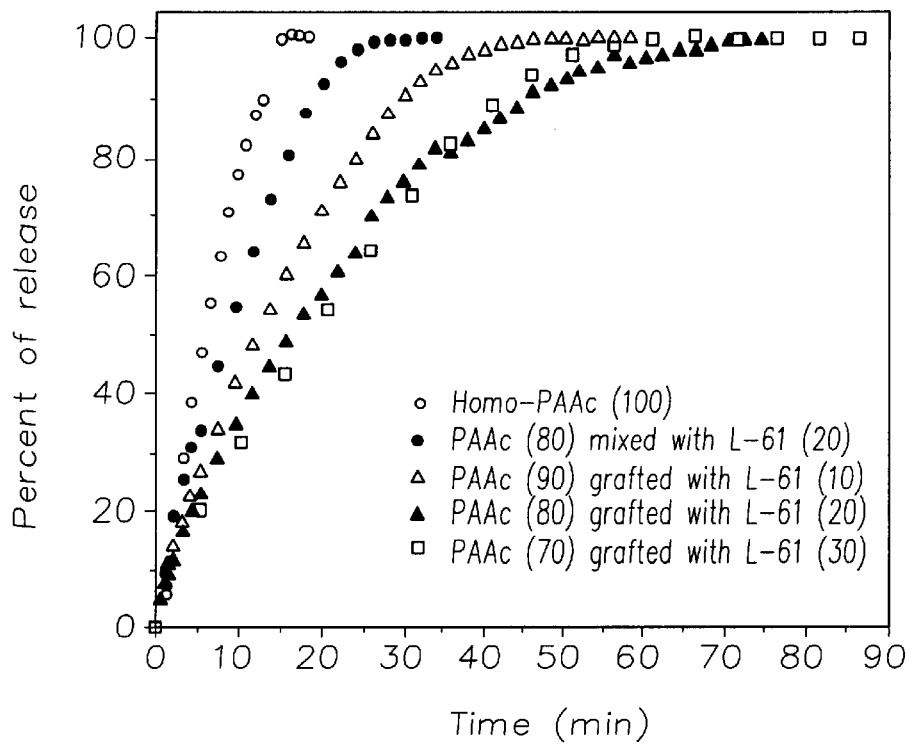
FIG. 21 illustrates the drug release (timolol maleate) from graft copolymers of EO/PO/EO-g-AAc at varying ratios of EO/PO/EP to AAc (i.e., 10:90, 20:80 and 30:70). For comparison purposes, drug release from a homopolymer of AAc, and a physical mixture of the AAc homopolymer and a EO/PO/EO block copolymer, are also illustrated.

Specifically, FIG. 21 illustrates drug release from graft copolymers of EO/PO/EO-g-AAc at varying ratios of EO/PO/EO to AAc (i.e., 70% AAc grafted with 30% L-61, 80% AAc grafted with 20% L-61, and 90% AAc grafted with 10% L-61). For comparison purposes, drug release from a homopolymer of AAc (i.e., 100% AAc), as well as a physical mixture of 80% homopolymer AAc and 20% L-61, are also presented in FIG. 21. In this example, graft copolymers of EO/PO/EO and AAc showed significantly retarded drug release profiles compared to the AAc homopolymer alone or the physical mixture of the same with L-61. Moreover, complete drug release was delayed to over 1 hour when the content of L-61 was 20% (or higher) compared to AAc.

Figure 22:
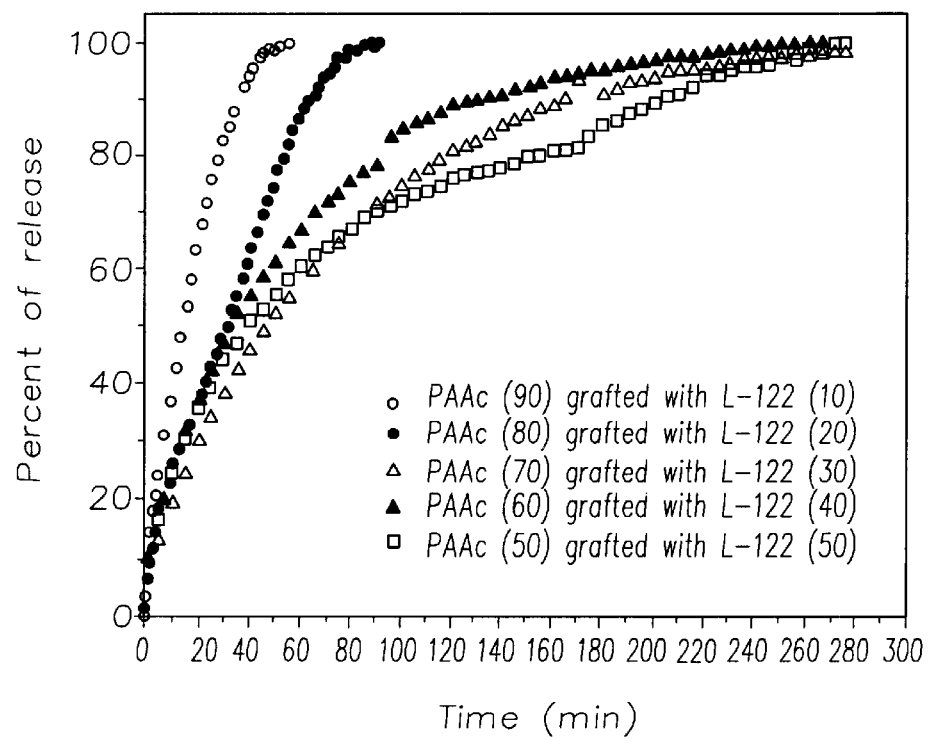
FIG. 22 illustrates drug release from graft copolymers of the O/PO/EO block copolymer L-122 grafted to a homopolymer backbone of AAc at ratios of EO/PO/EO to AAc ranging from 10:90 to 50:50.

FIG. 22 illustrates drug release from graft copolymers utilizing L-122 as the block copolymer of EO/PO/EO. In this experiment, graft copolymers of L-122-g-AAc at ratios varying from 90% AAc/10% L-122 to 50% AAc/50% L-122 were employed. With 30% (or more) L-122 grafted to AAc, complete drug release time was more than 4 hours.

Figure 23:
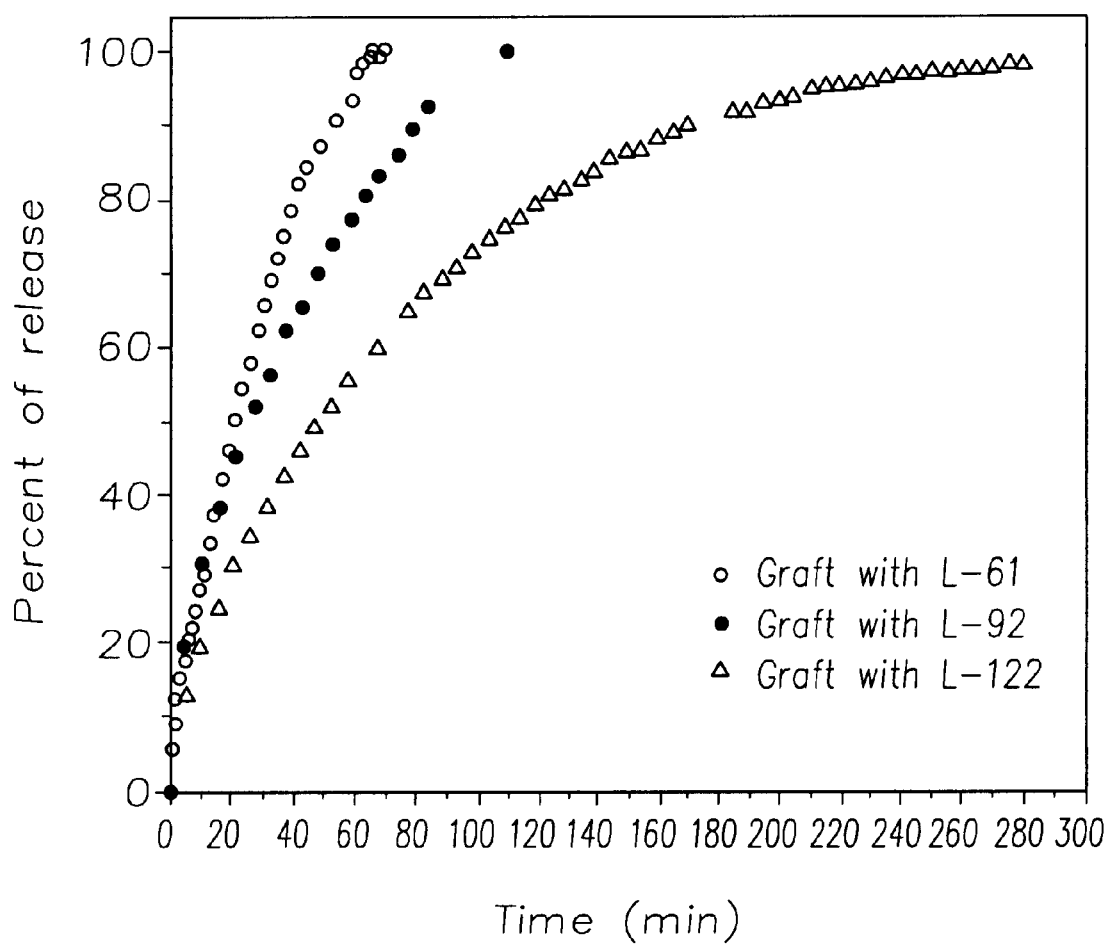
FIG. 23 illustrates drug release from graft copolymers of various EO/PO/EO block copolymers (i.e., L-61, L-92 and L-122) grafted to a homopolymer backbone of AAc at a ratio of EO/PO/EO to AAc of 30:70.

Lastly, FIG. 23 illustrates the drug release properties associated with the use of different block copolymers of EO/PO/EO—that is, L-61, L-92 and L-122. Graft copolymers of 70% AAc and 30% L-61, L-92 or L-122 were tested. The block copolymer L-122, when grafted to the AAc backbone, resulted in a prolonged drug time of over four hours. In addition, a physical mixture of a temperature-sensitive polymer (such as the Pluronic® L-122) with a copolymer-drug mixture of this invention may, in certain instances, prolong drug release therefrom, and is within the scope of the present invention.

Example 7

Environmentally-Sensitive Graft Copolymers Comprising Temperature-Sensitive Homopolymer and Temperature-Sensitive Triblock Copolymer Components In this example, the synthesis and temperature-sensitive behavior of graft copolymers comprising a temperature-sensitive homopolymer component and a temperature-sensitive triblock copolymer component is described. The graft copolymers described in this example exhibit dual temperature sensitivity.

A Synthesis of Graft Copolymer Pluronic®-g-PNIPAAm

In this example, the preparation of a graft copolymer comprising two temperature-sensitive polymer components is described. The two polymer components have different phase transition temperatures: the backbone polymer component, polyN-isopropylacylamide (PNIPAAm), has a phase transition temperature around 32° C., and the pendant polymer component, a triblock copolymer of ethylene oxide and propylene oxide (trade name Pluronic®), has the cloud point around 20° C. The graft copolymer was synthesized by free radical copolymerization of NIPAAm with a macromonomer of Pluronic®.

1. The Synthesis of a Macromonomer of Pluronic®

A macromonomer of Pluronic® was synthesized by reaction of one hydroxy end group of the Pluronic® with acrylol chloride in the presence of triethylamine using methylene chloride as solvent. In a typical preparation, 23.2 g (4.64 mmol) of Pluronic® L-122 was dissolved in 80 mL of methylene chloride, to which 4.5 mL of triethylamine was added. The mixture was cooled to 0° C. and 0.55 g of acryloyl chloride (6.03 mmol) was added dropwise to the mixture with vigorous stirring. The reaction was maintained at 0° C. for one hour and then overnight at room temperature.

The resulting reaction mixture was filtered to remove the insoluble salt formed during the reaction and the solvent was removed from the filtrate by distillation. The crude semi-solid product was washed with three 200 mL portions of n-hexane and dried in vacuo. The product macromonomer was obtained (13.5 g, 56% yield) and used without further purification in the following copolymerization. The synthesis of a representative macromonomer of Pluronic® is presented schematically below.

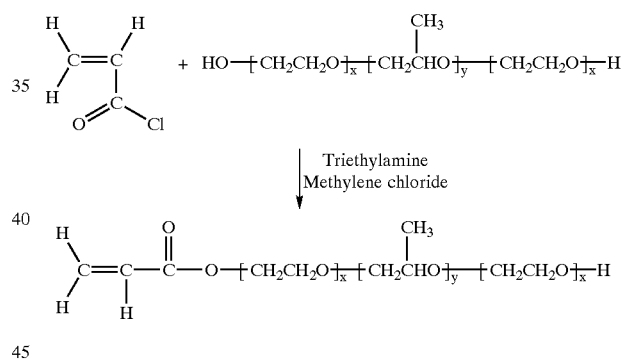

2. The Synthesis of Graft Copolymer Pluronic®-g-PNIPAAm

The graft copolymer Pluronic®-g-PNIPAAm was prepared by copolymerization of NIPAAm with the macromonomer of Pluronic® prepared as described above. In a representative polymerization, to a solution of 3.0 g of Pluronic® L-122 macromonomer and 7.0 g of NIPPAAm in 60 mL of methanol was added 50 mg of AIBN. The resulting solution was degassed by three freeze-pump-thaw cycles. The polymerization reaction was carried out at 60° C. under nitrogen atmosphere for 1 h. The graft copolymer product was recovered by precipitating the reaction mixture into diethyl ether, a suitable solvent for Pluronic®, and the precipitate was washed with diethyl ether and dried under vacuum to yield 1.72 g (17.2%) of the product graft copolymer. The synthesis of a representative graft copolymer comprising temperature-sensitive polymer components is presented schematically below.

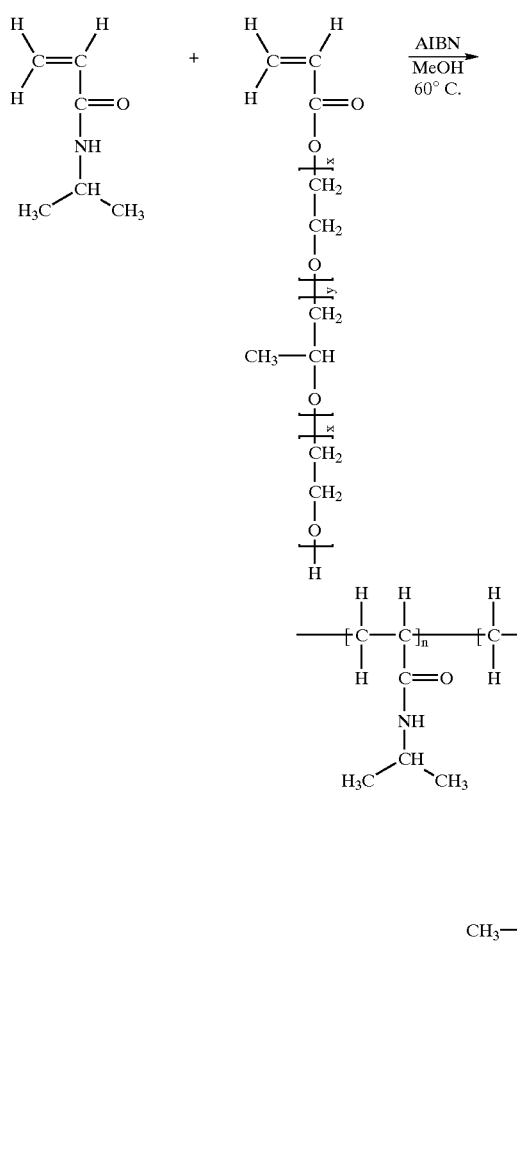

B. Temperature-Sensitive Behavior of the Graft Copolymer

Figure 24:
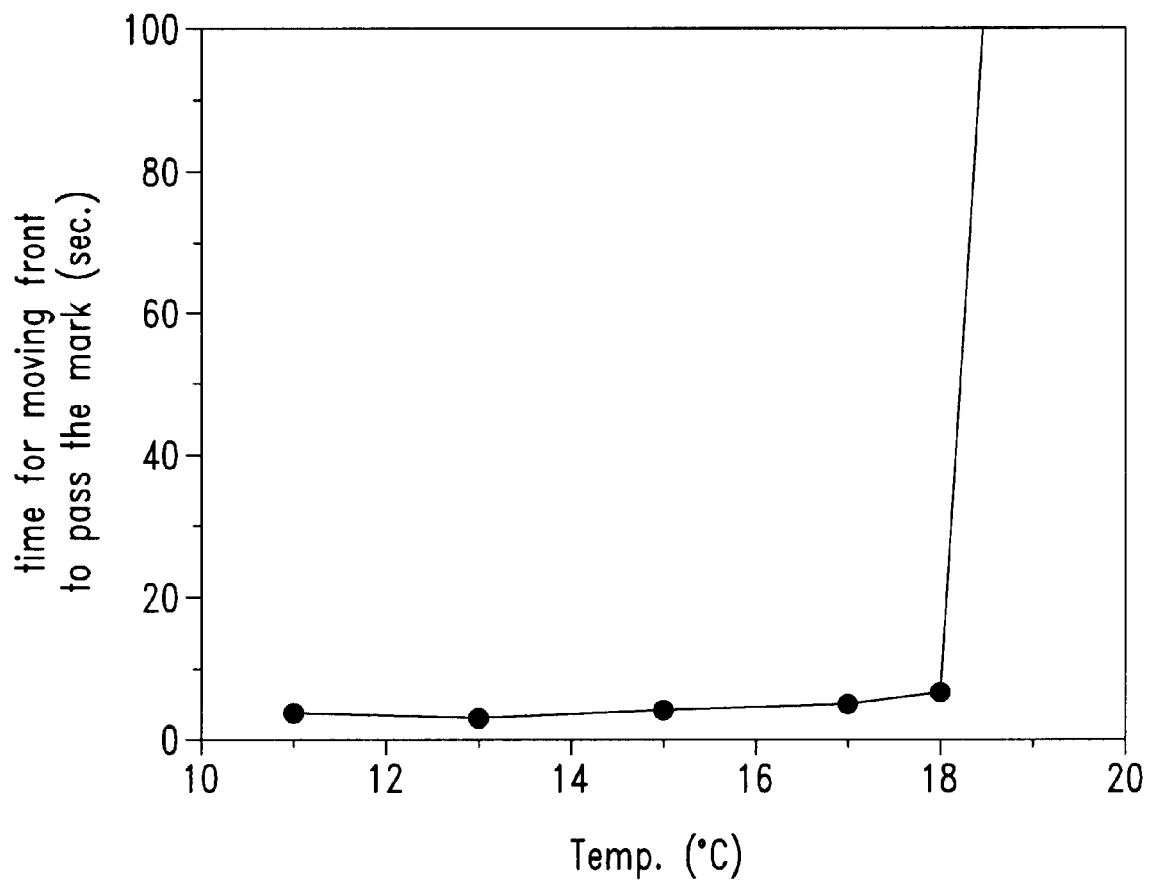
FIG. 24 illustrates the mobility of a representative graft copolymer solution (7% Pluronic®-g-PNIPAAm by weight in distilled, de-ionized water) as a function of temperature.

The thermal sensitivity of graft copolymer Pluronic®-g-PNIPAAm prepared as described above was determined by solution mobility. The polymer solution used for the mobility determination was a 7 wt % aqueous polymer solution prepared by dissolving the polymer in distilled de-ionized water at 4° C. At this temperature, a clear and viscous, but mobile solution was obtained. The mobility of the solution changed with temperature. To measure the mobility change with temperature, the solution in a test tube was placed in a water bath in which the temperature was increased at a rate of 0.6° C./min. At a various temperatures, the test tube containing the solution was removed from the bath and placed on a downward slope such that the liquid solution would move downwards along the tube wall. The time required for the moving front to pass a predesignated mark on the tube wall was recorded as a function of bath temperature. FIG. 24 illustrates the mobility change of the solution (i.e., the time required for the moving front to pass the tube wall mark as a function of temperature). Referring to FIG. 24, at 19° C. (the cloud point of 1% Pluronic® L-122 in water) the copolymer solution completely loses its mobility and a transparent gel was formed. By continuing to increase the temperature to the phase transition temperature of PNIPAAm (33–34° C.) the gel sharply changed from transparent to opaque.

To summarize, an aqueous solution of Pluronic®-g-PNIPAAm graft copolymer exhibited two clear temperature-sensitivities: the first at 19° C. where the copolymer solution showed temperature-induced gellation behavior due to the hydrophobic interaction of the polypropylene oxide (PPO) segment in the Pluronic(D polymer component resulting in physical crosslinking; and the second at 32–34° C. where the transparent gel became opaque due to the phase transition of the PNIPAAm leading to the collapse of the backbone. These two transitions are reversible.

Example 8

Environmentally-Sensitive Graft Copolymer Hydrogels Comprising pH-Sensitive Polymer Components In this example, the synthesis, pH-sensitive behavior, and drug loading and release properties of graft copolymer hydrogels comprising pH-sensitive polymer components is described. For purposes of comparison, the synthesis, pH-sensitive behavior, and drug loading and release properties of random copolymer hydrogels, prepared from the same monomers as the above mentioned graft copolymer hydrogels, is also described. The copolymer hydrogels described in this example exhibit dual pH sensitivity.

A. Synthesis of Graft Copolymer Hydrogels: PNVF-g-PAAc and PVA-g-PAAc

Graft copolymer hydrogels having dual pH sensitivity were synthesized from pH-sensitive polymer components. In these graft copolymer hydrogels, one polymer component contained pH-sensitive carboxylic acid groups (—$CO_2H$), and the other polymer component contained pH-sensitive amino groups (—$NH_2$). The carboxylic acid-containing polymer component was polyacrylic acid (PAAc) formed from the carboxylic acid-containing monomer acrylic acid (AAc). The amino-containing polymer component was poly vinyl amine (PVA), formed by the hydrolysis of the formamide groups of poly N-vinylformamide (PNVF). The PNVF was formed from N-vinylformamide (NVF), a formamide-containing monomer.

1. The Synthesis of Graft Copolymer Hydrogels

The dual pH-sensitive graft copolymer hydrogels were prepared by basic hydrolysis of the polymer product formed from free radical copolymerization of a PNVF macromonomer and acrylic acid in water using ammonium persulfate as an initiator and methylene bisacrylamide as a crosslinker. The macromonomer of PNVF was prepared from the reaction of amino-terminated PNVF and acryloxy succinimide.

a. The Synthesis of Amino-Terminated Poly (N-vinyl formamide) (PNVF)

An amino-terminated PNVF was synthesized by free radical chain transfer polymerization of NVF. In a representative experiment, 14.4 g (0.2 mmol) of NVF, 0.164 g (1 mmol) of AIBN, and 0.454 g (4 mmol) of AET-CL were dissolved in 50 mL of aqueous dimethylformamide ($H_2O$:DMF, 40:10). The solution was degassed by three freeze-pump-thaw cycles and the polymerization reaction was carried out at 60 ° C. under nitrogen atmosphere for two hours. After the polymerization, the solution was adjusted to pH 11 with 0.1 N NaOH. The polymer product was collected by precipitation of the solution into ethanol. The resulting precipitate was collected by filtrated, washed with ethanol, and dried under vacuum to provide 11.56 g (80%) of amino-terminated PNVF. The molecular weight of the polymer was measured by titration with 0.01 N CL and determined to be 16,700. The polymerization results are summarized in Table 11.

TABLE 11

The Synthesis of Amino-Terminated PNVF*

| Code | $M_{NVF}/M_{AET\text{-}HCl}$ | Product (g) | Yield (%) | Mn |
|---|---|---|---|---|
| NVF-1 | 100:2 | 11.56 | 80 | 16700 |
| NVF-2 | 100:4 | 10.67 | 74 | 10500 |
| NVF-3 | 100:8 | 9.95 | 69 | 3800 |

*Solvent; $H_2O$/DMF (4:1), 50 mL; Initiator; AIBN, 0.164 g; polymerization temperature: 60° C.; polymerization time: 2 h.

The synthesis of a representative amino-terminated polymer is presented schematically below.

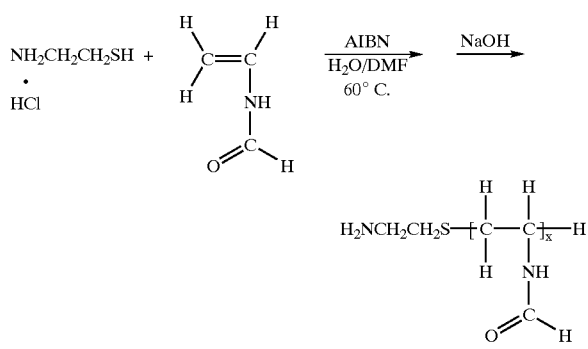

b. The Synthesis of a Macromonomer of Poly(N-Vinylformamide) (PNVF)

The macromonomer of PNVF was prepared by reaction of the terminal amino group of the amino-terminated polymer of PNVF prepared as described above with acryloxyl succiniimide (AS) (Eastman-Kodak Co., Rochester, N.Y.). In a representative preparation, to 5.0 g of the amino-terminated PNVF (Mn 10,500) in 45 mL of water was added 1 mL of an AS solution in DMSO containing 0.625 g of AS. The reaction was stirred at room temperature for 4 h. The macromonomer product was isolated by precipitating the reaction solution into ethanol and collecting the precipated product by filtration. The product thus obtained was then dried under vacuum to yield 4.5 g (90%) of PNVF macromonomer.

The synthesis of a representative macromonomer of PNVF is presented schematically below.

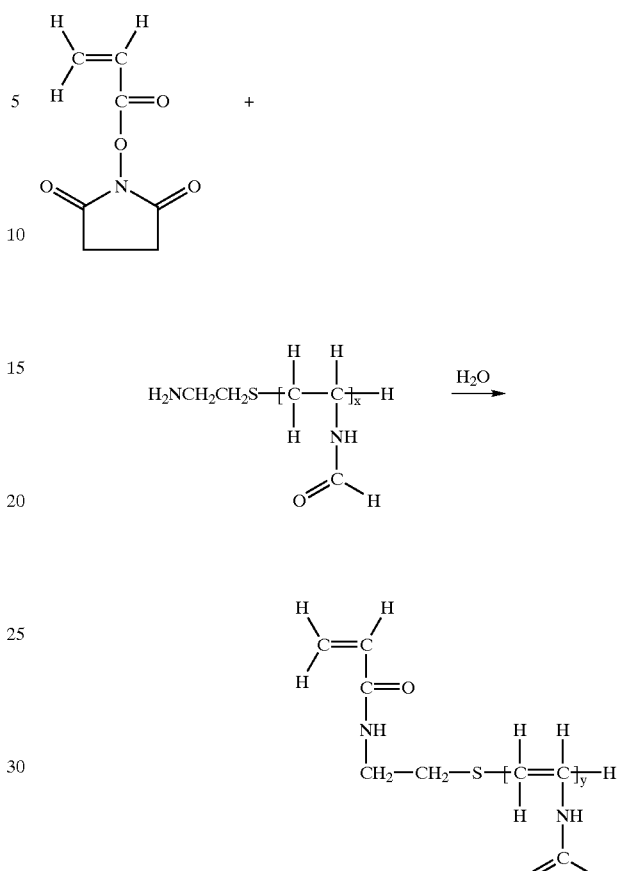

c. Copolymerization Reaction: The Synthesis of PNVF-g-PAAc Hydrogel

The PNVF-g-PAAc graft copolymer hydrogel was prepared by free radical copolymerization of PNVF macromonomer, prepared as described above, with AAc in water using ammoniumpersulfate (($NH_4)_2S_2O_8$) as initiator, methylene biscacrylamide (MBAAm) as crosslinker. In a representative copolymerization, 1.5 g of PNVF macromonomer, 1.5 g of AAc, 30 mg of MBAAm and 30 mg of ($NH_4)_2S_2O_8$ were dissolved in 10 mL of distilled, deionized water. After the solution was degassed by bubbling nitrogen through the solution for 5 min, the solution was poured into a glass mold (two glass plates separated with a 1.5 mm spacer). The polymerization was carried out at 60° C. overnight after which the resultant gel was separated from the glass mold.

No swelling of the gel was observed when placed in distilled, de-ionized water at room temperature and the gel was opaque, probably due to the strong H-bonding between the COOH in the backbone and the NH—CHO in the graft chain.

When the gel was placed in glycine buffer (20 mM), pH 9.0, the gel swelled greatly and became transparent. The swollen gel was cut into discs of 5 mm diameter for further swelling tests.

The synthesis of a representative PNVF-g-PAAc graft copolymer hydrogel is presented schematically below.

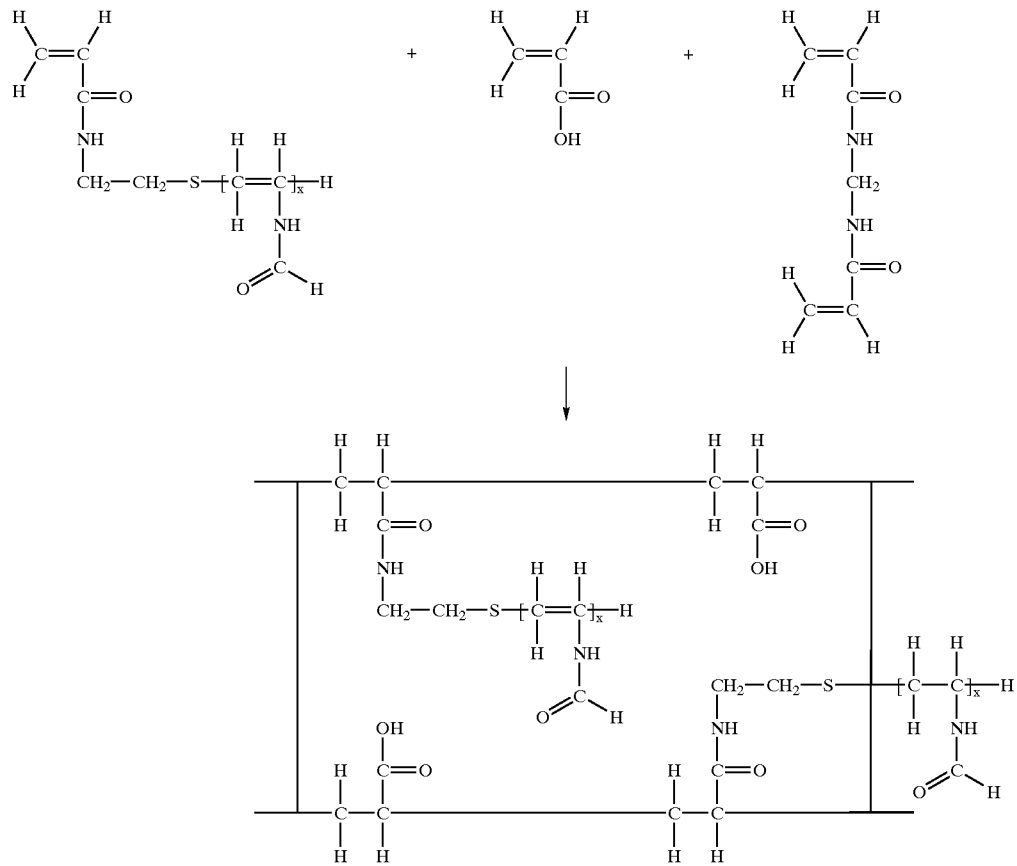

d. Amide Hydrolysis: The Synthesis of PVA-,i-PAAc Hydrogel

The PVA-g-PAAc hydrogel was synthesized by basic aqueous hydrolysis of the PNVF-g-PAAc hydrogel prepared as described above. The PNVF-g-PAAc gel was immersed in aqueous 0.1 N NaOH solution for 2 h, warmed up to 40° C., and maintained at this temperature overnight. The gel was then rinsed with distilled de-ionized water and cut into discs of 8 mm diameter. These disc gels were stored in distilled-deionized water for further swelling, drug loading and release tests.

The synthesis of a representative PVA-g-PAAc graft copolymer hydrogel is presented schematically below.

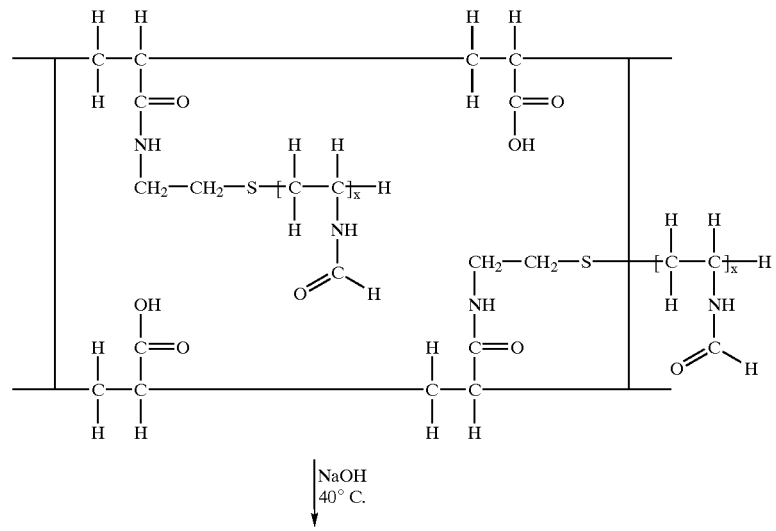

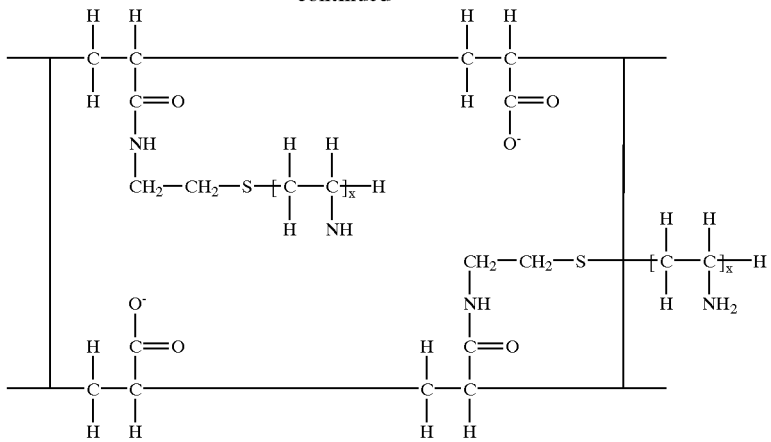

B. Synthesis of Random Copolymer Hydrogels: NVF-AAc and VA-AAc

Random copolymer hydrogels prepared by the copolymerization of carboxylic acid-containing monomer acrylic acid (AAc) and the amino-containing (after formamide hydrolysis) monomer N-vinylformamide (NVF) were synthesized to compare their properties with the graft copolymer hydrogels formed from the same monomers.

The graft copolymer hydrogel NVF-AAc was prepared by standard copolymerization of the NVF and AAc monomers under the conditions described above. The product acrylic acid-N-vinylformaide hydrogel (NVF-AAc) was then hydrolyzed to the acylic acid-vinyl amine hydrogel (VA-AAc) also as described above.

The synthesis of a representative random copolymer NVF-AAc hydrogel and its conversion to a representative random copolymer VA-AAc hydrogel is presented schematically below.

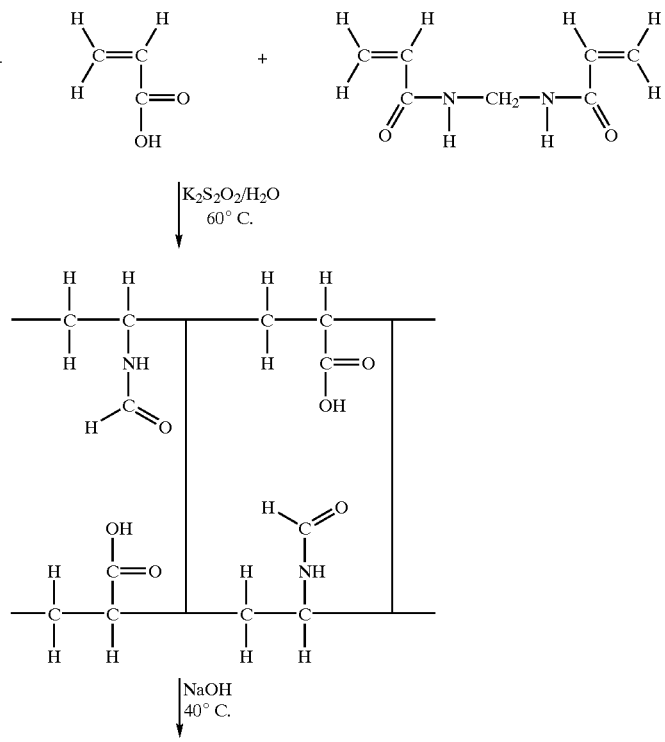

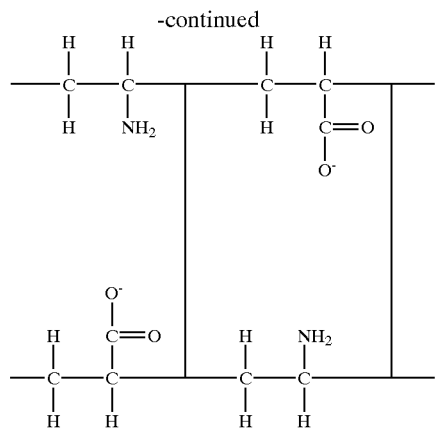

C. Swelling Behavior of Grafted Hydrogels

Figure 25A:
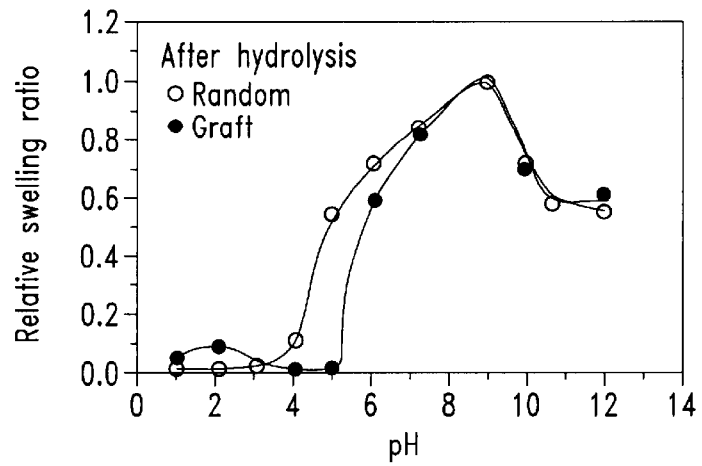
FIG. 25 illustrates the relative swelling ratios of graft and random copolymer hydrogels as a function of pH: (A) graft and random copolymer hydrogels (i.e., PVA-g-PAAc and VA-AAc) after hydrolysis; (B) graft and random copolymer hydrogels (i.e., PNVF-g-PAAc and NVF-AAc) prior to hydrolysis; and (C) graft copolymer hydrogels (i.e., PNVF-g-PAAc and PVA-g-PAAc) prior to and after hydrolysis.
Figure 25B:
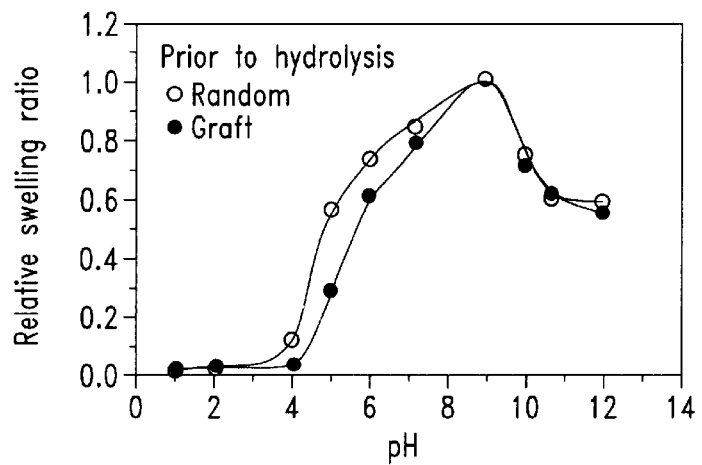
Figure 25C:
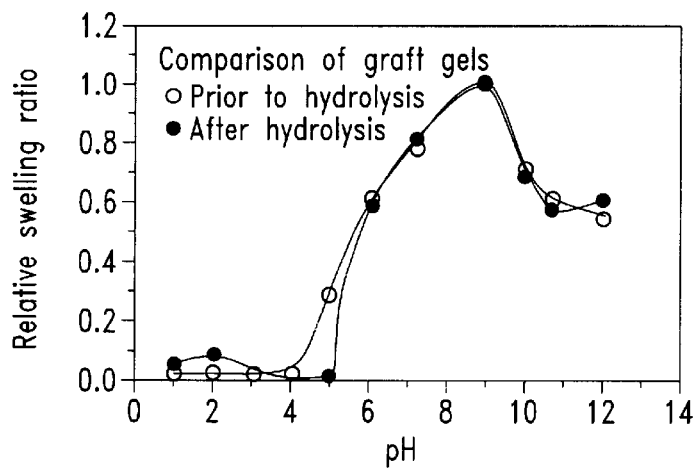

The swelling characteristics of the graft copolymer hydrogels prepared as described above was determined as described in Example 4B. The relative swelling ratios of these hydrogels as a function of pH is presented in FIG. 25. FIG. 25 compares the swelling ratios of (A) the graft and random copolymer hydrogels after hydrolysis, i.e., PVA-g-PAAC and VA-AAc; (B) the graft and random copolymer hydrogels prior to hydrolysis, i.e., PNVF-g-PAAC and NVF-AAc; and (C) the graft copolymer hydrogels prior to and after hydrolysis, i.e., PNVF-g-PAAC and PVA-g-PAAc.

D. Drug Loading and Release from Grafted Hydrogels

1. Drug Loading

A representative drug, lysozyme, was loaded into the graft copolymer hydrogels prepared as described above. The hydrogels were treated with lysozyme solutions of various concentrations in 20 mM sodium phosphate buffer (PB), pH 7.4. Hydrogel discs equilibrated in 20 mM PB, pH 7.4, were immersed in 15 ml of a lysozyme solution with shaking for 36 hours at room temperature. The lysozyme loaded gels were then removed from the loading solution and rinsed with PB three times to remove the surface lysozyme. The hydrogel lysozyme loading results are presented in FIG. 26.

Figure 26:
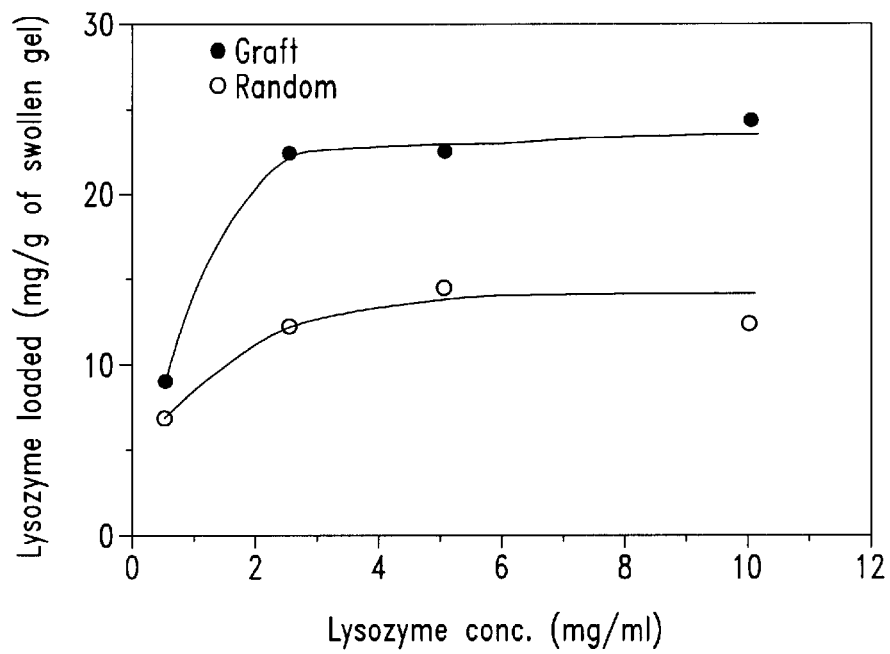
FIG. 26 illustrates the amount of lysozyme loading into graft and random copolymer hydrogels (i.e., PVA-g-PAAc and VA-AAc) as a function of lysozyme concentration (lysozyme loading conditions: phosphate buffer, pH 7.4, room temperature, 36 h).

Referring to FIG. 26, the lysozyme loading capacity in the representative PVA-g-PAAc graft copolymer hydrogel is much higher than that in the VA-AAc random copolymer hydrogel. The result indicates that the graft copolymer gels have a greater affinity to lysozyme than the random copolymer hydrogels. The greater affinity of lysozyme for the graft copolymer may be due to the unique negatively charged backbone of the graft copolymer which could form a strong ionic interaction with the high positively charged drug. At high lysozyme concentration of the loading solution (e.g. >2.5 mg/ML), saturated drug loading was observed for both gels.

2. Drug Release

Release of lysozyme from the loaded hydrogels was determined as generally described in Example 1C2. In the procedure, the loaded hydrogel discs were placed into a release medium (10 ml of PBS or MES buffer per gel disc). The release systems were shaken at room temperature and 1.0 mL aliquots were removed at specific time intervals (upon removal of the 1.0 ml aliquots, 1.0 ml of fresh release medium was added to the system). The lysozyme concentration in the aliquot was determined by the UV absorbance at 280 nm. The drug release results are presented graphically in FIG. 27.

Figure 27:
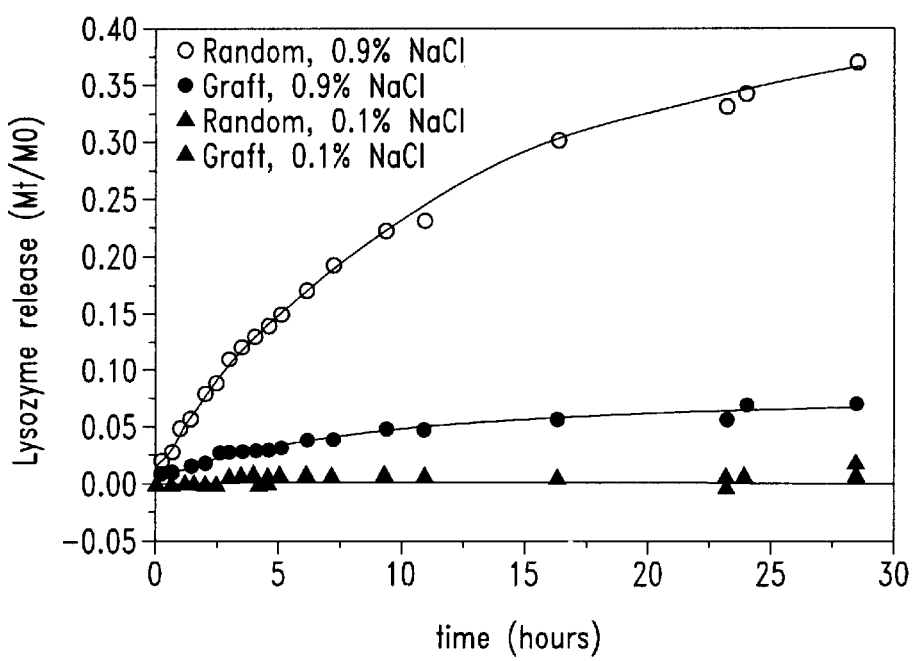
FIG. 27 illustrates lysozyme release from graft and random copolymer hydrogels (i.e., PVA-g-PAAc and VA-AAc) at pH 5.0 at 0.1% and 0.9% sodium chloride at room temperature as a function of time (hydrogels were loaded in 2.5 mg/mL lysozyme solution).
Figure 28:
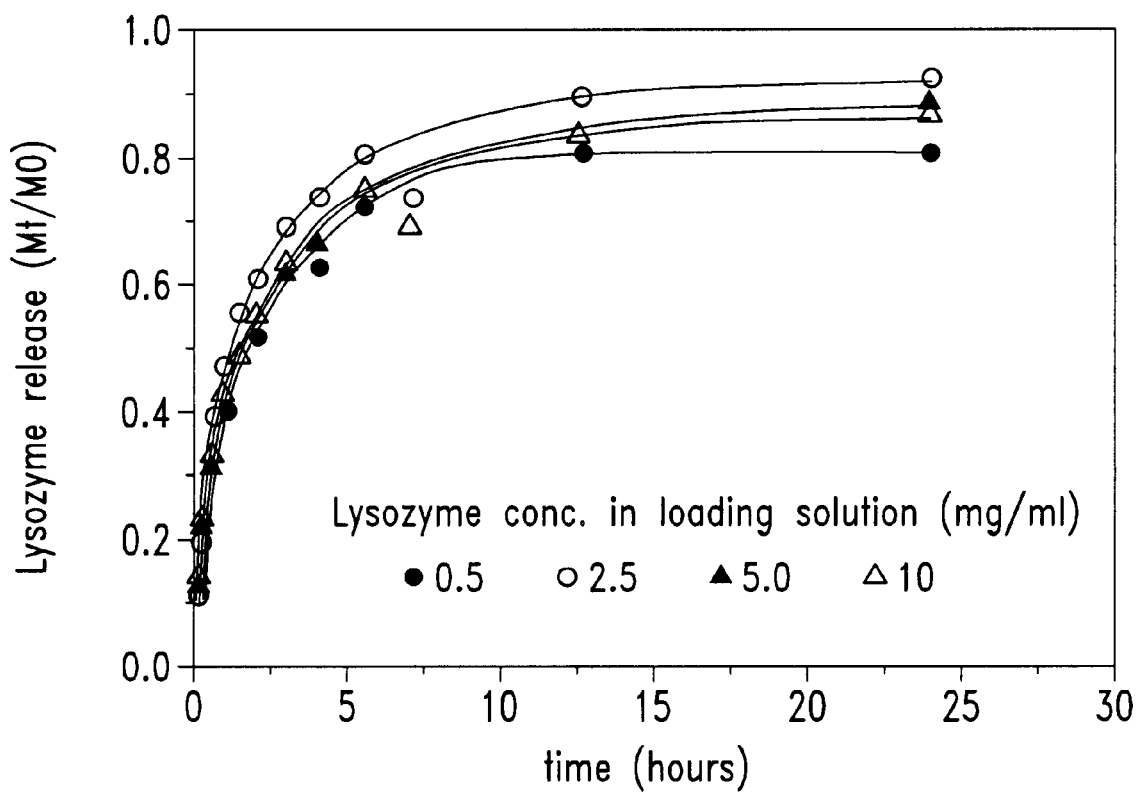
FIG. 28 illustrates lysozyme release from random copolymer hydrogels (i.e., VA-AAc) in phosphate buffer, pH 7.4 at room temperature as a function of time.
Figure 29:
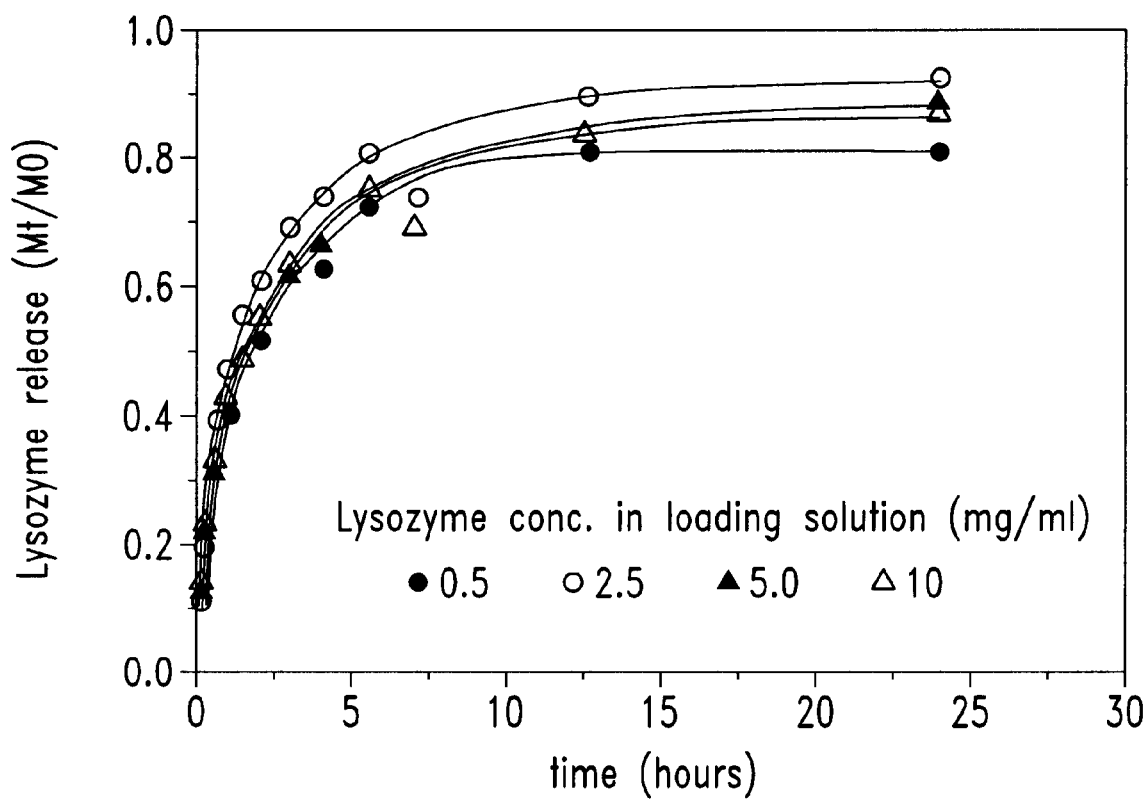
FIG. 29 illustrates lysozyme release from graft copolymer hydrogels (i.e., PVA-g-PAAc) in phosphate buffer, pH 7.4 at room temperature as a function of time.

Referring to FIG. 27, at pH 5.0, with low salt concentration (e.g., 0.1%), the lysozyme was not released from either of those hydrogels, suggesting that the drug release from those hydrogels follows ionic exchange mechanism. At increased salt concentration, the lysozyme was released from the hydrogels. The release rate was determined to depend upon hydrogel structure. The rate of release of lysozyme from the PVA-g-PAAc hydrogel was significantly slower than the release rate for the random copolymer gel. This difference in release rate may be attributable to the pH sensitivities as depicted by the pH profile as shown in FIG. 25A. At pH 5.0, the PVA-g-PAAc hydrogel is fully deswelled due to the strong ionic interaction between positively charged amino groups, $-NH_3^+$, of the graft chain and the negatively charged carboxylic acid groups, $-COO-$ of the backbone. In contrast, at pH 5.0, the random copolymer hydrogel is swelled. Release of surface lysozyme from the graft hydrogel may result in the formation of a dense gel surface due to the strong ionic interaction between the negatively charged $COO^-$ in the backbone and positively charged $-NH_3^+$ in the graft chain, thus slowing the drug release from within the gel. Such a dense surface is not formed on the random copolymer hydrogel surface as evidenced by the data as shown in FIG. 25A. The release of lysozyme from VA-AAc random copolymer hydrogel and PVA-g-PAAc graft copolymer hydrogel are presented in FIGS. 28 and 29, respectively. Referring to these figures, lysozyme release from both gels in the PBS buffer, pH 7.4 follow the same kinetics regardless of the loading capacity.

Figure 30:
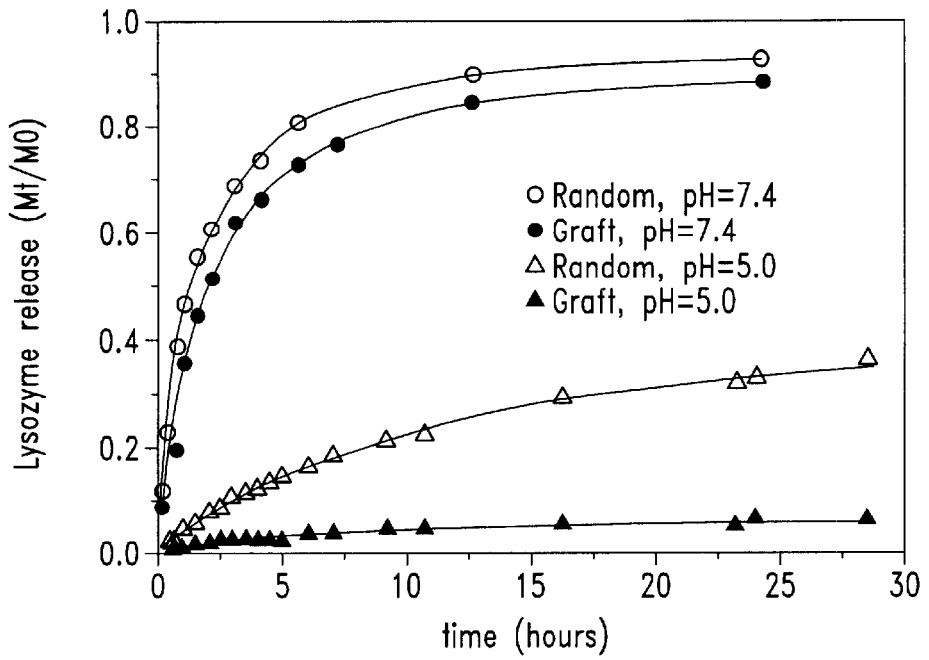
FIG. 30 illustrates lysozyme release at room temperature from graft and random copolymer hydrogels (i.e., PVA-g-PAAc and VA-AAc) at pH 5.0 and pH 7.4 as a function of time.

FIG. 30 compares the release of lysozyme from these graft and random copolymer hydrogels at different pHs. Referring to FIG. 30, release of lysozyme from the hydrogels at pH 7.4 (PBS buffer) is significantly greater than release at pH 5.0 (MES buffer). The difference in release rate suggests that, in addition to the ionic exchange drug release mechanism, drug diffusion from the gel may play an important role. The results for the graft copolymer hydrogel are particularly characteristic of the drug difflusion mechanism. In brief, drug diffusion from within the gel is dependent-upon the degree of gel swelling. The greater the gel swelling, the greater the diffusion of the drug from the gel. Referring to FIG. 25A, at pH 7.4, both the graft and random copolymer hydrogels have similar swelling ratios. However, at pH 5.0, the swelling ratios are significantly different where the swelling ration for the random copolymer hydrogel is greater than for the graft copolymer hydrogel. Accordingly, as illustrate in FIG. 30, drug release at pH 7.4 is greater than release at pH 5.0.

Example 9

Graft Copolymer-Drug Compositions

In this example, graft copolymer-drug compositions and drug release therefrom is disclosed. The copolymer-drug composition includes a graft copolymer having a pH-sensitive homopolymer component and a temperature-sensitive tri-block copolymer component (i.e., Pluronic®-g-PAAc prepared as described in Example 6A); a drug (i.e., nonoxynol-9, "N-9," a contraceptive drug); and a carrier (i.e., an aqueous solution of distilled, de-ionized water and dilute aqueous sodium hydroxide). The copolymer-drug composition optionally includes a free temperature-sensitive copolymer (i.e., Pluronic® L-122). The compositions were formulated for vaginal administration of the contraceptive drug nonoxynol-9.

A. Graft Copolymer Pluronic®-g-PAAc - Nonoxynol-9 Compositions

The graft copolymer-nonoxynol compositions were prepared by dissolving the copolymer (i.e., Pluronic®-g-PAAc containing 34 weight % Pluronic® L-122) and nonoxynol-9 (i.e., IGEPAL®CO630, Rhone-Poulenc) in distilled, deionized water at 4° C. followed by adjusting the pH to 5.4 (i.e., vaginal pH) with 0.1 N aqueous sodium hydroxide. The concentration of copolymer in all compositions was 1.5 weight %, and the concentration of nonoxynol-9 varied from 0.15 to 6.0 weight %. To enhance the gellation of the compositions upon warming to physiological temperature, in some instances free Pluronic® L-122 was added. For comparative purposes, a homopolymer PAAc-nonoxynol composition was also prepared. In addition, Conceptrol®, a commercial nonoxynol-containing contraceptive product from Ortho Pharmaceutical Corporation, was also used as a control composition.

The compositions prepared as described above are summarized in Table 12.

TABLE 12

Polymer-Nonoxynol Compositions

| Composition | Polymer | Polymer wt % | Nonoxynol wt % | Pluronic ® L-122 wt % |
|---|---|---|---|---|
| 1 | Graft | 1.5 | 0.15 | 0 |
| 2 | Graft | 1.5 | 0.30 | 0 |
| 3 | Graft | 1.5 | 0.60 | 0 |
| 4 | Graft | 1.5 | 0.60 | 0.30 |
| 5 | Graft | 1.5 | 0.60 | 0.60 |
| 6 | PAAc | 1.5 | 0.60 | 0 |
| 7 | — | — | 4.0 | — |

B. Nonoxynol Release from Polymer Compositions

Release of nonoxynol from the compositions prepared as described above was determined as generally described in Example 1C2. In the procedure, 1.0 mL of the polymer-nonoxynol composition was added to a 20 mL vial (i.d. 2.3 cm) and incubated at 37° C. for 5 min. followed by the addition of 10 mL of buffer, pH 5.4. The release systems were shaken (shaking rate of 150 rpm) at 37° C. and 1.0 mL aliquots were removed at specific time intervals (upon removal of the 1.0 ml aliquots, 1.0 ml of fresh release medium was added to the system). The nonoxynol concentration in the aliquot was determined by the UV absorbance at 268 nm. The drug release results are presented in FIGS. 31 and 32.

Compositions 1–6 were mobile liquids at 4° C. However, upon warming to 37° C., gelling occurred for compositions 1–5. Composition 6, the PAAc polymer composition, remained mobile. In the absence of free Pluronic® L-122, the gel strength of the compositions (i.e., compositions 1–3) decreased with increasing nonoxynol concentration. The result suggests that nonoxynol strongly disturbs the gellation of the polymer-drug composition. At constant nonoxynol concentration (i.e., compositions 3–5), the gel strength increases with increasing free Pluronic® L-122 concentration. The result suggests that compositions containing free Pluronic® L-122 may enhance the gellation of the polymer-drug composition. The overall results suggest that the decrease in gel strength that occurs upon increasing nonoxynol concentration may be balanced or reversed by the addition of sufficient quantities of free Pluronic® L-122. With regard to the control compositions, no gellation was observed for composition 6, the physical mixture of PAAc and nonoxynol, and Conceptrol® remained a thick gel regardless of the temperature.

Figure 31:
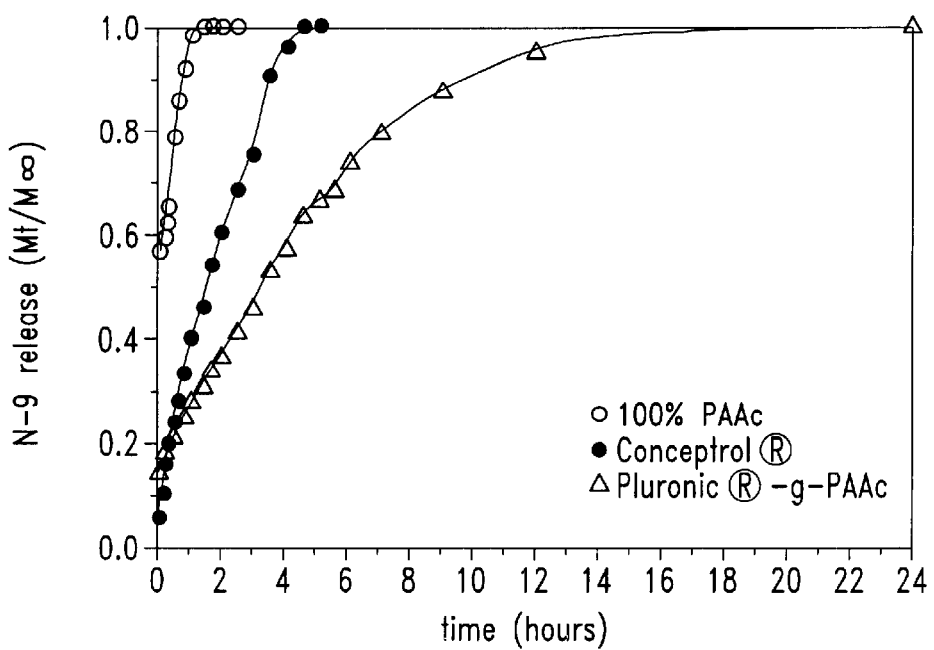
FIG. 31 illustrates nonoxynol 9 release (37° C.) from Pluronic®-g-PAAc, 100% PAAc and Conceptrol®.

The graft copolymer-nonoxynol compositions provide sustained nonoxynol release. Referring to FIG. 31, release from the graft copolymer compositions is significantly slower than release from either the homopolymer PAAc composition or Conceptrol®. For example, the time required for the release of 80 weight % of nonoxynol from Conceptrol® is 3 hours, while the same release from the graft copolymer composition requires 7 hours. Nonoxynol release from the homopolymer PAAc composition, which does not gel, is essentially instantaneous.

Figure 32:
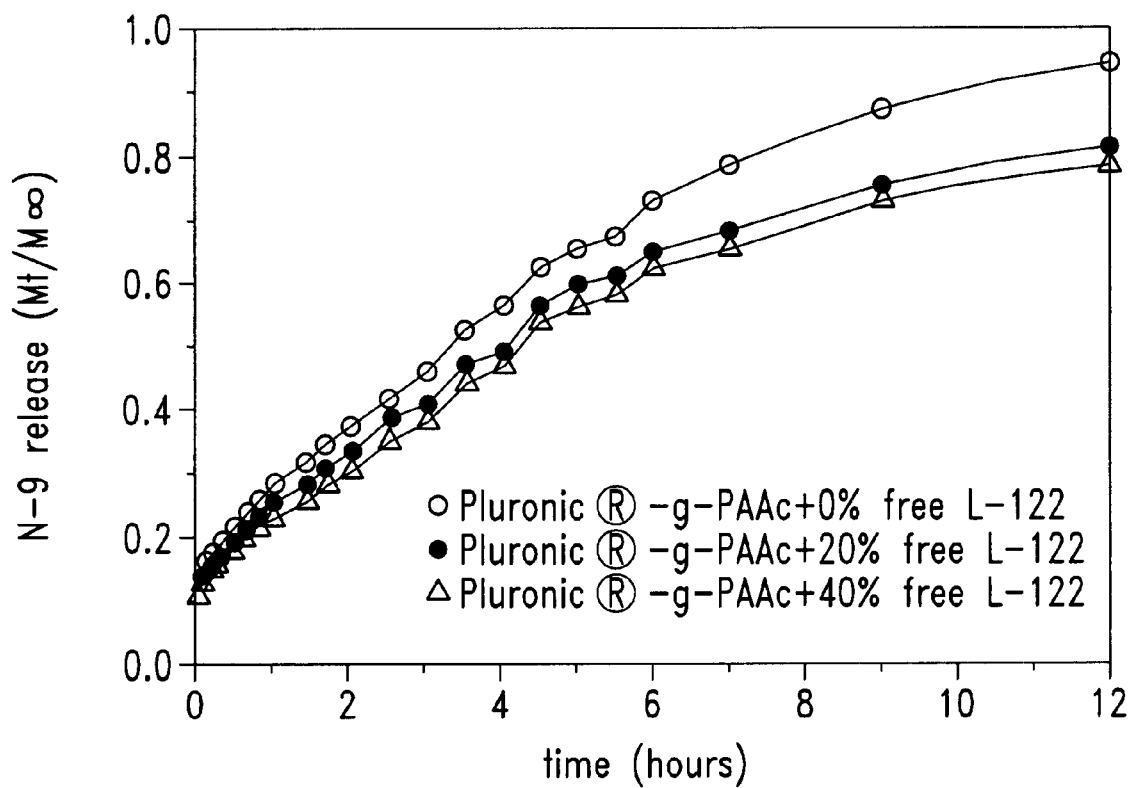
FIG. 32 illustrates nonoxynol 9 release (37° C.) from 0%, 20% and 40% L-122 and Pluronic®-g-PAAc.

The graft copolymer-nonoxynol compositions containing free Pluronic® L-122 have a prolonged sustained release of nonoxynol. Referring to FIG. 32, the addition of free Pluronic® L-122 to the graft copolymer composition decreases the rate of nonoxynol release. For example, the time required for the release of 70 weight % of nonoxynol from a graft copolymer composition containing no free Pluronic® L-122 is about 5 hours. The time required for comparable release from graft copolymer compositions containing 20% and 40% free Pluronic® L-122 is about 8.5 and 12 hours, respectively. The results indicate that the greater the amount of free Pluronic® L-122 added to the graft copolymer composition, the slower the rate of release of nonoxynol from the composition.

In addition to the graft copolymer compositions described above, a graft copolymer that remains gelled at pH 5, but swells at pH 7, may be used to release nonoxynol upon contact with semen within the vagina. Semen is basic and upon contact with such a graft copolymer-nonoxynol gel within the vagina at pH 4–5, the pH environment changes and becomes more neutral. Upon the change of pH toward neutrality, the graft copolymer gel swells and the sustained release of nonoxynol commences. Thus, the release of the contraceptive drug is timed with the need for the contraceptive event (i.e., the presence of semen within the vagina). Graft copolymers having pH-sensitive backbone and pH-sensitive pendant polymer components, including those described in Example 8, have such a pH-sensitive property and be effective in contraceptive copolymer compositions.

From the foregoing, it will be appreciated that, although specific embodiments of this invention have been described herein for the purposes of illustration, various modifications may be made without departing from the spirit and scope of the invention. Accordingly, the invention is not limited except by the appended claims.

What is claimed is:

1. A graft copolymer comprising a backbone pH-sensitive polymer component with a pendant temperature-sensitive polymer component grafted thereto, wherein the graft copolymer has a critical temperature ranging from 20° C. to 40° C. measured at a pH between 6.0 to 8.0, wherein the temperature sensitive polymer component is a block copolymer, and wherein the pH-sensitive polymer component comprises a carboxylic acid-containing polymer.

2. A graft copolymer comprising a backbone pH-sensitive polymer component with a pendant temperature-sensitive polymer component grafted thereto, wherein the graft copolymer has a critical temperature ranging from 20° C. to 40° C. measured at a pH between 6.0 to 8.0, wherein the temperature sensitive polymer component is a random or block copolymer, the pH-sensitive polymer component comprises a carboxylic acid-containing polymer, and at least one of the pH-sensitive or temperature-sensitive polymer components is lightly cross-linked with crosslinker molecules.

3. A graft copolymer comprising a backbone temperature-sensitive polymer component with a pendant pH-sensitive polymer component grafted thereto wherein the graft copolymer has a critical temperature ranging from 20° C. to 40° C. measured at a pH between 6.0 to 8.0, wherein the temperature sensitive polymer component is a block copolymer, and wherein the pH-sensitive polymer component comprises a carboxylic acid-containing polymer.

4. A graft copolymer comprising a backbone temperature-sensitive polymer component with a pendant pH-sensitive polymer component grafted thereto, wherein the graft copolymer has a critical temperature ranging from 20° C. to 40° C. measured at a pH between 6.0 to 8.0, wherein the temperature sensitive polymer component is a random or block copolymer, the pH-sensitive polymer component comprises a carboxylic acid-containing polymer, and at least one of the pH-sensitive or temperature-sensitive polymer components is lightly cross-linked and the graft copolymer is a hydrogel.

5. The graft copolymer of any one of claims 1, 2, 3 or 4 wherein the critical temperature is a lower solution critical temperature.

6. The graft copolymer of any one of claims 1, 2, 3 or 4 wherein the critical temperature is a melting temperature.

7. The graft copolymer of any one of claims 1, 2, 3 or 4 wherein the critical temperature is a glass transition temperature.

8. The graft copolymer of any one of claims 1, 2, 3 or 4 wherein the critical temperature is determined at a pH between 7.0 to 7.8.

9. The graft copolymer of any one of claims 1, 2, 3 or 4 wherein the critical temperature ranges from 26° C. to 34° C.

10. The graft copolymer of any one of claims 1, 2, 3 or 4 wherein the critical temperature ranges from 28° C. to 32° C.

11. The graft copolymer of any one of claims 1, 2, 3 or 4 wherein the carboxylic acid-containing polymer is derived from polymerizable carboxylic acids selected from the group consisting of acrylic acid, methacrylic acid, ethacrylic acid, β-methylacrylic acid, cis-α-methylacrylic acid, trans-α-methylcrotonic acid, α-butylcrotonic acid, α-phenylacrylic acid, α-benzylacrylic acid, α-cyclohexylacrylic acid, β-phenylacrylic acid, coumaric acid and umbellic acid.

12. The graft copolymer of any one of claims 1, 2, 3 or 4 wherein the carboxylic acid-containing polymer is carboxymethylcellulose.

13. The graft copolymer of any one of claims 1, 2, 3 or 4 wherein the pH-sensitive polymer, component is a homopolymer.

14. The graft copolymer of claim 13 wherein the homopolymer is polyacrylic acid.

15. The graft copolymer of any one of claims 1, 2, 3 or 4 wherein the pH-sensitive polymer component is a random or block copolymer.

16. The graft copolymer of claims 1 or 3 wherein the temperature-sensitive polymer component is a block copolymer.

17. The graft copolymer of claim 16 wherein the block copolymer comprises poly(N-isopropylacrylamide).

18. The graft copolymer of claims 1 or 2 wherein the temperature-sensitive polymer component comprises the polymerization product of a monomer selected from N-isopropylacrylamide and butylmethyacrylate.

19. The graft copolymer of any one of any one of claims 1, 2, 3 or 4 wherein the temperature sensitive polymer component is a block copolymer of ethylene oxide and propylene oxide.

20. The graft copolymer of any one of claims 1, 2, 3 or 4 wherein the pH-sensitive polymer component is lightly cross-linked.

21. The graft copolymer of any one of claims 1, 2, 3 or 4 wherein the temperature-sensitive polymer component is lightly cross-linked.

* * * * *

UNITED STATES PATENT AND TRADEMARK OFFICE
CERTIFICATE OF CORRECTION

PATENT NO.    : 6,486,213 B1
DATED         : November 26, 2002
INVENTOR(S)   : Guohua Chen et al.

It is certified that error appears in the above-identified patent and that said Letters Patent is hereby corrected as shown below:

<u>Column 60,</u>
Line 18, "pH-sensitive polymer, component" should read as -- pH-sensitive polymer component --.
Line 30, "claims 1 or 2" should read as -- claims 1 or 3 --.

Signed and Sealed this

Twenty-seventh Day of May, 2003

JAMES E. ROGAN
*Director of the United States Patent and Trademark Office*